(12) United States Patent
Narimatsu et al.

(10) Patent No.: US 8,227,213 B2
(45) Date of Patent: Jul. 24, 2012

(54) β1,3-N-ACETYL-D-GALACTOSAMINE TRANSFERASE PROTEIN, NUCLEIC ACID ENCODING THE SAME AND METHOD OF EXAMINING CANCERATION USING THE SAME

(75) Inventors: Hisashi Narimatsu, Tsukuba (JP); Akira Togayachi, Tsukuba (JP); Niro Inaba, Hachioji (JP); Toru Hiruma, Tsukuba (JP); Yasuko Ishizuka, Tsukuba (JP)

(73) Assignee: National Institute of Advanced Science & Technology, Tokyo (JP)

( * ) Notice: Subject to any disclaimer, the term of this patent is extended or adjusted under 35 U.S.C. 154(b) by 0 days.

(21) Appl. No.: 12/772,117

(22) Filed: Apr. 30, 2010

(65) Prior Publication Data

US 2010/0279355 A1 Nov. 4, 2010

Related U.S. Application Data

(62) Division of application No. 12/216,077, filed on Jun. 30, 2008, now abandoned, which is a division of application No. 10/539,450, filed as application No. PCT/JP2004/000608 on Jan. 23, 2004, now abandoned.

(30) Foreign Application Priority Data

| Jan. 23, 2003 | (JP) | ................................ 2003-14792 |
| Aug. 1, 2003 | (JP) | ................................ 2003-285310 |
| Nov. 21, 2003 | (JP) | ................................ 2003-392555 |

(51) Int. Cl.
*C12P 19/18* (2006.01)
*C12P 19/46* (2006.01)
*C12P 19/26* (2006.01)
*C12P 19/30* (2006.01)
*C12P 33/20* (2006.01)
*C12P 21/06* (2006.01)
*C12P 19/34* (2006.01)
*C12N 9/10* (2006.01)
*C07K 1/00* (2006.01)
*C07H 21/04* (2006.01)

(52) U.S. Cl. ............... 435/97; 435/79; 435/84; 435/89; 435/53; 435/193; 435/69.1; 435/91.1; 530/350; 536/23.1; 536/23.2

(58) Field of Classification Search .............. 435/97, 435/79, 84, 89, 53, 193, 69.1, 91.1; 530/350; 536/23.1, 23.2

See application file for complete search history.

(56) References Cited

U.S. PATENT DOCUMENTS

| 7,223,580 | B2 | 5/2007 | Narimatsu et al. |
| 7,241,605 | B1 | 7/2007 | Narimatsu et al. |
| 7,262,039 | B1 | 8/2007 | Narimatsu et al. |
| 7,279,310 | B2 | 10/2007 | Narimatsu et al. |
| 7,323,324 | B2 | 1/2008 | Narimatsu et al. |
| 7,396,666 | B2 | 7/2008 | Narimatsu et al. |
| 7,494,800 | B2 | 2/2009 | Narimatsu et al. |
| 2005/0186570 | A1 | 8/2005 | Narimatsu et al. |
| 2006/0177822 | A1 | 8/2006 | Narimatsu et al. |
| 2006/0234220 | A1 | 10/2006 | Narimatsu et al. |
| 2006/0234232 | A1 | 10/2006 | Narimatsu et al. |
| 2008/0050745 | A1 | 2/2008 | Narimatsu et al. |
| 2008/0299615 | A1 | 12/2008 | Narimatsu et al. |
| 2009/0081668 | A1 | 3/2009 | Narimatsu et al. |
| 2009/0197273 | A1 | 8/2009 | Narimatsu et al. |

FOREIGN PATENT DOCUMENTS

| JP | 2002-85069 | 3/2002 |
| WO | 01/44479 | 6/2001 |
| WO | 01/79556 | 10/2001 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Broun et al. "Catalytic plasticity of fatty acid modificaiton enzymes underlying chemical diversity of plant lipids" Sci. 282:1315-1317 (1998).
Cameron "Recent advances in transgenic technology" Mol. Biotechnol. 7:253-265 (1997).
Carninci et al. "*Mus musculus* adult male urinary bladder cDNA Riken full-length enriched library, clone: 9530006I10 product: Hypothetical glycosyltransferase family 31 containing protein, full insert sequence" Accession No. AK035259 (2002).

(Continued)

*Primary Examiner* — Ganapathirama Raghu
(74) *Attorney, Agent, or Firm* — Nixon & Vanderhye P.C.

(57) ABSTRACT

The N-acetyl-D-galactosamine transferase protein of the present invention is characterized by transferring N-acetyl-D-galactosamine to N-acetyl-D-glucosamine with β1,3 linkage, and it preferably has the amino acid sequence shown in SEQ ID NO: 2 or 4. The canceration assay according to the present invention uses a nucleic acid for measurement which hybridizes under stringent conditions to the nucleotide sequence shown in SEQ ID NO: 1 or 3 or a nucleotide sequence complementary to at least one of them.

11 Claims, 16 Drawing Sheets

OTHER PUBLICATIONS

Hiruma et al. "A novel human β1,3-N-acetylgalactosaminyltransferase that synthesizes a unique carbohydrate structure, GalNAcβ1-3GlcNAc" J. Biol. Chem. 279:14087-14095 (2004).

Hiruma et al. "Cloning and analyzing functions of a novel human glycosyltransferase of β3GalNAc-T2 gene" Biotechnol. Symp. Abstracts, 21:137-140 (2003) in Japanese with partial English translation.

Iida et al. "Incorporation of N-acetylgalacatosamine into consecutive threonine residues in MuC2 tandem repeat by recombinant human N-acetyl-D-galactosamine transferase-T1, T2 and T3" FEBS Lett. 449:230-234 (1999).

Iwai et al. "Molecular cloning and characterization of a novel UDP-GlcNAc: GalNAc-peptide β-1,3-N-acetylglucosaminyltransferase (β3Gn-T6), an enzyme synthesizing the core 3 structure of o-glycans" J. Biol. Chem. 277:12802-12809 (2002).

Kawai et al. "Functional annotation of a full-length mouse cDNA collection" Nature 409:685-690 (2001).

Okajima et al. "Expression cloning of human globoside synthase cDNAs" J. Biol. Chem. 275:40498-40503 (2000).

Mullins et al. "Molecular medicine in genetically engineered animals: Transgenesis in the rat and larger mammals" J. Clin. Invest. 97:1557-1560 (1996).

Mullins et al. "Transgenesis in nonmurine species" Hypertension 22:630-633 (1993).

Seffernick et al. "Melamine deaminase and atrazine chlorohydrolase: 98 percent identical but functionally different" J. Bacteriol. 183:2405-2410 (2001).

Strausberg et al. Generation and initial analysis of more than 15,000 full-length human and mouse cDNA sequences. Proc. Natl. Acad. Sci. USA 99:16899-16903 (2002).

Strausberg et al. "*Homo sapiens* UDP-GalNAc:betaG1cNAc beta 1,3-galactosaminyltransferase, polypeptide 2, mRNA (cDNA clone MGC: 39558 image: 4826983) complete cds" Accession No. BC029564 (2002).

Taga et al. "Sequential changes in glycolipid expression during human B cell differentiation: Enzymatic bases" Biochem. Biophys. Acta 1254:56-65 (1995).

Treloar et al. "An effect of puromycin on galactosyltransferase of Golgi-rich fractions from rat liver" J. Biol. Chem. 249:6628-6632 (1974).

Uyama et al. "Molecular cloning and expression of human chondroitin N-acetylgalactosaminyltransferase: The key enzyme for chain initiation and elongation of chondroitin/dermatan sulfate on the protein linkage region tetrasaccharide shared by heparin/heparan sulfate" J. Biol. Chem. 277:8841-8846 (2002).

Wandal et al. "Substrate specificities of three members of the human UDP-N-acetyl-α-D-galactosamine: Polypeptide N-acetylgalactosaminyltransferase family, GalNAc-T1, -T2, and -T3" J. Biol. Chem. 272:23503-23514 (1997).

Wigley et al. "Site-specific transgene insertion: An approach" Reprod. Fertil. Dev. 6:585-588 (1994).

Whisstock et al. "Prediction of protein function from protein sequence and structure" Quar. Rev. Biophys. 36:307-340 (2003).

Witkowski et al. "Conversion of a β-ketoacyl synthase to a malonyl decarboxylase by replacement of the active-site cysteine with glutamine" Biochem. 38:11643-11650 (1999).

Wojczyk et al. "cDNA cloning and expression of UDP-N-acetyl-D-galactosamine: Polypeptide N-acetylgalactosaminyltransferase T1 from *Toxoplasma gondii*" Mol. Biochem. Parasitol. 93:93-107 (2003).

International Search Report for PCT/JP2004/000608 dated Mar. 2, 2004.

Supplementary European Search Report for EP 04704763.4 dated Mar. 28, 2006.

* cited by examiner

Figure 2A (continued)

G34, noesyprtp, 0.9s, 298K, 03-01-09

Current Data Parameters
NAME                G34
EXPNO                 9
PROCNO                1

F2 - Acquisition Parameters
Date_          20021228
Time              12.12
INSTRUM          dmx750
PROBHD     5 mm 1H XYZ-
PULPROG        noesyprtp
TD                 2048
SOLVENT             D2O
NS                   16
DS                   16
SWH           6009.615 Hz
FIDRES        2.934382 Hz
AQ            0.1704436 sec
RG                 2048
DW              83.200 usec
DE               4.50 usec
TE              300.0 K
d0           0.00000300 sec
D1           1.39999998 sec
D8           0.89999998 sec
d11          0.03000000 sec
d12          0.00002000 sec
d13          0.00000300 sec
IN0          0.00008331 sec ============ CHANNEL f1 ============
NUC1                 1H
P1                8.65 usec
PL1               1.00 dB
PL9              75.00 dB
SFO1       750.1335265 MHz F1 - Acquisition parameters
ND0                   2
TD                  512
SFO1          750.1335 MHz
FIDRES       11.721681 Hz
SW               8.001 ppm F2 - Processing parameters
SI                 1024
SF         750.1299973 MHz
WDW               QSINE
SSB                   2
LB                0.00 Hz
GB                    0
PC                 1.00

F1 - Processing parameters
SI                 1024
MC2                TPPI
SF         750.1299974 MHz
WDW               QSINE
SSB                   2
LB                0.00 Hz
GB                    0

2D NMR plot parameters
CX2              15.00 cm
CX1              15.00 cm
F2PLO            4.500 ppm
F2LO           3375.58 Hz
F2PHI            3.300 ppm
F2HI           2475.43 Hz
F1PLO            4.500 ppm
F1LO           3375.58 Hz
F1PHI            3.300 ppm
F1HI           2475.43 Hz
F2PPMCM        0.08000 ppm/cm
F2HZCM        60.01040 Hz/cm
F1PPMCM        0.08000 ppm/cm
F1HZCM        30.01040 Hz/cm Figure 2B (continued)

G34, noesyprtp, 0.9s, 298K, 03-01-09

Current Data Parameters
NAME                G34
EXPNO                 9
PROCNO                1

F2 — Acquisition Parameters
Date_           20021228
Time               12.12
INSTRUM          dmx750
PROBHD      5 mm 1H XYZ-
PULPROG        noesyprtp
TD                  2048
SOLVENT             D2O
NS                    16
DS                    16
SWH          6009.615  Hz
FIDRES       2.934382  Hz
AQ           0.1704436 sec
RG                  2048
DW             83.200  usec
DE              4.50   usec
TE              300.0  K
d0           0.00000300 sec
D1           1.39999998 sec
D8           0.89999998 sec
d11          0.03000000 sec
d12          0.00002000 sec
d13          0.00000300 sec
IN0          0.00008331 sec ============ CHANNEL f1 ============
NUC1                1H
P1              8.65   usec
PL1             1.00   dB
PL9            75.00   dB
SFO1       750.1335265 MHz F1 — Acquisition parameters
ND0                  2
TD                 512
SFO1         750.1335  MHz
FIDRES       11.721681 Hz
SW            8.001   ppm F2 — Processing parameters
SI                1024
SF         750.1299973 MHz
WDW              QSINE
SSB                  2
LB              0.00   Hz
GB                   0
PC              1.00

F1 — Processing parameters
SI                1024
MC2                TPPI
SF         750.1299974 MHz
WDW              QSINE
SSB                  2
LB              0.00   Hz
GB                   0

2D NMR plot parameters
CX2            15.00   cm
CX1            15.00   cm
F2PLO           3.907  ppm
F2LO         2930.51   Hz
F2PHI           3.296  ppm
F2HI         2472.75   Hz
F1PLO           4.501  ppm
F1LO         3376.70   Hz
F1PHI           4.298  ppm
F1HI         3224.32   Hz
F2PPMCM         0.04068 ppm/cm
F2HZCM         30.51759 Hz/cm
F1PPMCM         0.01354 ppm/cm
F1HZCM         10.15880 Hz/cm

Figure 3

Table 1

| 1H Chemical shift | A (ppm) | B (ppm) |
|---|---|---|
| $\delta 1$ | 4.398* | 4.381* |
| $\delta 2$ | 3.687 | 3.711* |
| $\delta 3$ | 3.599* | 3.655 |
| $\delta 4$ | 3.435* | 3.811* |
| $\delta 5$ | 3.358* | 3.562* |
| $\delta 6$ | 3.681 | 3.645 |
| $\delta 6$ | 3.844* | 3.698 |
| $\delta CH_3$ | 1.828* | 1.892* |

Table 2

| Coupling coefficient | A (Hz) | B (Hz) |
|---|---|---|
| J12 | 8.4 | 8.4 |
| J23 | 9.8 | 10.6 |
| J34 | 8.6 | 5.9 |
| J45 | 9.2 | 3.3? |
| J56a | 5.8 | 5.5 |
| J56b | 2.2 | 4.0 |
| J6a6b | 12.4 | 12.1 |

Figure 4

Table 3

| f2 | Signal | f1 | Signal | 300 ms | 600 ms | 900 ms |
|---|---|---|---|---|---|---|
| 7.265 | phenyl | 1.828 | $CH_3$ | - | w | w |
| 7.265 | phenyl | 4.557 | $CH_2$(high) | w | m | m |
| 7.265 | phenyl | 4.778 | $CH_2$(low) | w | m | m |
| 7.265 | phenyl | 4.398 | A1 | - | - | m |
| 4.557 | $CH_2$ | 4.398 | A1 | - | w | m |
| 4.398 | A1 | 4.557 | $CH_2$ | - | w | w |
| 4.398 | A1 | 3.358 | A5 | - | m | m |
| 4.381 | B1 | 3.599 | A3 | - | w | m |
| 4.381 | B1 | 3.562 | B5 | - | m | m |
| 3.599 | A3 | 4.381 | B1 | - | w | m |
| 3.562 | B5 | 4.381 | B1 | - | m | s |
| 3.358 | A5 | 4.398 | A1 | - | m | m |

Figure 5

```
β3Gal-T1   1:FLVILISTTHKEFDARQAIRETWGDENNFKGIK-IA-T-LFLLG---KNAD--PVL---- 48
β3Gal-T2   1:FLILLIAAEPGQIERRAIRQTWGNESLAPGIQ-IT-R-IFLLGLSIKLN---GYL---- 50
β3Gal-T3   1:FLVILVTSHPSDVKARQAIRVTWGEKKSWWGYE-VL-T-FFLLGQEAEKED--KML---- 51
β3Gal-T5   1:FLVLLVTSSHKQLAERMAIRQTWGKERMVKGKQ-LK-T-FFLLGTTSSAAE--T------ 49
β3Gal-T6   1:FLAVLVASAPRAAERRSVIRSTWLARRGAPGD--VWAR--FAVGTAGLGAE--ER----- 49
G34        1:DVVVGVLSARNNHELRNVIRSTWMRHLLQHPTLSQRVLVKFIIGAHGCEVPVEDREDPYS 60
                          *  * ** **       M1             * *

β3Gal-T1  49:-N------------------------------------------------------- 49
β3Gal-T2  51:-Q------------------------------------------------------- 51
β3Gal-T3  52:-A------------------------------------------------------- 52
β3Gal-T5  50:--------------------------------------------------------- 50
β3Gal-T6  50:--------------------------------------------------------- 50
G34       61:CKLLNITNPVLNQEIEAFSLSEDTSSGLPEDRVVSVSFRVLYPIVITSLGVFYDANDVGF 120

β3Gal-T1  50:--------------------------------------------------------- 50
β3Gal-T2  52:--------------------------------------------------------- 52
β3Gal-T3  53:--------------------------------------------------------- 53
β3Gal-T5  50:--------------------------------------------------------- 50
β3Gal-T6  50:--------------------------------------------------------- 50
G34      121:QRNITVKLYQAEQEEALFIARFSPPSCGVQVNKLWYKPVEQFILPESFEGTIVWESQDLH 180

β3Gal-T1  50:--------------------------------------------------------- 50
β3Gal-T2  52:--------------------------------------------------------- 52
β3Gal-T3  53:--------------------------------------------------------- 53
β3Gal-T5  50:--------------------------------------------------------- 50
β3Gal-T6  50:--------------------------------------------------------- 50
G34      181:GLVSRNLHKVTVNDGGGVLRVITAGEGALPHEFLEGVEGVAGGFIYTIQEGDALLHNLHS 240

β3Gal-T1  50:---------------QMVEQESQIFHDIIVE-DFIDSYHNLTLKTLMGMRWVATFCSKA 92
β3Gal-T2  52:---------------RAILEESRQYHDIIQQ-EYLDTYYNLTLKTIMGMNWVATYCPHI 94
β3Gal-T3  53:---------------LSLEDEHLLYGDIIRQ-DFLDTYNNLTLKTIMAPRWVTEPCPNA 95
β3Gal-T5  50:---------------KEVDQESQRHGDIIQK-DFLDVYYNLTLKTMGIEWVHRFCPQA 92
β3Gal-T6  50:---------------RALEREQARHGDLLLLPALRDAYENLTAKVLAMLAWLDEHVAF- 92
G34      241:RPQRLIDHIRNLHEEDALLKEESSIYDDIVFV-DVIDTYRNVPAKLLNFYRWTVETTSFN 299
                            *       *  *   * * *         * * *    *
              — M2 —

β3Gal-T1  93:KIYVMKTDSDIFVNMDNLIYKLLKPSTKPRRRYFTGYVINGG---P-IRDVRSKWYMPRDL 148
β3Gal-T2  95:HYVMKTDSDMFVNTEYLINKLLKPDLPPRHNYFTGYLMRGYA--P-NRNKDSKWYMPPDL 151
β3Gal-T3  96:KIYVMKTDTDVFINTGNLVKYLLNLNHSEKF--FTGYPLIDNY--S-YRGFYQKTHISYQE 150
β3Gal-T5  93:KFVMKTDSDMFINVDYLTELLLKNRTTRF-FTGFLNEF--P-IROPFSKWFVSKSE 147
β3Gal-T6  93:EFVLKADDDSPARLDALLAELRAREPARRRRLYWGFFSGRGRVKPGGRWREAAWQLCD-- 150
G34      300:-LLLKTDDDCYIDLEAVPNRIVQKNLDGPNF-WWGNFRLNWAV---DRT--QKWQEL--E 350
                * * *                                        *

β3Gal-T1 149:YPDSNYPPF-CSGTGYIFSADVAELIYKTSLHTRLLHLEDVYVGLCLRKLGIHPFQN-SG 206
β3Gal-T2 152:YPSERYPVF-CSGTGYVPSGDLAEKIFKVSLGIRRLHLEDVYVGICLAKLRIDPVPPPNE 210
β3Gal-T3 151:YPFKVFPPY-CSGLGYIMSRDLVPRIYEMMGHVKPIKFEDVYVGICLNLLKVNIHIPEDT 209
β3Gal-T5 148:YPWDRYPPF-CSGTGYVPSGDVASQVYNVSKSVPYIKLEDVFVGLCLERLNIRLEELHSQ 206
β3Gal-T6 151:YYL---PYAL--GGGYVLSADLVHYLRLSRDYLRAWHSEDVSLGAWLA--PVDVQREHD- 202
G34      351:YPSPAYPAFAC-GSGYVISKDIVKWLASNSGRLKTYQGEDVSMGIVMAAIGPKRYQD-SL 408
              *        * *   **  *                *** *       — M3

β3Gal-T1 207:---FNHWKMAYSLCRYRRVITVHQISPEEMHRIWNDMSSKKHLRC-------------- 248
β3Gal-T2 211:FVFNHWRVSYSSCKYSHLITSHQFQPSELIKYWNHLQQNKHNACANAAKEKA-------- 262
β3Gal-T3 210:NLFFLYRIHLDVCQLRRVIAAHGFSSKEIITFWQVMLRN--TTCHY------------- 253
β3Gal-T5 207:PTFFPGGLRFSVCLFRRIVACHFIKPRTLLDYWQALENSRGEDCP-PV----------- 253
β3Gal-T6 203:PRFDTE-YRSRGCSNQYLVTHKQ-SLEDMLEKHATL-AREGRLCKREVQLRLSYVYDWSA 259
G34      409:-----WLC-EKTCETGMLSSP-QYSPWELTELWK-LKERCGDPC-RC-QAR--------- 449
                      *                          *

β3Gal-T1 249:-------------                                             249
β3Gal-T2 263:----GRYRHRKLH-                                            271
β3Gal-T3 254:-------------                                             254
β3Gal-T5 254:-------------                                             254
β3Gal-T6 260:PPSQCCQR-REGIP                                            272
G34      450:-------------                                             450
```

Figure 6

```
                           M1
b3GnT2    FLLLAIKSLTPHFARRO AIRESWGQES-NAGNQT----VVRVFLLGQTPPEDNHP-DLSDM
b3GnT3    FLLLVIKSSPSHYVRRE LLRRTWGRER-KVRGLQ---LRLLFLVGTASNPHEAR-KVNRL
b3GnT4    FLLLAIKSQPGHVERRA AIRSTWGRVGGWARGRQ----LKLVFLLGVAG------SA-PPAQL
b3GnT5    LLLLFVKTAPENYDRRS GIRRTWGNEN-YVRSQLNANIKTLFALGTPNPLE-GE-ELQRK
b3Gal-T6  FLAVLVASAPRAVERRT AVRSTWLAPE-RRGGPED--VWARFAVGTGGLGS----EERRA
hGal-T1   FLVILISTTHKEFDARQ AIRETWGDEN-NFKGIK---IATLFLLGKNADP-----VLNQM
hGal-T2   FLILLIAAEPGQIEARR AIROTWGNES-LAPGIO----ITRIFLLGLSIKLN--G-YLQRA
hGal-T3   FLVILVTSHPSDVKARQ AIRVTHGEKK-SWWGYE----VLTFFLLGQEAEKE-DK-MLALS
hGal-T4   FLLILVCTAPEHLNQRN AIRASWGGLR-EARGLR----VQTLFLLGEPNAQHPVWGSQGSD
hGal-T5   FLVLLVTSSHKQLAERM AIROTWGKER-MVKGKO----LKTFFLLGTTSSA------AETKE
                *       *  **  *                  M2
b3GnT2    LKFESEKHQDILMW-NYRDTFFNLSLKEVLFLRWVSTSCPDTE FVFKGDDQVFVNTHHIL
b3GnT3    LELEAQTHGDILQW-DFHDSFFNLTLKQVLFLQWQETRCANAS FVLNGDDQVFAHTDNMV
b3GnT4    LAYESREFDDILQW-DFTEDFFNLTLKELHLQRWVVAACPQAH FMLKGDDQVFVHVPNVL
b3GnT5    LAWEDQRYNDIIQQ-DFVDSFYNLTLKLLMQFSWANTYCPHAK FLMTADDQIFIHMPNLI
b3Gal-T6  LELEQAQHGDLLLLPALRDAYENLTAKVLAMLTWILDER-VDF EFVLKADDDSFARLDAIL
hGal-T1   VEQESQIFHDIIVE-DFIDSYHNLTLKTLMGMRWVATFCSKAK YVMKTDSQIFVNMDNLI
hGal-T2   ILEESRQYHDIIQQ-EYLDTYYNLTIKTLMGMNWVATYCPHI PYVMKTDSQMFVNTEYLI
hGal-T3   LEDEHLLYGDIIRQ-DFLDTYNNLTLKTIMAFRWVTEFCPNAK YVMKTDTQVFINTGNLV
hGal-T4   LASESAAQGDILQA-AFQDSYRNLTLKTLSGLNWAEKHCPMAR YVLKTDDQVYVNVPELV
hGal-T5   VDQESQRHGDIIQK-DFLDVYYNLTLKTMMGIEWVHRFCPQAA FVMKTDSQMFINVDYLT
                *            **  *          *                 *  *
b3GnT2    NYLNS-----------------------LSKTKAKDLFIGDVIHNAGPHRDKKLKYYI
b3GnT3    FYLQD-----------------------HDP---GRHLFVGQLIQNVGPIRAFWSKYYV
b3GnT4    EFLDG-----------------------HDP---AQDLLVGDVIRQALPNRNTKVKYFI
b3GnT5    EYLQS-----------------------LEQIGVQDFWIGRVHRGAPPIRDKSSKYYV
b3Gal-T6  VDLRA-----------------------REPARRRRLYWGFFSGR--GRVKPGGRWRE
hGal-T1   YKLLK-----------------------PSTKPRRRYFTGYVING-GPIRDVRSKWYM
hGal-T2   NKLLK-----------------------PDLPPRHNYFTGYLMRGYAPNRNKDSKWYM
hGal-T3   KYLLN-----------------------LNH--SEKFFTGYPLIDNYSYRGFYQKTHI
hGal-T4   SELVLRGGRWGOWERSTEPOREAEOEGGOVLHSEEVPLLYLGRVHWRVNPSRTPGGRHRV
hGal-T5   ELLLK-----------------------KNR--TTRFFTGFLKLNEFPIRQPFSKWFV
                                                            *
                                                                      M3
b3GnT2    PEVVYSG----LYPPYAGGGGFLYSGHLALRLYHITDQVH-LYP IDDVYTGMCLQKLGLVP
b3GnT3    PEVVTQNE---RYPPYCGGGGFLLSRFTAAALRRAAHVLD-IFP IDDVFLGMCLELEGLKP
b3GnT4    PPSMYRAT---HYPPYAGGGGYVMSRATVRRLQAIMEDAE-LFP IDDVFVGMCLRRLGLSP
b3GnT5    SYEMYQWP---AYPDYTAGAAYVISGDVAAKVYEASQTLNSSLY IDDVFMGLCANKIGIVP
b3Gal-T6  AAWQLCD----YYLPYALGGGYVLSADLVHYLRLSREYLR-AWHS EDVSLGTWLAPVDVQR
hGal-T1   PRDLYPDS---NYPPFCSGTGYIFSADVAELIYKTSLHTR-LLHL EDVYYGLCLRKLGIHP
hGal-T2   PPDLYPSE---RYPVFCSGTGYVFSGDLAEKIFKVSLGIR-RLHL EDVYYGICLAKLRIDP
hGal-T3   SYQEYPFK---VFPPYCSGLGYIMSRDLVPRIYEMMGHVK-PIKF EDVYYGICLNLLKVNI
hGal-T4   SEEQWPHTWGPFPPYASGTGYVLSASAVQLILKVASRAP-LLPL EDVFVGVSARRGGLAP
hGal-T5   SKSEYPWD---RYPPFCSGTGYVFSGDVASQVYNVSKSVP-YIKL EDVFVGLCLERLNIRL
                      *     *                             **  *
b3GnT2    EKHKGFRTFDIE-----EKNKNNICSYVDLMLVHSRKPQEMIDIWSQLQSA--------
b3GnT3    ASHSGIRTSGVRAPSQHLSSFDPCFYRDLLLVHRFLPYEMLLMWDALNQP---------
b3GnT4    MHHAGFKTFGIRR----PLDPLDPCLYRGLLLVHRLSPLEMWTMWALVTDE--------
b3GnT5    QDHVFFS--GEGK-----TPYHPCIYEKMMTSHG-HLEDLQDLWKNATDPKVKTISKGFF
b3Gal-T6  EHDPRFD--TEYK--------SRGCNNQYLVTHKQ-SPEDMLEKQQMLLHEG--------

Note: " b3" represents a β1,3 linkage and " Gn" represents GlcNAc.
```

Figure 9 (continued)

| | Cell Line | Copy number (x 10000 /μg, total RNA) | |
|---|---|---|---|
| Neuroblastoma | SCCH-26 | 7.87 | 0.59 |
| | NAGAI | 19.53 | 1.45 |
| | NB-9 | 40.56 | 2.34 |
| | SK-N-SH | 14.93 | 0.74 |
| | SK-N-MC | 5.79 | 0.47 |
| | NB-1 | 20.90 | 0.54 |
| | IMR32 | 21.03 | 0.25 |
| Glioblastoma | T98G | 6.20 | 0.24 |
| | YKG-1 | 3.85 | 0.05 |
| | A172 | 13.38 | 0.87 |
| | GI-1 | 13.72 | 1.25 |
| | U118MG | 6.80 | 0.51 |
| | U251 | 28.90 | 1.89 |
| | KG-1-C | 9.09 | 0.55 |
| Lung Cancer | Lu130 | 6.80 | 0.42 |
| | Lu134A | 30.31 | 1.16 |
| | Lu134B | 6.76 | 0.40 |
| | Lu135 | 7.16 | 1.32 |
| | Lu139 | 10.66 | 0.50 |
| | Lu140 | 15.36 | 1.83 |
| | SBC-1 | 2.46 | 0.22 |
| | PC-7 | 9.08 | 0.20 |
| | PC-9 | 22.42 | 0.11 |
| | HAL-8 | 15.18 | 1.22 |
| | HAL-24 | 20.80 | 1.71 |
| | ABC-1 | 10.27 | 0.87 |
| | RERF-LC-MC | 22.85 | 2.15 |
| | EHHA-9 | 20.34 | 7.88 |
| | PC-1 | 2.13 | 0.18 |
| | EBC-1 | 4.41 | 0.19 |
| | PC-10 | 118.76 | 4.89 |
| | A549 | 27.10 | 2.63 |
| | LX-1 | 30.72 | 2.06 |
| Esophagus Cancer | ES1 | 23.03 | 2.53 |
| | ES2 | 16.07 | 0.65 |
| | ES6 | 42.76 | 2.96 |
| Gastric Cancer | MKN1 | 6.20 | 1.10 |
| | MKN28 | 8.56 | 0.99 |
| | MKN7 | 9.71 | 0.10 |
| | MKN74 | 3.46 | 0.81 |
| | MKN-45 | 7.32 | 2.13 |
| | HSC-43 | 42.82 | 1.67 |
| | KATOIII | 6.37 | 0.37 |
| | TMK-1 | 10.78 | 1.19 |

| | Cell Line | | |
|---|---|---|---|
| Colorectal Cancer | LSC | 11.76 | 0.57 |
| | LSB | 4.89 | 0.30 |
| | SW480 | 10.05 | 0.43 |
| | SW1116 | 24.09 | 1.39 |
| | Colo201 | 10.40 | 0.41 |
| | Colo205 | 6.80 | 0.88 |
| | C1 | 21.86 | 1.20 |
| | WiDr | 1.24 | 0.04 |
| | HCT8 | 82.17 | 6.24 |
| | HCT15 | 12.14 | 0.96 |
| The Other Organs | A204 | 67.94 | 4.37 |
| | A-431 | 30.59 | 2.52 |
| | SW1736 | 11.92 | 1.13 |
| | HepG2 | 2.27 | 0.35 |
| | Capan-2 | 19.43 | 1.24 |
| | 293T | 55.14 | 8.29 |
| | PA-1 | 3.52 | 0.56 |
| Leukemia | HL-60 | 2.08 | 0.11 |
| | K-562 | 17.08 | 1.77 |
| Lymphoma | Daudi | 2.41 | 0.20 |
| | Namalwa | 13.00 | 1.20 |
| | KHM-1B | 16.35 | 0.45 |
| | Ramos | 9.54 | 0.75 |
| | Raji | 11.56 | 1.31 |
| | Jurkat | 42.71 | 1.93 |
| | YKN45 | 10.12 | 0.56 |

Figure 10

```
mouse G34   1'  MRNWLVLLCP  CVLGAALHLW  HLWLRSPPDP  HNTGPSAADQ  SALFPHWKFS  HYDVVVGVLS
                **********  **********  *.*****. .  ..*...***   ****.**  .  **********
human G34   1"  MRNWLVLLCP  CVLGAALHLW  -LRLRSPPPA  CASGAGPADQ  LALFPQWKST  HYDVVVGVLS 61'  ARNNHELRNV  IRNTWLKNLL  HHPTLSQRVL  VKFIIGARGC  EVFVEDREDP  YSCRLLNITN
                ********  ....  .*******  ***.  ******** *.******
           60"  ARNNHELRNV  IRSTWMRHLL  QHPTLSQRVL  VKFIIGAHGC  EVFVEDREDP  YSCKLLNITN 121'  PVLNQEIEAF  SFPEDASSSR  LSEDRVVSVS  FRVLYPIVIT  SLGVFYDASD  VGFQRNITVK
                **********  *....   *.******  ******  ******.- ********
          120"  PVLNQEIEAF  SLSEDTSSG-  LPEDRVVSVS  FRVLYPIVIT  SLGVFYDAND  VGFQRNITVK 181'  LYQTEQEEAL  FIARFSPPSC  GVQVNKLWYK  PVBQFILPES  FEGTIVWESQ  DLHGLVSRNL
                *.**  ******  ******  ******  ******  ********
          179"  LYQAEQEEAL  FIARFSPPSC  GVQVNKLWYK  PVBQFILPES  FEGTIVWESQ  DLHGLVSRNL 241'  HRVTVNDGGG  VLRVLAAGEG  ALPHEFMEGV  EGVAGGFIYT  VQEGDALLRS  LYSRPQRLAD
                *.******  .*  *.*   ********  .*****..  *.******.*
          239"  HKVTVNDGGG  VLRVITAGEG  ALPHEFLEGV  EGVAGGFIYT  IQEGDALLHN  LBSRPQRLID 301'  HIQDLQVEDA  LLQEESSVHD  DIVFVDVVDT  YRNVPAKLLN  FYRWTVESTS  FDLLLKTDDD
                **..*..*  .*****.. *  ********  ******  **.  *.********
          299"  HIRNLHEEDA  LLKEESSIYD  DIVFVDVVDT  YRNVPAKLLN  FYRWTVETTS  FNLLLKTDDD 361'  CYIDLEAVFN  RIAQKNLDGP  NFWWGNFRLN  WAVDRTGKWQ  ELEYPSPAYP  AFACGSGYVI
                ********  .*****  ******  ******  ******  ********
          359"  CYIDLEAVFN  RIVQKNLDGP  NFWWGNFRLN  WAVDRTGKWQ  ELEYPSPAYP  AFACGSGYVI 421'  SKDIVDWLAG  NSRRLKTYQG  EDVSMGIWMA  AIGPKRHQDS  LWLCEKTCET  GMLSSPQYSP
                ****.*.   ***  ******  **.*  ********  ********
          419"  SKDIVKWLAS  NSGRLKTYQG  EDVSMGIWMA  AIGPKRYQDS  LWLCEKTCET  GMLSSPQYSP 461'  EELSKLWELK  ELCGDPCQCB  AKVR
                ...**   * *****.*.  *.
          479"  WELTELWKLK  ERCGDPCRCQ  AR
```

β1,3-N-ACETYL-D-GALACTOSAMINE TRANSFERASE PROTEIN, NUCLEIC ACID ENCODING THE SAME AND METHOD OF EXAMINING CANCERATION USING THE SAME

This application is a divisional of application Ser. No. 12/216,077, filed Jun. 30, 2008, abandoned; which is a divisional of application Ser. No. 10/539,450, filed Dec. 23, 2005, abandoned; which is a U.S. national stage under 35 U.S.C. 371 of Application No. PCT/JP2004/000608, filed Jan. 23, 2004; the entire contents of which are hereby incorporated by reference.

TECHNICAL FIELD

The present invention relates to a novel β1,3-N-acetyl-D-galactosaminyltransferase protein and a nucleic acid encoding the same, as well as a canceration assay using the same, etc.

BACKGROUND ART

Recent attention has been focused on the in vivo roles of sugar chains and/or complex carbohydrates. For example, factors for determining blood types are glycoproteins, and it is glycolipids that are involved in the functions of the nervous system. Thus, enzymes having the ability to synthesize sugar chains constitute an extremely important key to analyzing physiological activities provided by various sugar chains.

For example, N-acetyl-D-galactosamine (hereinafter also referred to as "GalNAc") is among the components constituting glycosaminoglycans, as well as being a sugar residue found in various sugar chain structures such as glycosphingolipids and mucin-type sugar chains. Thus, an enzyme transferring GalNAc will serve as an extremely important tool in analyzing the roles of sugar chains in various tissues in vivo.

As described above, attention has been focused on the in vivo roles of sugar chains, but it cannot be said that sufficient headway has been made in analyzing in vivo sugar chain synthesis. This is in part because the mechanism of sugar chain synthesis and the in vivo localization of sugar synthesis have not been fully analyzed. In analyzing the mechanism of sugar chain synthesis, it is necessary to analyze glycosylation enzymes (particularly glycosyltransferases) and to analyze what kind of sugar chains are synthesized by means of the enzymes. To this end, there is a strong demand for searching novel glycosyltransferases and analyzing their functions.

There are some reports of glycosyltransferases having the ability to transfer GalNAc (Non-patent Documents 1 to 4). For example, among human GalNAc transferases, enzymes transferring GalNAc with "β1,4 linkage" are known (Non-patent Document 1) and enzymes using "galactose" as their acceptor substrate are known as enzymes transferring GalNAc with β1,3 linkage (Non-patent Document 2) ("β1,3" or "β3" as used herein refers to a glycosidic linkage between an α-hydroxyl group at the 1-position of a sugar residue in an acceptor substrate and a hydroxyl group at the 3-position of a sugar residue to be transferred and linked thereto).

On the other hand, in higher organisms like humans, no enzyme is known to transfer GalNAc with "β1,3 linkage" to "N-acetylglucosamine" (hereinafter also referred to as "GlcNAc").

Although there is a report showing that the sugar chain structure in which GalNAc and GlcNAc are linked in a β1,3 fashion was confirmed in sugar chains on neutral glycolipids of fly, a kind of arthropod (Non-patent Document 5), it has been believed that such a sugar chain structure is not present in mammals, particularly in humans, to begin with.

Patent Document 1
International Patent Publication No. WO 01/79556
Non-Patent Document 1
Cancer Res. 1993 Nov. 15; 53(22):5395-400: Yamashiro S, Ruan S, Furukawa K, Tai T, Lloyd K O, Shiku H, Furukawa K. Genetic and enzymatic basis for the differential expression of GM2 and GD2 gangliosides in human cancer cell lines.
Non-Patent Document 2
Biochim Biophys Acta. 1995 Jan. 3; 1254(1):56-65: raga S, Tetaud C, Mangeney M, Tursz T, Wiels J. Sequential changes in glycolipid expression during human B cell, differentiation: enzymatic bases.
Non-Patent Document 3
Proc Natl Acad Sci USA. 1996 Oct. 1; 93(20):10697-702: Haslam D B, Baenziger J U. Related Articles, Links, Expression cloning of Forssman gly colipid synthetase: a novel member of the histo-blood group ABO gene family.
Non-Patent Document 4
J Biol Chem. 1997 Sep. 19; 272(38): 23503-14: Wandall H H, Hassan H, Mirgorodskaya E, Kristensen A K, Roepstorff P, Bennett E P, Nielsen P A, Hollingsworth M A, Burchell J, Taylor-Papadimitriou J, Clausen H. Substrate specificities of three members of the human, UDP-N-acetyl-alpha-D-galactosamine: Polypeptide N-acetylgalactosaminyltransferase family, GalNAc-T1, -T2, and -T3.
Non-Patent Document 5
J. Biochem. (Tokyo) 1990 June; 107(6); 899-903: Sugita M. Inagaki F, Naito H, Hori T., Studies on glycosphingolipids in larvae of the green-bottle fly, *Lucilia caesar*: two neutral glycosphingolipids having large straight oligosaccaride chains with eight and nine sugars.

DISCLOSURE OF THE INVENTION

A problem to be solved by the present invention is to provide a polypeptide which is a mammal-derived (particularly human-derived) glycosyltransferase and which has a novel transferase activity to transfer GalNAc with β1,3 linkage to GlcNAc, as well as a nucleic acid encoding such a polypeptide, etc.

Another problem to be solved by the present invention is to provide a transformant expressing the nucleic acid in host cells, a method for producing the encoded protein by allowing the transformant to produce the protein and then collecting the protein, and an antibody recognizing the protein.

On the other hand, since sugar chain synthesis may be affected by canceration, the identification and expression analysis of such a glycosylation enzyme can be expected to provide an index useful for cancer diagnosis, etc. The present invention also provides detailed procedures and criteria useful for canceration assay or the like by analyzing and comparing, at the tissue or cell line level, the transcription level of such a protein which varies in correlation with canceration or malignancy.

BRIEF DESCRIPTION OF DRAWINGS

FIG. 3 is a table summarizing NOE in NMR shown in FIG. 2. Various conditions for the data in Table 1 are as follows: 1.08 mM, 298K, $D_2O$, $CH_2$(high)=4.557 ppm for non-marked data, chemical shifts for data marked with * are $CH_2$(low)=4.778 ppm, phenyl(ortho)=7.265 ppm, phenyl(meta)=7.354 ppm and phenyl(para)=7.320 ppm, calculated from the 1D spectrum.

FIG. 4 is a table summarizing relevant data (tentative NOE) for each pyranose with respect to NMR shown in FIG. 2 (s: strong, m: medium, w: weak, vw: very weak, A: GlcNAc, B: GalNAc).

FIG. 5 shows a comparison of amino acid sequences between G34 enzyme protein according to this example and known β3Gal transferases: β3Gal-T1(SEQ ID NO: 19 from 1 to 248), β3Gal-T2 (SEQ ID NO: 20 from 1 to 271), β3Gal-T3 (SEQ ID NO: 21 from 1 to 253), β3Gal-T5 (SEQ ID NO: 22 from 1 to 253), β3Gal-T6 (SEQ ID NO: 23 from 1 to 272), and G34 (SEQ ID NO: 2 from 52 to 500).

FIG. 6 shows a comparison of motifs involved in the β3-linking activity between G34 enzyme protein according to this example and various known β3-linking glycosyltransferases: b3GnT2 (SEQ ID NO: 24 from 1 to 251), b3GnT3 (SEQ ID NO: 25 from 1 to 254), b3GnT4 (SEQ ID NO: 26 from 1 to 248), b3GnT5 (SEQ ID NO: 27 from 1 to 259), b3Gal-T6 (SEQ ID NO: 23 from 1 to 240), hGal-T11 (SEQ ID NO: 19 from 1 to 217), hGal-T2 (SEQ ID NO: 20 from 1 to 204), hGal-T3 (SEQ ID NO: 21 from 1 to 203), hGal-T4 (SEQ ID NO: 28), and hGal-T5 (SEQ ID NO: 22 from 1 to 200). "b3" represents a β1-3 linkage and "Gn" represents GlcNAc.

FIG. 10 shows amino acid sequence alignment between mouse G34 according to this example (upper; SEQ ID NO: 4) and human G34 (lower; SEQ ID NO: 2).

DETAILED DESCRIPTION OF THE INVENTION

Figure 1:
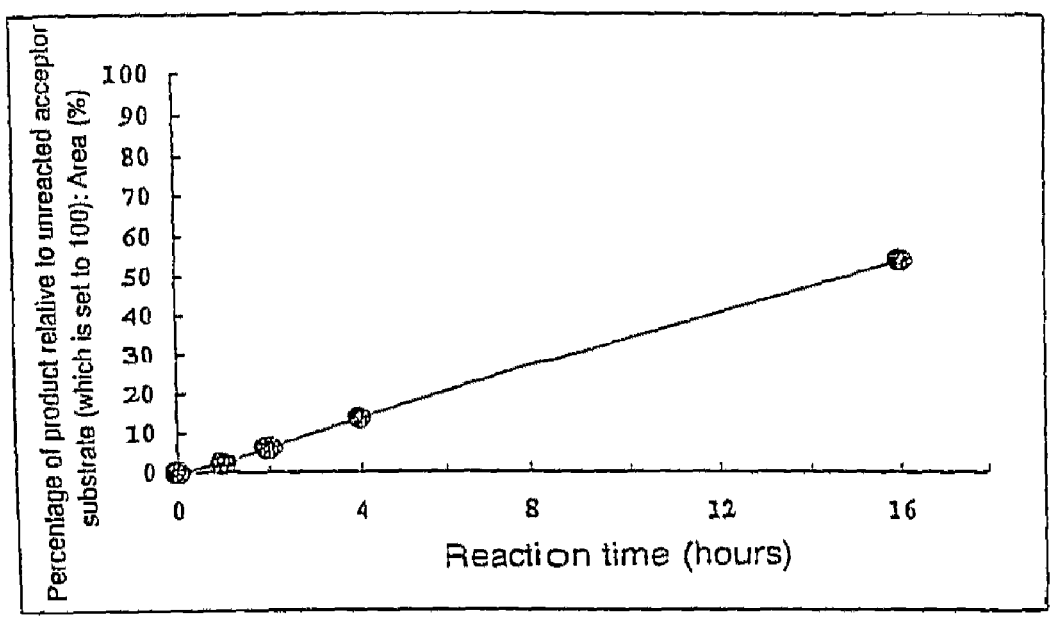
FIG. 1 is a diagram showing changes in the activity of the G34 enzyme protein according to this example, plotted against the reaction time.

To solve the problems stated above, the inventors of the present invention have attempted to isolate and purify a nucleic acid of interest, which may have high sequence identity, on the basis of the nucleotide sequence of an enzyme gene functionally similar to the intended enzyme. More specifically, first, the sequence of a known glycosyltransferase β3 galactosyltransferase 6 (β3GalT6) was used as a query for a BLAST search to thereby find a sequence with homology (GenBank No. AX285201). It should be noted that this nucleotide sequence was known as the sequence of SEQ ID NO: 1006 disclosed in International Publication No. WO 01/79556 (Patent Document 1 listed above), but its activity remained unknown.

First, the inventors of the present invention have independently cloned the above gene by PCR, have determined its nucleotide sequence (SEQ ID NO: 1) and putative amino acid sequence (SEQ ID NO: 2), and have succeeded in identifying a certain biological activity of a polypeptide encoded by the nucleic acid, thus completing the present invention. Moreover, when using the sequence as a query to search mouse genes, the inventors have found the nucleotide sequence of SEQ ID NO: 3 and its putative amino acid sequence (SEQ ID NO: 4).

The gene having the nucleotide sequence of SEQ ID NO: 1 and the protein having the amino acid sequence of SEQ ID NO: 2 were designated human G34, while the gene having the nucleotide sequence of SEQ ID NO: 3 and the protein having the amino acid sequence of SEQ ID NO: 4 were designated mouse G34.

According to the studies of the inventors, the above G34 protein uses an N-acetyl-D-galactosamine residue as a donor substrate and an N-acetyl-D-glucosamine residue as an acceptor substrate. As detailed later in Example 2, the G34 protein was found to retain three motifs in its amino acid sequence, which are well conserved in the enzyme family transferring various sugars (e.g., galactose, N-acetyl-D-glucosamine) in the linking mode of β1,3. In light of these points, the G34 protein was unexpectedly believed to have transferase activity to synthesize a novel sugar chain structure "GalNAc-β1,3-GlcNAc," for which no report has been made for mammals, particularly humans. The linking mode was actually confirmed by NMR.

Namely, the present invention relates to a β1,3-N-acetyl-D-galactosaminyltransferase protein which transfers N-acetyl-D-galactosamine to N-acetyl-D-glucosamine with β1,3 linkage.

An enzyme protein according to a preferred embodiment of the present invention may have at least one or any combination of the following properties (a) to (c).

(a) Acceptor Substrate Specificity

When using an oligosaccharide as an acceptor substrate, the enzyme protein shows transferase activity toward Bz-β-GlcNAc, GlcNAc-β1-4-GlcNAc-β-Bz, Gal-β1-3 (GlcNAc-β1-6) GalNAc-α-pNp, GlcNAc-β1-3 GalNAc-α-pNp and GlcNAc-β1-6GalNAc-α-pNp ("GlcNAc" represents an N-acetyl-D-glucosamine residue, "GalNAc" represents an N-acetyl-D-galactosamine residue, "Bz" represents a benzyl group, "pNp" represents a p-nitrophenyl group, and "–" represents a glycosidic linkage. Numbers in these formulae each represent the carbon number in the sugar ring where a glycosidic linkage is present, and "α" and "β" represent anomers of the glycosidic linkage at the 1-position of the sugar ring. An anomer whose positional relationship with $CH_2OH$ or $CH_3$ at the 5-position is trans and cis is represented by "α" and "β", respectively).

Preferably, the enzyme protein is substantially free from transferase activity toward Bz-α-GlcNAc and Gal β1-3 GlcNAc-β-pNp.

(b) Reaction pH

The activity is lower in a pH range of 6.2 to 6.6 than in other pH ranges.

(c) Divalent ion Requirement

Although the above activity is enhanced at least in the presence of $Mn^{2+}$, $Co^{2+}$ or $Mg^{2+}$, the $Mn^{2+}$-induced enhancement of the activity is almost completely eliminated in the presence of $Cu^{2+}$.

Moreover, in a preferred embodiment of the above glycosyltransferase protein, the glycosyltransferase protein of the present invention comprises the following polypeptide (A) or (B):

(A) a polypeptide which has the amino acid sequence shown in SEQ ID NO: 2 or 4; or (B) a polypeptide which has an amino acid sequence with substitution, deletion or insertion of one or more amino acids in the amino acid sequence shown in SEQ ID NO: 2 or 4 and which transfers N-acetyl-D-galactosamine to N-acetyl-D-glucosamine with β1,3 linkage.

Moreover, in a more preferred embodiment of the above glycosyltransferase protein, the above polypeptide (A) is a glycosyltransferase protein consisting of a polypeptide having an amino acid sequence covering amino acids 189 to 500 shown in SEQ ID NO: 2. Likewise, in an even more preferred embodiment of the above glycosyltransferase protein, the above polypeptide (A) is a glycosyltransferase protein consisting of a polypeptide having an amino acid sequence covering amino acids 36 to 500 shown in SEQ ID NO: 2.

In addition, other embodiments of the glycosyltransferase protein of the present invention encompass proteins consisting of polypeptides having amino acid sequences sharing at least more than 30% identity, preferably at least 40% identity, and more preferably at least 50% identity with an amino acid sequence covering amino acids 189 to 500 shown in SEQ ID NO: 2 or amino acids 35 to 504 shown in SEQ ID NO: 4.

In another aspect, the present invention provides a nucleic acid consisting of a nucleotide sequence encoding any one of the above polypeptides or a nucleotide sequence complementary thereto.

In a preferred embodiment, the nucleic acid encoding the protein of the present invention is a nucleic acid consisting of the nucleotide sequence shown in SEQ ID NO: 1 or 3 or a nucleotide sequence complementary to at least one of them. More preferably, in the case of human origin, such a nucleic acid consists of a nucleotide sequence covering nucleotides 565 to 1503 shown in SEQ ID NO: 1 or a nucleotide sequence complementary thereto, and most preferably consists of a nucleotide sequence covering nucleotides 106 to 1503 shown in SEQ ID NO: 1 or a nucleotide sequence complementary thereto. In the case of mouse origin, such a nucleic acid consists of a nucleotide sequence covering nucleotides 103 to 1512 shown in SEQ ID NO: 3 or a nucleotide sequence complementary thereto.

Embodiments of the above nucleic acids according to the present invention encompass DNA.

The present invention further provides a vector carrying any one of the above nucleic acids and a transformant containing the vector.

In yet another aspect, the present invention provides a method for producing a β1,3-N-acetyl-D-galactosaminyltransferase protein, which comprises growing the above transformant to express the above glycosyltransferase protein and collecting the glycosyltransferase protein from the grown transformant.

In yet another aspect, the present invention provides an antibody recognizing any one of the above β1,3-N-acetyl-D-galactosaminyltransferase proteins.

On the other hand, in response to the discovery of the above G34, the inventors of the present invention have clarified that the expression level of G34 mRNA is increased significantly in cancerous tissues and cell lines.

Thus, the present invention also provides a nucleic acid for measurement, which is useful as an index of canceration or malignancy and which hybridizes under stringent conditions to the nucleotide sequence shown in SEQ ID NO: 1 or 3 or a nucleotide sequence complementary to at least one of them.

The nucleic acid for measurement of the present invention may typically consist of a nucleotide sequence covering at least a dozen contiguous nucleotides in the nucleotide sequence shown in SEQ ID NO: 1 or 3 or a nucleotide sequence complementary thereto.

In a preferred embodiment, the nucleic acid for measurement of the present invention encompasses a probe consisting of the nucleotide sequence shown in SEQ ID NO: 16 or a nucleotide sequence complementary thereto, as well as a primer set consisting of the following nucleotide sequences (1) or (2):
(1) a pair of the nucleotide sequences shown in SEQ ID NOs: 14 and 15; or
(2) a pair of the nucleotide sequences shown in SEQ ID NOs: 17 and 18.

Also, the nucleic acid for measurement of the present invention may be used as a tumor marker.

The present invention further provides a method for assaying canceration in a biological sample, which comprises:
(a) using any one of the above nucleic acids to measure the transcription level of the nucleic acid in the biological sample; and
(b) determining whether the measured value is significantly higher than that of a normal biological sample.

In a preferred embodiment, the canceration assay of the present invention includes cases where the measurement of the transcription level is made by hybridization or PCR targeted at the above biological sample and using any one of the above nucleic acids.

In a further aspect of the canceration assay of the present invention, the present invention provides a method for assaying the effectiveness of treatment in cancer therapy, which comprises using any one of the above nucleic acids to measure the transcription level of the nucleic acid in a biological sample treated by cancer therapy, and determining whether the measured value is significantly lower than that obtained before treatment or than that of an untreated sample.

In particular, the above biological sample may be derived from the large intestine (colon) or lung.

MODE FOR CARRYING OUT THE INVENTION

The mode for carrying out the present invention will be described in detail below.
(1) Nucleic Acid Encoding the G34 Enzyme Protein of the Present Invention Based upon the above discovery, the inventors of the present invention expressed the G34 enzyme protein encoded by the nucleic acid, isolated and purified the protein, and further identified its enzymatic activity. When focusing on the fact that an amino acid sequence having the desired enzymatic activity was identified, the nucleotide sequence of SEQ ID NO: 1 or 3 is one embodiment of a nucleic acid encoding the isolated polypeptide having the enzymatic activity. This means that the nucleic acid of the present invention encompasses all, but a limited number of, nucleic acids having degenerate nucleotide sequences capable of encoding the same amino acid sequence for the G34 enzyme protein.

The present invention also provides a nucleic acid encoding the full-length or a fragment of a polypeptide consisting of a novel amino acid sequence as mentioned above. A typical nucleic acid encoding such a novel polypeptide may have the nucleotide sequence shown in SEQ ID NO: 1 or 3 or a nucleotide sequence complementary to at least one of them.

The nucleic acid of the present invention also encompasses both single-stranded and double-stranded DNA and their complementary RNA. Examples of DNA include naturally-occurring DNA, recombinant DNA, chemically-bound DNA, PCR-amplified DNA, and combinations thereof. However, DNA is preferred in terms of stability during vector and/or transformant preparation.

The nucleic acid of the present invention may be prepared in the following manner, by way of example.

First, the known sequence under GenBank No. AX285201 or a part thereof may be used to perform nucleic acid amplification on a cDNA library in a routine manner using basic procedures for genetic engineering (e.g., hybridization, nucleic acid amplification), thereby cloning the nucleic acid of the present invention. Since the nucleic acid may be obtained, e.g., as a DNA fragment of approximately 1.5 kbp as a PCR product, the fragment may be separated using techniques for screening DNA fragments based on their molecular weight (e.g., agarose gel electrophoresis) and isolated in a routine manner, e.g. using techniques for excising a specific band.

Moreover, according to the putative amino acid sequence (SEQ ID NO: 2 or 4) of the isolated nucleic acid, the nucleic acid may be estimated to have a hydrophobic transmembrane region at its N-terminal end. By preparing a region of a nucleotide sequence encoding a polypeptide free from this transmembrane region, it is also possible to obtain the nucleic acid of the present invention that encodes a soluble form of the polypeptide.

Based on the nucleotide sequence of the nucleic acid disclosed herein, it is easy for those skilled in the art to create appropriate primers from nucleotide sequences located at both ends of a nucleic acid of interest or a region thereof to be prepared and to use the primers thus created for nucleic acid amplification to amplify and prepare the region of interest.

The above nucleic acid amplification includes, for example, reactions requiring thermal cycling such as polymerase chain reaction (PCR) [Saiki R. K., et al., Science, 230, 1350-1354 (1985)], ligase chain reaction (LCR) [Wu D. Y., et al., Genomics, 4, 560-569 (1989); Barringer K. J., et al., Gene, 89, 117-122 (1990); Barany F., Proc. Natl. Acad. Sci. USA, 88, 189-193 (1991)] and transcription-based amplification [Kwoh D. Y., et al., Proc. Natl. Acad. Sci. USA, 86, 1173-1177 (1989)], as well as isothermal reactions such as strand displacement amplification (SDA) [Walker G. T., et al., Proc. Natl. Acad. Sci. USA, 89, 392-396 (1992); Walker G. T., et al., Nuc. Acids Res., 20, 1691-1696 (1992)], self-sustained sequence replication (3SR) [Guatelli J. C., Proc. Natl. Acad. Sci. USA, 87, 1874-1878 (1990)] and Qβ replicase system [Lizardi et al., BioTechnology 6, p. 1197-1202 (1988)]. It is also possible to use other reactions, e.g., nucleic acid sequence-based amplification (NASBA) through competitive amplification between a target nucleic acid and a mutated sequence, found in European Patent No. 0525882. Preferred is PCR.

The use of the nucleic acid of the present invention also enables the expression of the intended enzyme protein or the provision of probes and antisense primers for the purpose of medical research or gene therapy, as described later.

Those skilled in the art will be able to obtain a nucleic acid as useful as the sequence of SEQ ID NO: 1 or 3 by preparing a nucleic acid consisting of a nucleotide sequence sharing a certain homology with the nucleotide sequence of SEQ ID NO: 1 or 3. For example, the homologous nucleic acid of the present invention encompasses nucleic acids encoding proteins which share homology with the amino acid sequence shown in SEQ ID NO: 2 or 4 and which have the ability to transfer N-acetyl-D-galactosamine to N-acetyl-D-glucosamine with β1,3 linkage.

To identify the range of nucleic acids encoding such homologous proteins according to the present invention, an identity search is performed for the nucleic acid sequence shown in SEQ ID NO: 1 or 3 of the present invention, indicating that the nucleic acid sequence shares 40% identity with the nucleic acid sequence of a known β1,4GalNAc transferase showing the highest homology (Non-patent Document 1 listed above) and also shares 40% identity with the nucleic acid sequence of a known β1,3Gal transferase showing the highest homology (Non-patent Document 2 listed above). In light of these points, a preferred nucleic acid sequence encoding the homologous protein of the present invention typically shares more than 40% identity, more preferably at least 50% identity, and particularly preferably at least 60% identity with any one of the entire nucleotide sequence of SEQ ID NO: 1 or 3, preferably a partial nucleotide sequence consisting of nucleotides 106 to 1503 in SEQ ID NO: 1, preferably a partial nucleotide sequence consisting of nucleotides 103 to 1512 in SEQ ID NO: 3, or nucleotide sequences complementary to these sequences.

Likewise, the nucleotide sequences shown in SEQ ID NOs: 1 and 3 share 86% identity with each other. In light of this point, a preferred nucleic acid sequence encoding the homologous protein of the present invention can be defined as sharing at least 86%, preferably 90% identity with any one of the entire nucleotide sequence of SEQ ID NO: 1, preferably nucleotides 106 to 1503, or a nucleotide sequence complementary thereto.

The above percentage of identity may be determined by visual inspection and mathematical calculation. Alternatively, the percentage of identity between two nucleic acid sequences may be determined by comparing sequence information using the GAP computer program, version 6.0, described by Devereux et al., Nucl. Acids Res. 12: 387, 1984 and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, pp. 353-358, National Biomedical Research Foundation, 1979; (2) a penalty of 3.0 for each gap and an additional 0.10 penalty for each symbol in each gap; and (3) no penalty for end caps. It is also possible to use other sequence comparison programs used by those skilled in the art.

Other nucleic acids homologous as the structural gene of the present invention typically include nucleic acids which hybridize under stringent conditions to a nucleotide consisting of a nucleotide sequence within SEQ ID NO: 1 or 3, preferably a nucleotide sequence consisting of nucleotides 106 to 1503 of SEQ ID NO: 1, preferably a nucleotide sequence consisting of nucleotides 103 to 1512 of SEQ ID NO: 3, or a nucleotide sequence complementary thereto and which encode polypeptides having the ability to transfer N-acetyl-D-galactosamine to N-acetyl-D-glucosamine with β1,3 linkage.

As used herein, "under stringent conditions" means that a nucleic acid hybridizes under conditions of moderate or high stringency. More specifically, conditions of moderate stringency may readily be determined by those having ordinary skill in the art, e.g., depending on the length of DNA. Primary conditions can be found in Sambrook et al., Molecular Cloning: A Laboratory Manual, 3rd edition, Vol. 1, 7.42-7.45 Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of about 60° C., 0.5×SSC, 0.1% SDS. Conditions of high stringency can also be readily determined by those skilled in the art, e.g., depending on the length of DNA. In general, such conditions include hybridization and/or washing at a higher temperature and/or at a lower salt concentration than that required under conditions of moderate stringency and, for example, are defined as hybridization conditions as above and with washing at about 68° C., 0.2× SSC, 0.1% SDS. Those skilled in the art will recognize that the temperature and washing solution salt concentration can be adjusted as necessary according to factors such as the length of nucleotide sequences.

As described above, those skilled in the art will readily determine and achieve conditions of suitably moderate or high stringency on the basis of common knowledge about hybridization conditions which are known in the art, as well as on the empirical rule which will be obtained through commonly used experimental means.

(2) Vector and Transformant of the Present Invention

The present invention provides a recombinant vector carrying the above nucleic acid. Procedures for integrating a DNA fragment of the nucleic acid into a vector (e.g., a plasmid) include those described in Sambrook, J. et al., Molecular Cloning, A Laboratory Manual (3rd edition), Cold Spring Harbor Laboratory, 1.1 (2001). For convenience, a commercially available ligation kit (e.g., a product of TaKaRa Shuzo Co., Ltd., Japan) may be used.

The recombinant vector (e.g., recombinant plasmid) thus obtained may be introduced into host cells (e.g., *E. coli* DH5α, TB1, LE392, or XL-LE392 or XL-1Blue). Procedures for introducing the plasmid into host cells include those described in Sambrook, J. et al., Molecular Cloning, A Laboratory Manual (3rd edition), Cold Spring Harbor Laboratory, 16.1 (2001), exemplified by the calcium chloride method or the calcium chloride/rubidium chloride method, electroporation, electroinjection, chemical treatment (e.g., PEG treatment), and the gene gun method.

A vector which can be used may be prepared readily by linking a desired gene to a recombination vector available in the art (e.g., plasmid DNA) in a routine manner. Specific examples of a vector to be used include, but are not limited to, *E. coli*-derived plasmids such as pDONR201, pBluescript, pUC18, pUC19 and pBR322.

Those skilled in the art will be able to select appropriate restriction ends to fit into the intended expression vector. The expression vector may be selected appropriately by those skilled in the art such that the vector is suitable for host cells where the enzyme of the present invention is to be expressed. Moreover, the expression vector is preferably constructed to allow regions involved in gene expression (e.g., promoter region, enhancer region and operator region) to be properly located to ensure expression of the above nucleic acid in target host cells, so that the nucleic acid is properly expressed.

The type of expression vector is not limited in any way as long as the vector allows expression of a desired gene in various prokaryotic and/or eukaryotic host cells and has the function of producing a desired protein. Preferred examples include pQE-30, pQE-60, pMAL-C2, pMAL-p2 and pSE420 for *E. coli* expression, pYES2 (*Saccharomyces*) and pPIC3.5K, pPIC9K and pA0815 (all *Pichia*) for yeast expression, as well as pFastBac, pBacPAK8/9, pBK283, pVL1392 and pBlueBac4.5 for insect expression.

To construct the expression vector, a Gateway system (Invitrogen Corporation) may be used which does not require restriction treatment and ligation operation. The Gateway system is a site-specific recombination system which allows cloning while maintaining the orientation of PCR products and also allows subcloning of a DNA fragment into a properly modified expression vector. More specifically, this system prepares an expression clone corresponding to the intended expression system by creating an entry clone from a PCR product and a donor vector by the action of a site-specific recombinase BP clonase and then transferring the PCR product to a destination vector which allows recombination with this clone by the action of another recombinase LR clonase. One feature of this system is that a time- and labor-consuming subcloning step which requires treatment with restriction enzymes and/or ligases can be eliminated when an entry clone is created to begin with.

The above expression vector carrying the nucleic acid of the present invention may be integrated into host cells to give a transformant for producing the polypeptide of the present invention. In general, host cells used for obtaining the transformant may be either eukaryotic cells (e.g., mammalian cells, yeast, insect cells) or prokaryotic cells (e.g., *E. coli*, *Bacillus subtilis*). Also, cultured cells of human origin (e.g., HeLa, 293T, SH-SY5Y) or mouse origin (e.g., Neuro2a, NIH3T3) may be used for this purpose. All of these host cells are known and commercially available (e.g., from Dainippon Pharmaceutical Co., Ltd., Japan), or available from public research institutions (e.g., RIKEN Cell Bank). Alternatively, it is also possible to use embryos, organs, tissues or non-human individuals.

Since the nucleic acid of the present invention was found from human genome libraries, it is believed that when eukaryotic cells are used as host cells, the G34 enzyme protein of the present invention may have properties close to native proteins (e.g., embodiments where glycosylation occurs). In light of this point, it is preferable to select eukaryotic cells, particularly mammalian cells, as host cells. Specific examples of mammalian cells include animal cells of mouse, *Xenopus laevis*, rat, hamster, monkey or human origin or cultured cell lines established from these cells. *E. coli*, yeast or insect cells available for use as host cells are specifically exemplified by *E. coli* (e.g., DH5α, M15, JM109, BL21), yeast (e.g., INVSc1 (*Saccharomyces*), GS115, KM71 (both *Pichia*)) or insect cells (e.g., Sf21, BmN4, silkworm larva).

In general, an expression vector can be prepared by linking at least a promoter, an initiation codon, a gene encoding a desired protein, a termination codon and a terminator region to an appropriate replicable unit to give a continuous loop. In this case, if desired, it is also possible to use an appropriate DNA fragment (e.g., linkers, other restriction enzyme sites) through routine techniques such as digestion with a restriction enzyme and/or ligation using T4 DNA ligase. When bacterial (particularly *E. coli*) cells are used as host cells, an expression vector is generally composed of at least a promoter/operator region, an initiation codon, a gene encoding a desired protein, a termination codon, a terminator and a replicable unit. When yeast cells, plant cells, animal cells or insect cells are used as host cells, it is generally preferred that an expression vector comprises at least a promoter, an initiation codon, a gene encoding a desired protein, a termination codon and a terminator. In this case, the vector may also comprise DNA encoding a signal peptide, an enhancer sequence, 5'- and 3'-terminal untranslated regions of the desired gene, a selective marker region or a replicable unit, as appropriate.

A replicable unit refers to DNA having the ability to replicate its entire DNA sequence in host cells and includes a native plasmid, an artificially modified plasmid (i.e., a plasmid prepared from a native plasmid) and a synthetic plasmid. Examples of a preferred plasmid include plasmid pQE30, pET or pCAL or an artificially modified product thereof (i.e., a DNA fragment obtained from pQE30, pET or pCAL by treatment with an appropriate restriction enzyme) for *E. coli* cells, plasmid pYES2 or pPIC9K for yeast cells, as well as plasmid pBacPAK8/9 for insect cells.

A methionine codon (ATG) may be given as an example of an initiation codon preferred for the vector of the present invention. Examples of a termination codon include commonly used termination codons (e.g., TAG, TGA, TAA). As for enhancer and terminator sequences, it is also possible to use those commonly used by those skilled in the art, such as SV40-derived enhancer and terminator sequences.

As a selective marker, a commonly used one can be used in a routine manner. Examples include antibiotic resistance genes such as those resistant to tetracycline, ampicillin, or kanamycin or neomycin, hygromycin or spectinomycin.

The introduction (also referred to as transformation or transfection) of the expression vector according to the present invention into host cells may be accomplished by using conventionally known techniques. Transformation may be accomplished, for example, by the method of Cohen et al. [Proc. Natl. Acad. Sci. USA, 69, 2110 (1972)], the protoplast method [Mol. Gen. Genet., 168, 111 (1979)] or the competent method [J. Mol. Biol., 56, 209 (1971)] for bacterial cells (e.g., *E. coli, Bacillus subtilis*) and by the method of Hinnen et al. [Proc. Natl. Acad. Sci. USA, 75, 1927 (1978)] or the lithium method [J. B. Bacteriol., 153, 163 (1983)] for *Saccharomyces cerevisiae*. Transformation may also be accomplished, for example, by the leaf disk method [Science, 227, 129 (1985)] or electroporation [Nature, 319, 791 (1986)] for plant cells, by the method of Graham et al. [Virology, 52, 456 (1973)] for animal cells, and by the method of Summer et al. [Mol. Cell Biol., 3, 2156-2165 (1983)] for insect cells.

(3) G34 Enzyme Protein of the Present Invention

As illustrated in the Example section described later, a polypeptide having a novel enzymatic activity can be isolated and purified, for example, by integrating a nucleic acid having the nucleotide sequence of SEQ ID NO: 1 or 3 into an expression vector and then expressing the nucleic acid.

First, in light of the above point, a typical embodiment of the protein of the present invention is an isolated G34 enzyme protein consisting of the putative amino acid sequence shown in SEQ ID NO: 2 or 4. More specifically, this enzyme protein has the activities shown below.

Catalytic Reaction

The enzyme protein allows transfer of "N-acetyl-D-galactosamine (GalNAc)" from its donor substrate to an acceptor substrate containing "N-acetyl-D-glucosamine (GlcNAc)." Examination of motif sequences in the amino acid sequence indicates that the linking mode between N-acetylgalactosamine and N-acetylglucosamine is a β1,3 glycosidic linkage (see Example 2).

Donor Substrate Specificity:

The above N-acetyl-D-galactosamine donor substrate encompasses sugar nucleotides having N-acetylgalactosamine, such as uridine diphosphate-N-acetylgalactosamine (UDP-GalNAc), adenosine diphosphate-N-galactosamine (ADP-GalNAc), guanosine diphosphate-N-acetylgalactosamine (GDP-GalNAc) and cytidine diphosphate-N-acetylgalactosamine (CDP-GalNAc). A typical donor substrate is UDP-GalNAc.

Namely, the G34 enzyme protein of the present invention catalyzes a reaction of the following scheme:

UDP-GalNAc+GlcNAc-R→UDP+GalNAc-(β1,3-GlcNAc-R (wherein R represents, e.g., a glycoprotein, glycolipid, oligosaccharide or polysaccharide having the GlcNAc residue).

Acceptor Substrate Specificity:

An acceptor substrate of the above GalNAc is N-acetyl-D-glucosamine, typically an N-acetyl-D-glucosamine residue of glycoproteins, glycolipids, oligosaccharides or polysaccharides, etc.

When using an oligosaccharide as an acceptor substrate, the human G34 protein obtained in Example 1 described later (typically having a region covering amino acid 36 to the C-terminal end of SEQ ID NO: 2) shows, transferase activity toward Bz-β-GlcNAc, GlcNAc-β1-4-GlcNAc-β-Bz, pNp-core2 (core2=Gal-β1-3-(GlcNAc-(β1-6) GalNAc-α-pNp; the same applying hereinafter), pNp-core3 (core3=GlcNAc-(β1-3 GalNAc-α-pNp; the same applying hereinafter) and pNp-core6 (core6=GlcNAc-β1-6-GalNAc-α-pNp; the same applying hereinafter). Preferably, the human G34 protein is free from transferase activity toward Bz-α-GlcNAc and Gal-β1-3 GlcNAc-β-pNp. Moreover, when the activity is compared between these substrates, the transferase activity is very high in transferring to pNp-core2 and Bz-β-GlcNAc, particularly highest in transferring to pNp-core2. The transferase activity is relatively low in transferring to GlcNAc-β1-4-GlcNAc-β-Bz, pNp-core3 and pNp-core6.

Likewise, the mouse G34 protein obtained in Example 4 described later (typically having an active region covering amino acid 35 to the C-terminal end of SEQ ID NO: 4) shows transferase activity toward Bz-β-GlcNAc, pNp-β-Glc, GlcNAc-β1-4-GlcNAc-β-Bz, pNp-core2, pNp-core3 and pNp-core6. When the activity is compared between these substrates, the transferase activity is highest in transferring to Bz-β-GlcNAc, followed by core2-pNp, core6-pNp, core3-pNp, pNp-β-Glc and GlcNAc-β1-4-GlcNAc-β-Bz in the order named.

As used herein, "GlcNAc" represents an N-acetyl-D-glucosamine residue, "GalNAc" represents an N-acetyl-D-galactosamine residue, "Glc" represents a glucosamine residue, "Bz" represents a benzyl group, "pNp" represents a p-nitrophenyl group, "oNp" represents a o-nitrophenyl group, and "–" represents a glycosidic linkage. Numbers in these formulae each represent the carbon number in the sugar ring where the above glycosidic linkage is present. Likewise, "α" and "β" represent anomers of the above glycosidic linkage at the 1-position of the sugar ring. An anomer whose positional relationship with $CH_2OH$ or $CH_3$ at the 5-position is trans and cis is represented by "α" and "β", respectively.

Optimum Buffer and Optimum pH (Table 3 and FIG. 4):

Examination of the human G34 protein indicates that the protein has the above catalytic effect in each of the following optimum buffers: MES (2-morpholinoethanesulfonic acid) buffer, sodium cacodylate buffer or HEPES (N-[2-hydroxyethyl]piperazine-N'-[2-ethanesulfonic acid]) buffer.

The pH dependence of the activity in each buffer is as follows: in MES buffer, the activity is highest around a pH of at least 5.50 to 5.78 and second highest around pH 6.75; in sodium cacodylate buffer, the activity increases with decrease in pH from around 6.2 to around 5.0 and is highest around pH 5.0, while the activity also increases in a pH-dependent manner between around pH 6.2 and 7.0 and nearly plateaus around pH 7.4; and in HEPES buffer, the activity is highest around a pH of 7.4 to 7.5. Among them, HEPES buffer at a pH of about 7.4 to about 7.5 results in the strongest activity. In all the buffers, the activity is lower in a pH range of 6.2 to 6.6 than in other pH ranges.

Divalent Ion Requirement (Table 4 and FIG. 5):

The activity of the human G34 protein is enhanced in the presence of a divalent metal ion, particularly $Mn^{2+}$, $Co^{2+}$ or $Mg^{2+}$. The influence of each metal ion concentration on the activity is as follows: in the case of $Mn^{2+}$ and $Co^{2+}$, the activity increases in a concentration-dependent manner up to around 5.0 nM and then nearly plateaus at higher concentrations, while in the case of $Mg^{2+}$, the activity increases in a concentration-dependent manner up to around 2.5 nM and then nearly plateaus at higher concentrations. However, the $Mn^{2+}$-induced enhancement of the activity is completely eliminated in the presence of $Cu^{2+}$.

As described above, the G34 enzyme protein of the present invention can transfer a GalNAc residue to a GlcNAc residue with (β1-3 glycosidic linkage under given enzymatic reaction conditions as mentioned above and is useful for such sugar chain synthesis or modification reactions targeted at glycoproteins, glycolipids, oligosaccharides or polysaccharides, etc.

Secondly, having disclosed herein the amino acid sequences shown in SEQ ID NOs: 2 and 4 which are given as typical examples of the primary structure of the above enzyme protein, the present invention provides all proteins which can be produced on the basis of these amino acid sequences through genetic engineering procedures well known in the art (hereinafter also referred to as "mutated proteins" or "modified proteins"). Namely, according to common knowledge in the art, the enzyme protein of the present invention is not limited only to a protein consisting of the amino acid sequence of SEQ ID NO: 2 or 4 estimated from the nucleotide sequence of each cloned nucleic acid, and is also intended to include, for example, a protein consisting of a non-full-length polypeptide having, e.g., a partial N-terminal deletion of the amino acid sequence, or a protein homologous to such an amino acid sequence, each of which has properties inherent to the protein, as illustrated below.

First, the human G34 enzyme protein of the present invention may preferably have an amino acid sequence covering amino acid 189 to the C-terminal end of SEQ ID NO: 2, more preferably an amino acid sequence covering amino acid 36 to the C-terminal end as obtained in the Example section described later. Likewise, the mouse G34 enzyme protein of the present invention may preferably have an amino acid sequence covering amino acid 35 to the C-terminal end of SEQ ID NO: 4.

Moreover, in proteins usually having physiological activities equivalent to enzymes, it is well known that the physiological activities are maintained even when their amino acid sequences have substitution, deletion, insertion or addition of one or more amino acids. It is also known that among naturally-occurring proteins, there are mutated proteins which have gene mutations resulting from differences in the species of source organisms and/or differences in ecotype or which have one or more amino acid mutations resulting from the presence of closely resembling isozymes, etc. In light of this point, the protein of the present invention also encompasses mutated proteins which have an amino acid sequence with substitution, deletion, insertion or addition of one or more amino acids in each amino acid sequence shown in SEQ ID NO: 2 or 4 and which have the ability to transfer a GalNAc residue to a GlcNAc residue with β1-3 glycosidic linkage under given enzymatic reaction conditions as mentioned above. Moreover, particularly preferred are modified proteins having amino acid sequences with substitution, deletion, insertion or addition of one or several amino acids in each amino acid sequence shown in SEQ ID NO: 2 or 4.

The expression "one or more amino acids" found above means preferably 1 to 200 amino acids, more preferably 1 to 100 amino acids, even more preferably 1 to 50 amino acids, and most preferably 1 to 20 amino acids. In general, in a case where amino acid substitution occurs as a result of site-specific mutagenesis, the number of amino acids which can be substituted while maintaining the activities inherent to the original protein is preferably 1 to 10.

The modified protein of the present invention also includes those obtained by substitution between functionally equivalent amino acids. Namely, it is generally well known to those skilled in the art that recombinant proteins having a desired mutation(s) can be prepared by procedures involving introduction of substitution between functionally equivalent amino acids (e.g., replacement of one hydrophobic amino acid with another hydrophobic amino acid, replacement of one hydrophilic amino acid with another hydrophilic amino acid, replacement of one acidic amino acid with another acidic amino acid, or replacement of one basic amino acid with another basic amino acid). The modified proteins thus obtained often have the same properties as the original protein. In light of this point, modified proteins having such amino acid substitutions also fall within the scope of the present invention.

Moreover, the modified protein of the present invention may be a glycoprotein having sugar chains attached to the polypeptide as long as it has such an amino acid sequence as defined above and has an enzymatic activity inherent to the intended enzyme.

To identify the range of the homologous protein of the present invention, an identity search using GENETYX software (Genetyx Corporation, Japan) is performed for the amino acid sequence shown in SEQ ID NO: 2 or 4 of the present invention, indicating that the amino acid sequence shares 14% identity with a known β1,4GalNAc transferase showing the highest homology (Non-patent Document 1 listed above) and also shares 30% identity with a known β1,3Gal transferase showing the highest homology (Non-patent Document 2 listed above). In light of these points, a preferred amino acid sequence for the homologous protein of the present invention preferably shares more than 30% identity, more preferably at least 40% identity, and particularly preferably at least 50% identity with the amino acid sequence shown in SEQ ID NO: 2 or 4.

Likewise, the amino acid sequences shown in SEQ ID NOs: 2 and 4 share 88% identity with each other. In light of this point, a preferred amino acid sequence for the homologous protein of the present invention can be defined as sharing at least 88%, more preferably 90% identity with the amino acid sequence within SEQ ID NO: 2.

The above GENETYX is genetic information processing software for nucleic acid/protein analysis and enables standard analyses of homology and multialignment, as well as signal peptide prediction, promoter site prediction and secondary structure prediction. The homology analysis program used herein employs the Lipman-Pearson method (Lipman, D.J. & Pearson, W.R., Science, 277, 1435-1441 (1985)) frequently used as a rapid and sensitive method. In the present invention, the percentage of identity may be determined by comparing sequence information using, e.g., the BLAST program described by Altschul et al. (Nucl. Acids. Res., 25. 3389-3402 (1997)) or the FASTA program described by Pearson et al. (Proc. Natl. Acad. Sci. USA, 2444-2448 (1988)). These programs are available on the Internet at the web site of the National Center for Biotechnology Information (NCBI) or the DNA Data Bank of Japan (DDBJ). The details of various conditions (parameters) for each identity search using each program are shown on these web sites, and default values are commonly used for these searches although part of the settings may be changed as appropriate. It is also possible to use other sequence comparison programs used by those skilled in the art.

Thirdly, the isolated protein of the present invention may be administered as an immunogen to an animal to produce an antibody against the protein, as described later. Such an antibody may be used for immunoassays to measure and quantify the enzyme. Thus, the present invention is also useful in preparing such an immunogen. In light of this point, the protein of the present invention also includes a polypeptide fragment, mutant or fusion protein thereof, which contains an antigenic determinant or epitope for eliciting antibody formation.

(4) Isolation and Purification of the G34 Enzyme Protein of the Present Invention The enzyme protein of the present invention may be isolated and purified in the following manner.

Recent studies have established genetic engineering procedures which involve culturing and growing a transformant and isolating and purifying a substance of interest from the resulting culture or grown transformant. The enzyme protein of the present invention may also be expressed (produced), e.g., by culturing in a nutrient medium a transformant containing an expression vector carrying the nucleic acid of the present invention.

A nutrient medium used for transformant culturing preferably contains a carbon source, an inorganic nitrogen source or an organic nitrogen source required for host cell (transformant) growth. Examples of a carbon source include glucose, dextran, soluble starch, sucrose and methanol. Examples of an inorganic or organic nitrogen source include ammonium salts, nitrate salts, amino acids, corn steep liquor, peptone, casein, meat extracts, soybean meal and potato extracts. If desired, the medium may contain other nutrients such as inorganic salts (e.g., sodium chloride, calcium chloride, sodium dihydrogen phosphate, magnesium chloride), vitamins, and antibiotics (e.g., tetracycline, neomycin, ampicillin, kanamycin). Culturing may be accomplished in a manner known in the art. Culture conditions such as temperature, medium pH and culture period may be appropriately selected such that the protein according to the present invention is produced in a large quantity.

The enzyme protein of the present invention may be obtained from the above culture or grown transformant as follows. Namely, in a case where a protein of interest is accumulated in host cells, the host cells may be collected by manipulations such as centrifugation or filtration, suspended in an appropriate buffer (e.g., Tris buffer, phosphate buffer, HEPES buffer or MES buffer at a concentration around 10 to 100 mM, the pH of which will vary from buffer to buffer, but desirably falls within the range of 5.0 to 9.0), and then crushed in a manner suitable for the host cells used, followed by centrifugation to obtain the contents of the host cells. On the other hand, in a case where a protein of interest is secreted from host cells, the host cells and the medium are separated from each other by manipulations such as centrifugation or filtration to obtain a culture filtrate. The crushed host cell solution or culture filtrate may be provided directly or may be treated by ammonium sulfate precipitation and dialysis before being provided for isolation and purification of the protein.

Isolation and purification of a protein of interest may be accomplished in the following manner. Namely, in a case where the protein is labeled with a tag such as 6× histidine, GST or maltose-binding protein, the isolation and purification may be accomplished by affinity chromatography suitable for each of the commonly used tags. On the other hand, in a case where the protein according to the present invention is produced without being labeled with such a tag, the isolation and purification may be accomplished, e.g., by ion exchange chromatography, which may further be combined with gel filtration, hydrophobic chromatography, isoelectric chromatography, etc.

Moreover, an expression vector may be constructed to facilitate isolation and purification. In particular, the isolation and purification is facilitated if an expression vector is constructed to express a fusion protein of a polypeptide having an enzymatic activity with a labeling peptide and the enzyme protein is prepared in a genetic engineering manner. An example of the above identification peptide is a peptide having the function of facilitating secretion, separation, purification or detection of the enzyme according to the present invention from the grown transformant by allowing the enzyme to be expressed as a fusion protein in which the identification peptide is attached to a polypeptide having an enzymatic activity when the enzyme according to the present invention is prepared by gene recombination techniques.

Examples of such an identification peptide include peptides such as a signal peptide (a peptide composed of 15 to 30 amino acid residues, which is present at the N-terminal end of many proteins and is functional in cells for protein selection in the intracellular membrane permeation mechanism; e.g., OmpA, OmpT, Dsb), protein kinase A, Protein A (a protein with a molecular weight of about 42,000, which is a component constituting the *Staphylococcus aureus* cell wall), glutathione S transferase, His tag (a sequence consisting of 6 to 10 histidine residues in series), myc tag (a 13 amino acid sequence derived from cMyc protein), FLAG peptide (an analysis marker composed of 8 amino acid residues), T7 tag (composed of the first 11 amino acid residues of the gene 10 protein), S tag (composed of pancreas RNase A-derived 15 amino acid residues), HSV tag, pelB (a 22 amino acid sequence from the *E. coli* external membrane protein pelB), HA tag (composed of hemagglutinin-derived 10 amino acid residues), Trx tag (thioredoxin sequence), CBP tag (calmodulin-binding peptide), CBD tag (cellulose-binding domain), CBR tag (collagen-binding domain), β-lac/blu (β-lactamase), β-gal (β-galactosidase), luc (luciferase), HP-Thio (His-patch thioredoxin), HSP (heat shock peptide), Lnγ (laminfn γ-peptide), Fn (fibronectin partial peptide), GFP (green fluorescent peptide), YFP (yellow fluorescent peptide), CFP (cyan fluorescent peptide), BFP (blue fluorescent peptide), DsRed, DsRed2 (red fluorescent peptides), MBP (maltose-binding peptide), LacZ (lactose operator), IgG (immunoglobulin G), avidin and Protein G, any of which can be used.

Among them, particularly preferred are the signal peptide, protein kinase A, Protein A, glutathione S transferase, His tag, myc tag, FLAG peptide, T7 tag, S tag, HSV tag, pelB and HA tag because they facilitate expression and purification of the enzyme according to the present invention through genetic engineering procedures. In particular, it is preferable to obtain the enzyme as a fusion protein with FLAG peptide (Asp-Tyr-Lys-Asp-Asp-Asp-Asp-Lys) because it is very easy to handle. The above FLAG peptide is extremely antigenic and provides an epitope capable of reversible binding of a specific monoclonal antibody, thus enabling rapid assay and easy purification of the expressed recombinant protein. A mouse hybridoma called 4E11 produces a monoclonal antibody which binds to FLAG peptide in the presence of a certain divalent metal cation, as described in U.S. Pat. No. 5,011,912 (incorporated herein by reference). A 4E11 hybridoma cell line has been deposited under Accession No. HB 9259 with the American Type Culture Collection. The monoclonal antibody binding to FLAG peptide is available from Eastman Kodak Co., Scientific Imaging Systems Division, New Haven, Conn.

pFLAG-CMV-1 (SIGMA) can be presented as an example of a basic vector which can be expressed in mammalian cells and enables obtaining the enzyme protein of the present invention as a fusion protein with the above FLAG peptide. Likewise, examples of a vector which can be expressed in insect cells include, but are not limited to, pFBIF (i.e., a vector prepared by integrating the region encoding FLAG peptide into pFastBac (Invitrogen Corporation); see the Example section described later). Those skilled in the art will be able to select an appropriate basic vector depending on, e.g., the host cell, restriction enzyme and identification peptide to be used for expression of the enzyme.

(5) Antibody Recognizing the G34 Enzyme Protein of the Present Invention

The present invention provides an antibody which is immunoreactive to the G34 enzyme protein. Such an antibody is capable of specifically binding to the enzyme protein via the antigen-binding site of the antibody (as opposed to non-specific binding). More specifically, a protein having the amino acid sequence of SEQ ID NO: 2 or 4 or a fragment, mutant or fusion protein thereof may be used as an immunogen for producing an antibody immunoreactive to each of them.

More specifically, such a protein, fragment, mutant or fusion protein contains an antigenic determinant or epitope for eliciting antibody formation. These antigenic determinant and epitope may be either linear or conformational (discontinuous). The antigenic determinant or epitope can be identified by any technique known in the art. Thus, the present invention also relates to an antigenic epitope of the G34 enzyme protein. Such an epitope is useful in preparing an antibody, particularly a monoclonal antibody, as described in more detail below.

The epitope of the present invention can be used in assays and as a research reagent for purifying a specific binding antibody from materials such as polyclonal sera or supernatants from cultured hybridomas. Such an epitope or a variant thereof may be prepared using techniques known in the art (e.g., solid phase synthesis, chemical or enzymatic cleavage of a protein) or using recombinant DNA technology.

The enzyme protein of the present invention may be used to derive any embodiment of an antibody. If the entire or partial polypeptide of or an epitope of the protein has been isolated, both polyclonal and monoclonal antibodies can be prepared using conventional techniques. See, e.g., Kennet et al. (eds.), Monoclonal Antibodies, Hybridomas: A New Dimension in Biological Analyses, Plenum Press, New York, 1980.

The present invention also provides a hybridoma cell line producing a monoclonal antibody specific to the G34 enzyme protein. Such a hybridoma can be produced and identified by conventional techniques. One method for producing such a hybridoma cell line involves immunizing an animal with the enzyme protein of the present invention, collecting spleen cells from the immunized animal, fusing the spleen cells with a myeloma cell line to give hybridoma cells, and identifying a hybridoma cell line which produces a monoclonal antibody binding to the enzyme. The resulting monoclonal antibody may be collected by conventional techniques.

The monoclonal antibody of the present invention encompasses chimeric antibodies, for example, humanized mouse monoclonal antibodies. Such a humanized antibody is advantageous in reducing immunogenicity when administered to a human subject.

The present invention also provides an antigen-binding fragment of the above antibody. Examples of an antigen-binding fragment which can be produced by conventional techniques include, but are not limited to, Fab and $F(ab')_2$ fragments. The present invention also provides an antibody fragment and derivative which can be produced by genetic engineering techniques.

The antibody of the present invention can be used in assays to detect the presence of the G34 enzyme protein of the present invention or a polypeptide fragment thereof, either in vitro or in vivo. The antibody of the present invention may also be used in purifying the G34 enzyme protein or a polypeptide fragment thereof by immunoaffinity chromatography.

Moreover, the antibody of the present invention may also be provided as a blocking antibody capable of blocking the binding of the above glycosyltransferase protein to its binding partner (e.g., acceptor substrate), thus inhibiting the enzyme's biological activity resulting from such binding. Such a blocking antibody may be identified using any suitable assay procedure, for example, by testing the antibody for the ability to inhibit the binding of the protein to certain cells expressing an acceptor substrate.

Alternatively, the blocking antibody may also be identified in assays for the ability to inhibit a biological effect resulting from the enzyme protein bound to its binding partner in target cells. Such an antibody may be used in an in vitro procedure or administered in vivo to inhibit a biological activity mediated by the entity that generated the antibody. Thus, the present invention also provides an antibody for treating disorders which are caused or exacerbated by either direct or indirect interaction between the G34 enzyme protein and its binding partner. Such therapy will involve in vivo administration of the blocking antibody to a mammal in an amount effective for inhibiting a binding partner-mediated biological activity. For use in such therapy, monoclonal antibodies are preferred and, in one embodiment, an antigen-binding antibody fragment is used.

(6) Nucleic Acid of the Present Invention for Canceration Assay

In response to the discovery of the above G34 enzyme protein, the inventors of the present invention have confirmed that mRNA encoding this protein is widely found in cancerous tissues and cell lines and that the expression level of the mRNA is significantly increased particularly in cancerous tissues. Thus, the G34 nucleic acid is useful as a tumor marker that is useful for, e.g., cancer diagnosis targeted at biological samples containing transcription products. In this aspect, the present invention provides a nucleic acid for measurement, which is capable of hybridizing under stringent conditions to a nucleic acid defined by the nucleotide sequence shown in SEQ ID NO: 1 or 3.

In one embodiment, the nucleic acid for measurement of the present invention is a primer or probe targeting the G34 nucleic acid in a biological sample and having a nucleotide sequence selected from the nucleotide sequence of SEQ ID NO: 1 or 3. In particular, since the nucleotide sequence of SEQ ID NO: 1 is derived from mRNA encoding a structural gene and contains the entire open reading frame (ORF) of the G34 gene, full-length or nearly full-length sequences of SEQ ID NO: 1 or 3 are usually found in transcription products from a biological sample. In light of this point, the primer or probe according to the present invention has a desired partial sequence selected from each nucleotide sequence of SEQ ID NO: 1 or 3 (either homologous or complementary to the selected sequence depending on the intended use) and hence can be provided as a nucleic acid capable of specifically hybridizing to the target sequence.

Typical examples of such a primer or probe include a native DNA fragment derived from a nucleic acid having at least a part of the nucleotide sequence shown in SEQ ID NO: 1 or 3, a DNA fragment synthesized to have at least a part of the nucleotide sequence shown in SEQ ID NO: 1 or 3, or complementary strands of these fragments.

Such a primer or probe as mentioned above may be used to detect and/or quantify the target nucleic acid in a biological sample, as described later. Since sequences on the genome can also be targeted, the nucleic acid of the present invention may also be used as an antisense primer for medical research or gene therapy.

(A) Probe of the Present Invention

In a preferred embodiment, the nucleic acid for measurement of the present invention is a probe targeting a nucleic acid having the nucleotide sequence of SEQ ID NO: 1 or 3 or a complementary strand of at least one of them. The probe contains an oligonucleotide composed of at least a dozen nucleotides, preferably at least 15 nucleotides, preferably at least 17 nucleotides, and more preferably at least 20 nucleotides selected from the nucleotide sequences of SEQ ID NOs: 1 and 3, or a complementary strand of the oligonucleotide, or full-length cDNA of its ORF region or a complementary strand of the cDNA.

In a case where the nucleic acid for measurement of the present invention is provided as an oligonucleotide probe, it is understood that a length of a dozen nucleotides (e.g., 15 nucleotides, preferably 17 nucleotides) may be sufficient for the nucleic acid to specifically hybridize under stringent conditions to its target nucleic acid. Namely, those skilled in the art will be able to select an appropriate partial sequence composed of at least 15 to 20 nucleotides from the nucleotide sequence of SEQ ID NO: 1 or 3 in accordance with known various strategies for oligonucleotide probe design. In this case, the amino acid sequence information shown in SEQ ID NO: 2 or 4 is helpful in selecting a unique sequence that may be suitable as a probe.

Likewise, in the case of a cDNA probe, for example, a probe with a high molecular weight is generally difficult to handle when used as a reagent or diagnostic agent for medical research. In light of this point, the probe of the present invention intended for medical research includes a nucleic acid composed of 50 to 500 nucleotides, more preferably 60 to 300 nucleotides selected from each nucleotide sequence of SEQ ID NO: 1 or 3.

The term "stringent conditions" found above means conditions of moderate or high stringency as explained earlier. Those skilled in the art will be able to readily determine and achieve conditions of moderate or high stringency suitable for the selected probe, on the basis of common knowledge and empirical rule about known procedures for various probe designs and hybridization conditions.

Although depending on, e.g., the nucleotide length to be selected and the hybridization conditions to be applied, a relatively short oligonucleotide probe can serve as a probe even when it has a mismatch of one or several nucleotides, particularly one or two nucleotides, in comparison with the nucleotide sequence of SEQ ID NO: 1 or 3. Likewise, a relatively long cDNA probe can also serve as a probe even when it has a mismatch of 50% or less, preferably 20% or less, in comparison with the nucleotide sequence of SEQ ID NO: 1 or a nucleotide sequence complementary thereto.

The probe of the present invention thus designed can be used as a labeled probe having a label such as a fluorescent label, a radioactive label or a biotin label, in order to detect or confirm a hybrid formed with a target sequence in G34.

For example, the labeled probe of the present invention may be used for confirmation or quantification of PCR amplification products from the G34 nucleic acid. In this case, it is preferable to use a probe targeting the nucleotide sequence located in a region between a pair of primer sequences used for PCR. An example of such a probe may be an oligonucleotide consisting of the nucleotide sequence shown in SEQ ID NO: 16 (corresponding to a complementary strand against nucleotides 525 to 556 in SEQ ID NO: 1) (see Example 3).

The probe of the present invention may be included in a kit such as a diagnostic DNA probe kit or may be immobilized on a chip such as a DNA microarray chip.

(B) Primers of the Present Invention

In a preferred embodiment, the primers obtained from the nucleic acid for the canceration assay of the present invention are oligonucleotide primers. To prepare oligonucleotide primers, two regions may be selected from the ORF region of the nucleotide sequence shown in SEQ ID NO: 1 or 3 in such a manner as to satisfy the following conditions:

a) the length of each region is at least several tens of nucleotides, particularly at least 15 nucleotides, preferably at least 17 nucleotides, more preferably at least 20 nucleotides, and at most 50 nucleotides; and b) the G+C content in each region is 40% to 70%.

In actual fact, oligonucleotide primers may be prepared as single-stranded DNAs having nucleotide sequences identical or complementary to the two regions thus selected, or may be prepared as single-stranded DNAs modified not to lose the binding specificity to these nucleotide sequences. Although each primer of the present invention preferably has a sequence that is completely complementary to the selected target sequence, a mismatch of one or two nucleotides may be permitted.

Examples of the pair of primers according to the present invention include a pair of oligonucleotides consisting of SEQ ID NOs: 14 and 15 (corresponding to complementary strands against nucleotides 481-501 and 562-581 in SEQ ID NO: 1, respectively) for human G34, and a pair of oligonucleotides consisting of SEQ ID NOs: 17 and 18 (corresponding to complementary strands against nucleotides 481-501 and 562-581 in SEQ ID NO: 3, respectively) for mouse G34.

(7) Canceration Assay According to the Present Invention

As described earlier, the G34 nucleic acid of the present invention was confirmed to show a significant increase in the expression level (i.e., transcription level of the gene from the genome into mRNA) in a cancerous biological sample when compared to a normal biological sample. The G34 nucleic acid of the present invention was demonstrated to be useful at least in a canceration assay for large intestine (colon) cancer or lung cancer (see Example 3).

According to detailed embodiments of the canceration assay of the present invention, transcription products extracted from a biological sample or a nucleic acid library derived therefrom may be used as a test sample and measured for the amount of the G34 nucleic acid (typically the amount of its mRNA) using the above probe or primer to determine whether the measured value is significantly higher than that of a normal biological sample. In this case, if the measured value of the test biological sample is significantly higher than the reference value of the normal biological sample, the test biological sample is determined as being cancerous or having a high grade of malignancy.

In the canceration assay of the present invention, the reference value for a normal biological sample used as a control may be a value measured for a control site (typically a normal site) in the same tissue of the same patient or may be a value normalized from known data obtained in a control site, e.g., the mean value of mRNA levels in normal tissues.

According to the measurement of expression levels using the nucleic acid for measurement of the present invention, human G34 is found to be expressed at a high level in the brain, skeletal muscle, pancreas, adrenal gland, testis and prostate when measured in normal sites, and there is also significant expression in other sites, although at a relatively low level. This indicates that human G34 expression is widely found over various tissues and that the expression level of human G34 is significantly increased even in tissues with a relatively low expression level, such as large intestine (colon) and lung tissues. Once these data have been provided, those skilled in the art will recognize the actual utility and effect of the nucleic acid for measurement of the present invention.

In this assay, whether the measured value for a test sample is significantly higher than that of a normal sample may be determined by the criteria that are set depending on the accuracy (positive rate) required for the assay or the grade of malignancy to be determined. The criteria may be freely set depending on the intended purpose; for example, the reference value to be determined as positive may be set to a lower value for the purpose of detecting tissues with a high grade of malignancy or may be set to a higher value for the purpose of comprehensively detecting test samples with signs or risk of canceration.

Examples will be given below of hybridization and PCR assays to illustrate the canceration assay of the present invention.

(A) Hybridization Assay

Embodiments of this assay include those using a probe obtained from the nucleic acid of the present invention, e.g., methods using various hybridization assays well known to those skilled in the art, exemplified by Southern blotting, Northern blotting, dot blotting or colony hybridization. In the case of requiring amplification and/or quantification of the detected signal, these methods may further be combined with immunoassay.

According to typical hybridization assays, a nucleic acid extracted from a biological sample or an amplification product thereof may be immobilized on a solid phase and hybridized with a labeled probe under stringent conditions. After washing, the label attached to the solid phase may be measured.

Extraction and purification of transcription products from a biological sample may be accomplished by using any method known to those skilled in the art.

(B) PCR Assay

In a preferred embodiment, the canceration assay, of the present invention includes PCR methods based on nucleic acid amplification using the primers of the present invention. The details of PCR are as explained earlier. In this subsection, a detailed PCR-based embodiment of this assay will be explained.

G34 mRNA in transcription products to be assayed can be amplified by PCR using a pair of primers located at both ends of a given region selected from the nucleotide sequence of G34. In this step, if even trace amounts of G34 nucleic acid fragments are present in an analyte, these fragments will serve as templates to replicate and amplify the nucleic acid region between the primer pair. After repeating a given number of PCR cycles, the nucleic acid fragments serving as templates are each amplified to a desired concentration. Under the same amplification conditions, the amplification product will be obtained in proportion to the amount of G34 mRNA present in the analyte. Then, the above probe or the like targeting the amplified region may be used to confirm whether the amplification product is the nucleic acid of interest and also quantify the same. Likewise, the nucleic acid in a normal tissue may also be measured in the same manner. In this case, a nucleic acid of a gene that is widely and usually present in the same tissue or the like (e.g., a nucleic acid encoding glyceraldehyde-3-phosphate dehydrogenase (GAPDH) or β-actin) may be used as a control to remove variations among individuals. The measured value for the transcription level of G34 is provided for comparison to assay the presence of canceration or the grade of malignancy, as described above.

A nucleic acid sample provided for PCR methods may be either total mRNA extracted from a biological sample (e.g., a test tissue or cell) or total cDNA reverse transcribed from mRNA. In a case where mRNA is amplified, the NASBA method (3SR method, TMA method) using the primer pair mentioned above may be employed. Since the NASBA method per se is well known and kits for this method are commercially available, the method may be readily accomplished by using the primer pair of the present invention.

To detect or quantify the above amplification product, the reaction solution after amplification may be electrophoresed and the resulting bands may be stained with ethidium bromide or the like, or alternatively, the electrophoresed amplification product may be immobilized onto a solid phase (e.g., a nylon membrane), hybridized with a labeled probe specifically hybridizing to a test nucleic acid (e.g., a probe having the nucleotide sequence of SEQ ID NO: 16) and washed, followed by detection of the label.

Examples of PCR methods preferred for this assay include quantitative PCR, especially kinetic RT-PCR or quantitative real-time PCR. In particular, quantitative real-time RT-PCR targeted at mRNA libraries is preferred in view that it allows direct purification of a target to be measured from a biological sample and directly reflects the transcription level. However, the nucleic acid quantification in this assay is not limited to quantitative PCR. Other known quantitative DNA assays (e.g., Northern blotting, dot blotting, DNA microarray) using the above probe may also be applied to the PCR products.

Moreover, when performed using a quencher fluorescent dye and a reporter fluorescent dye, quantitative R'T-PCR also enables quantification of a target nucleic acid in an analyte. In particular, it may be readily performed since kits for quantitative RT-PCR are commercially available. Moreover, a target nucleic acid may also be semi-quantified based on the intensity of the corresponding electrophoretic band.

(C) Assay for Therapeutic Effect on Cancer

Other embodiments of the canceration assay of the present invention include an assay for determining the effect of curing or alleviating cancer. For example, targets of this assay include all treatments such as administration of an anticancer agent and radiation therapy, and targets of these treatments include in vitro cancer cells or cancer tissues derived from cancer patients or experimental animal models for carcinogenesis.

According to this assay, in a case where a biological sample is subjected to a certain treatment, it is possible to know the therapeutic effect of the treatment on cancer by determining whether the transcription level of the G34 nucleic acid in the biological sample is reduced due to the treatment. This assay is not limited to a determination whether the transcription level is reduced, and the result may also be evaluated as effective when an increase in the transcription level is significantly prevented. The transcription level may not only be compared with that of an untreated tissue, but also traced over time after the treatment.

The assay of the present invention for therapeutic effect on cancer includes, for example, a determination whether a candidate substance for an anticancer agent is effective for cancerous tissues, whether resistance is developed to an anticancer agent in cancer patients receiving the agent, or whether a candidate substance for an anticancer agent is effective for diseased tissues or the like in experimental animal models.

Test tissues from experimental animal models are not limited to in vitro samples, and also include in vivo or ex vivo samples.

(8) Creation of Genetically Engineered Animal

As described earlier, the inventors of the present invention have identified the presence of mouse G34 and its nucleic acid sequence (SEQ ID NO: 3). The present invention also relates to a means for expression and functional analysis of G34 at the animal level on the basis of various gene conversion techniques using fertilized eggs or ES cells, typically relates to creating transgenic animals into which the G34 gene is introduced and knockout mice which are deficient in mouse G34, etc.

For example, the creation of knockout mice may be accomplished in accordance with routine techniques in the art (see, e.g., Newest Technique for Gene Targeting, edited by Takeshi Yagi, Yodosha Co., Ltd., Japan; Gene targeting, translated and edited by Tetsuo Noda, Medical Science International, Ltd., Japan). Namely, those skilled in the art will be able to obtain G34 homologous recombinant ES cells in accordance with known gene targeting techniques using sequence information of the mouse G34 nucleic acid disclosed herein, thus creating G34 knockout mice using these cells (see Example 7).

Recently, a method has been developed to prevent gene expression by small interfering RNA (T. R. Brummelkamp et al., Science, 296, 550-553 (2002)); it is also possible to create G34 knockout mice in accordance with such a known method.

The provision of G34 knockout mice will be helpful in elucidating the involvement of the G34 gene in certain vital phenomena, i.e., information on redundancy of the gene, the relationship between deficiency of the gene and phenotype at the animal level (including any type of abnormality affecting motor, mental and sensory functions), as well as functions of the gene during the animal life cycle including development, growth and ageing. More specifically, the knockout mice thus obtained may be used to detect a carrier of sugar chains synthesized by G34 and mG34 and to examine their relationship with physiological functions or diseases, etc. For example, glycoproteins and glycolipids may be extracted from each tissue derived from the knockout mice and compared with those of wild-type mice by techniques such as proteomics (e.g., two-dimensional electrophoresis, two-dimensional thin-layer chromatography, mass spectrometry) to identify a carrier of the synthesized sugar chains. Moreover, the relationship with physiological functions or diseases may be estimated by comparing phenotypes (e.g., fetal formation, growth process, spontaneous behavior) between knockout mice and wild-type mice.

Definitions of Terms

As used herein to describe the transcription level of a nucleic acid, the term "measured value" or "expression level" refers to the amount of the nucleic acid present in transcription products from a fixed amount of a biological sample, i.e., the concentration of the nucleic acid. Moreover, since the assay of the present invention relies on the comparison of such measured values, even when a nucleic acid is amplified, e.g., by PCR for the purpose of quantification or even when signals from a probe label are amplified, these amplified values may also be provided for relative comparison. Thus, the "measured value for a nucleic acid" can also be understood as the amount of the nucleic acid after amplification or the signal level after amplification.

As used herein, the term "target nucleic acid" or "the nucleic acid" encompasses all types of nucleic acids, regardless of in vivo or in vitro, including of course G34 mRNA, as well as those obtained using the mRNA as a template. It should be noted that the term "nucleotide sequence" used herein also includes a complementary sequence thereof, unless otherwise specified.

As used herein, the term "biological sample" refers to an organ, tissue or cell, as well as an experimental animal-derived organ, tissue, cell or the like, preferably refers to a tissue or cell. Examples of such a tissue include the brain, fetal brain, cerebellum, medulla oblongata, submandibular gland, thyroid gland, trachea, lung, heart, skeletal muscle, esophagus, duodenum, small intestine, large intestine (colon), rectum, colon, liver, fetal liver, pancreas, kidney, adrenal gland, thymus, bone marrow, spleen, testis, prostate, mammary gland, uterus and placenta, with the large intestine (colon) and lung being more preferred.

As used herein, the term "measure", "measurement" or "assay" encompasses all of detection, amplification, quantification and semi-quantification. In particular, the assay according to the present invention relates to a canceration assay for a biological sample, as described above, and hence can be applied to, e.g., cancer diagnosis and treatment in the medical field. The term "canceration assay" used herein includes an assay as to whether a biological sample becomes cancer, as well as an assay as to whether the grade of malignancy is high. The term "cancer" used herein typically encompasses malignant tumors in general and also includes disease conditions caused by the malignant tumors. Thus, targets of the assay according to the present invention include, but are not necessarily limited to, neuroblastoma, glioma, lung cancer, esophageal cancer, gastric cancer, pancreatic cancer, liver cancer, kidney cancer, duodenal cancer, small intestine cancer, large intestine (colon) cancer, rectal cancer, colon cancer and leukemia, with large intestine (colon) cancer and lung cancer being preferred.

The present invention will now be illustrated in more detail by way of the following examples.

EXAMPLES

Example 1

Cloning and Expression of Human G34 Gene, as Well as Purification of the Expressed Protein β3 galactosyltransferase 6 (β3GalT6) was used as a query for a BLAST search to thereby find a nucleic acid sequence with homology (SEQ ID NO: 1). The open reading frame (ORF) estimated from the nucleic acid sequence is composed of 1503 bp, i.e., 500 amino acids (SEQ ID NO: 2) when calculated as an amino acid sequence. The product encoded by these nucleic acid and amino acid sequences was designated human G34.

The amino acid sequence of G34 has a hydrophobic amino acid region characteristic of glycosyltransferases at its N-terminal end and shares a homology of 47% (nucleic acid sequence) and 28% (amino acid sequence) with the above β3GalT6. The amino acid sequence of G34 also retains all of the three motifs conserved in the β3GalT family.

In this example, G34 was not only confirmed for its expression in mammalian cells, but also allowed to be expressed in insect cells for further examination of its activity.

For activity confirmation, it would be sufficient to express at least an active region covering amino acid 189 to the C-terminal end of SEQ ID NO: 1, which is relatively homologous to β3GalT6. In this example, however, an active region covering amino acid 36 to the C-terminal end was attempted to be expressed.

Confirmation of Human G34 Gene Expression in Mammalian Cells

The active region covering amino acid 36 to the C-terminal end of G34 was genetically introduced into a mammalian cell line expression vector pFLAG-CMV3 using a FLAG Protein Expression system (Sigma-Aldrich Corporation). Since pFLAG-CMV3 has a multicloning site, a gene of interest can be introduced into pFLAG-CMV3 when the gene and pFLAG-CMV3 are treated with restriction enzymes and then subjected to ligation reaction.

Kidney-derived cDNA (Clontech, Marathon-ready cDNA) was used as a template and subjected to PCR using a 5'-primer (G34-CMV-F1: SEQ ID NO: 5) and a 3'-primer (G34-CMV-R1: SEQ ID NO: 6) to obtain a DNA fragment of interest. PCR was performed under conditions of 25 cycles of 98° C. for 10 seconds, 55° C. for 30 seconds, and 72° C. for 2 minutes. The PCR product was then electrophoresed on an agarose gel and isolated in a standard manner after gel excision. This PCR product has restriction enzyme sites HindIII and BamHI at the 5' and 3' sides, respectively.

After this DNA fragment and pFLAG-CMV3 were each treated with restriction enzymes HindIII and BamHI, the reaction solutions were mixed together and subjected to ligation reaction, so that the DNA fragment was introduced into pFLAG-CMV3. The reaction solution was purified by ethanol precipitation and then mixed with competent cells (E. coli DH5α). After heat shock treatment (42° C., 30 seconds), the cells were seeded on ampicillin-containing LB agar medium.

On the next day, the resulting colonies were confirmed by direct PCR for the DNA of interest. For more reliable results, after sequencing to confirm the DNA sequence, the vector (pFLAG-CMV3-G34A) was extracted and purified.

Human kidney cell-derived cell line 293T cells ($2 \times 10^6$) were suspended in 10 ml antibiotic-free DMEM medium (Invitrogen Corporation) supplemented with 10% fetal bovine serum, seeded in a 10 cm dish and cultured for 16 hours at 37° C. in a $CO_2$ incubator. pFLAG-CMV3-G34A (20 ng) and Lipofectamin 2000 (30 μl, Invitrogen Corporation) were each mixed with 1.5 ml OPTI-MEM (Invitrogen Corporation) and incubated at room temperature for 5 minutes. These two solutions were further mixed gently and incubated at room temperature for 20 minutes. This mixed solution was added dropwise to the dish and cultured for 48 hours at 37° C. in a $CO_2$ incubator.

The supernatant (10 ml) was mixed with $NaN_3$ (0.05%), NaCl (150 mM), $CaCl_2$ (2 mM) and anti-FLAG-M1 resin (100 4, SIGMA), followed by overnight stirring at 4° C. On the next day, the supernatant was centrifuged (3000 rpm, 5 minutes, 4° C.) to collect a pellet fraction. After addition of 2 mM $CaCl_2$-TBS (900 μl), centrifugation was repeated (2000 rpm, 5 minutes, 4° C.) and the resulting pellet was suspended in 200 μl of 1 mM $CaCl_2$-TBS for use as a sample for activity measurement (G34 enzyme solution). A part of this sample was electrophoresed by SDS-PAGE and Western blotted using anti-FLAG M2-peroxidase (SIGMA) to confirm the expression of the G34 protein of interest.

As a result, a band was detected at a position of about 60 kDa, thus confirming the expression of the G34 protein.

Insertion of Human G34 Gene into Insect Cell Expression Vector

The active region covering amino acid 36 to the C-terminal end of G34 was integrated into pFastBac (Invitrogen Corporation) in a GATEWAY system (Invitrogen Corporation). Moreover, a Bac-to-Bac system (Invitrogen Corporation) was also used to construct a bacmid.

(1) Creation of Entry Clone

Kidney-derived cDNA (Clontech, Marathon-ready cDNA) was used as a template and subjected to PCR using a 5'-primer (G34-GW-F1; SEQ ID NO: 7) and a 3'-primer (G34-GW-R1; SEQ ID NO: 8) to obtain a DNA fragment of interest. PCR was performed under conditions of 25 cycles of 98° C. for 10 seconds, 55° C. for 30 seconds, and 72° C. for 2 minutes. The PCR product was then electrophoresed on an agarose gel and isolated in a standard manner after gel excision.

This product was integrated into pDONR201 (Invitrogen Corporation) through BP clonase reaction to create an "entry clone." The reaction was accomplished by incubating the DNA fragment of interest (5 μl), pDONR201 (1 μl, 150 ng), reaction buffer (2 μl) and BP clonase mix (2 μl) at 25° C. for 1 hour. The reaction was stopped by addition of proteinase K (1 μl) and incubation at 37° C. for 10 minutes. The above reaction solution (1 μl) was then mixed with 100 μl competent cells (E. coli DH5α, TOYOBO). After heat shock treatment, the cells were seeded in a kanamycin-containing LB plate.

On the next day, colonies were collected and confirmed by direct PCR for the DNA of interest. For more reliable results, after sequencing to confirm the DNA sequence, the vector (pDONR-G34A) was extracted and purified.

(2) Creation of Expression Clone

At both sides of the insertion site, the above entry clone has attL recombination sites for excision of lambda phage from E. coli. When the entry clone is mixed with LR clonase (a mixture of lambda phage recombination enzymes Int, IHF and Xis) and a destination vector, the insertion site is transferred to the destination vector to give an expression clone. Detailed steps are as shown below.

First, the entry clone (1 μl), pFBIF (0.5 μl, 75 ng), LR reaction buffer (2 μl), TE (4.5 μl) and LR clonase mix (2 μl) were reacted at 25° C. for 1 hour. The reaction was stopped by addition of proteinase K (1 μl) and incubation at 37° C. for 10 minutes (this recombination reaction results in pFBIF-G34A). pFBIF is a pFastBacl vector modified to have a Igκ signal sequence (SEQ ID NO: 9) and a FLAG peptide for purification (SEQ ID NO: 10). The Igκ signal sequence is inserted for the purpose of converting the expressed protein into a secretion form, while the FLAG peptide is inserted for the purpose of purification. To insert the FLAG peptide, a DNA fragment obtained from OT3 (SEQ ID NO: 11) as a template using primers OT20 (SEQ ID NO: 12) and OT21 (SEQ ID NO: 13) was inserted with Bam H1 and Eco R1. Further, to insert a Gateway sequence, a Gateway Vector Conversion system (Invitrogen Corporation) was used to introduce a Conversion cassette.

Subsequently, the whole volume of the above mixed solution (11 μl) was mixed with 100 μl competent cells (E. coli DH5α). After heat shock treatment, the cells were seeded in an ampicillin-containing LB plate. On the next day, colonies were collected and confirmed by direct PCR for the DNA of interest, and the vector (pFBIF-G34A) was extracted and purified.

(3) Construction of Bacmid by Bac-to-Bac System

Next, a Bac-to-Bac system (Invitrogen Corporation) was used to cause recombination between the above pFBIF— and pFastBac, so that G34 and other sequences were inserted into a bacmid capable of growing in insect cells.

This system utilizes a Tn7 recombination site and allows a gene of interest to be incorporated into a bacmid through a recombinant protein produced from a helper plasmid when pFastBac carrying the inserted gene of interest is merely introduced into bacmid-containing E. coli (DH10BAC, Invitrogen Corporation). In addition, such a bacmid contains the lacZ gene and allows selection based on the classical blue (not inserted)/white (inserted) colony screening.

Namely, the vector purified above (pFBIH-G34A) was mixed with 50 μl competent cells (*E. coli* DH10BAC). After heat shock treatment, the cells were seeded in a LB plate containing kanamycin, gentamicin, tetracycline, Bluo-gal and IPTG. On the next day, white single colonies were further cultured to collect the bacmid.

Introduction of Human G34 Gene-Containing Bacmid into Insect Cells

After confirming that the sequence of interest was inserted into the bacmid obtained from the above white colonies, this bacmid was introduced into insect cells (Sf21, commercially available from Invitrogen Corporation).

Namely, Sf21 cells were added to a 35 mm dish at 9×10$^5$ cells/2 ml antibiotic-containing Sf-900SFM (Invitrogen Corporation) and cultured at 27° C. for 1 hour to allow cell adhesion. (Solution A) Purified bacmid DNA (5 μl) diluted with 100 μl antibiotic-free Sf-900SFM. (Solution B) Cell-FECTIN Reagent (6 μl, Invitrogen Corporation) diluted with 100 μl antibiotic-free Sf-900SFM. Solutions A and B were then mixed carefully and incubated for 45 minutes at room temperature. After confirming cell adhesion, the culture solution was aspirated and replaced by antibiotic-free Sf-900SFM (2 ml). The solution prepared by mixing Solutions A and B (lipid-DNA complexes) was diluted and mixed carefully with antibiotic-free Sf900II (800 μl). The culture solution was aspirated from the cells and replaced by the diluted solution of lipid-DNA complexes, followed by incubation at 27° C. for 5 hours. The transfection mixture was then removed and replaced by antibiotic-containing Sf-900SFM culture solution (2 ml), followed by incubation at 27° C. for 72 hours. At 72 hours after transfection, the cells were released by pipetting and collected together with the culture solution, followed by centrifugation at 3000 rpm for 10 minutes. The resulting supernatant was stored in another tube (which was used as a first virus solution).

Sf21 cells were introduced into a T75 culture flask at 1×10$^7$ cells/20 ml Sf-900SFM (antibiotic-containing) and incubated at 27° C. for 1 hour. After the cells were adhered, the first virus (800 μl) was added and cultured at 27° C. for 48 hours. After 48 hours, the cells were released by pipetting and collected together with the culture solution, followed by centrifugation at 3000 rpm for 10 minutes. The resulting supernatant was stored in another tube (which was used as a second virus solution).

Moreover, Sf21 cells were introduced into a T75 culture flask at 1×10$^7$ cells/20 ml Sf-900SFM (antibiotic-containing) and incubated at 27° C. for 1 hour. After the cells were adhered, the second virus solution (100 μl) was added and cultured at 27° C. for 72 hours. After culturing, the cells were released by pipetting and collected together with the culture solution, followed by centrifugation at 3000 rpm for 10 minutes. The resulting supernatant was stored in another tube (which was used as a third virus solution). In addition, Sf21 cells were introduced into a 100 ml spinner flask at a concentration of 6×10$^5$ cells/ml in a volume of 100 ml. The third virus solution (1 ml) was added and cultured at 27° C. for about 96 hours. After culturing, the cells and the culture solution were collected and centrifuged at 3000 rpm for 10 minutes. The resulting supernatant was stored in another tube (which was used as a fourth virus solution).

Resin Purification of G34

The pFLAG-G34 supernatant of the above fourth virus solution (10 ml) was mixed with NaN$_3$ (0.05%), NaCl (150 mM), CaCl$_2$ (2 mM) and anti-FLAG-M1 resin (100 μl, SIGMA), followed by overnight stirring at 4° C. On the next day, the mixture was centrifuged (3000 rpm, 5 minutes, 4° C.) to collect a pellet fraction. After addition of 2 mM CaCl$_2$-TBS (900 μl), centrifugation was repeated (2000 rpm, 5 minutes, 4° C.) and the resulting pellet was suspended in 200 μl of 1 mM CaCl$_2$-TBS for use as a sample for activity measurement (G34 enzyme solution). A part of this sample was electrophoresed by SDS-PAGE and Western blotted using anti-FLAG M2-peroxidase (SIGMA) to confirm the expression of the G34 protein of interest. As a result, a plurality of bands were detected broadly around a position of about 60 kDa (which would be due to differences in post-translational modifications such as glycosylation), thus confirming the expression of the G34 protein.

Example 2

Search for Glycosyltransferase Activity of Human G34 Protein (1) Screening of GalNAc Transferase Activity The G34 protein was examined for its substrate specificity, optimum buffer, optimum pH and divalent ion requirement in its β1,3-N-acetylgalactosaminyltransferase activity.

The following reaction system was used for examining the G34 enzyme protein for its acceptor substrate specificity in its GalNAc transfer activity.

In the reaction solutions shown below, each of the following was used at 10 nmol as an acceptor substrate: pNp-α-Gal, oNp-β-Gal, Bz-α-GlcNAc, pNp-β-GlcNAc, Bz-α-GalNAc, pNp-β-GalNAc, pNp-α-Glc, pNp-β-Glc, pNp-β-GlcA, pNp-α-Fuc, pNp-α-Xyl, pNp-β-Xyl and pNp-α-Man (all purchased from SIGMA), wherein "Gal" represents a D-galactose residue, "Xyl" represents a D-xylose residue, "Fuc" represents a D-fucose residue, "Man" represents a D-mannose residue and "GlcA" represents a glucuronic acid residue.

Each reaction solution was prepared as follows (final concentrations in parentheses): each substrate (10 nmol), MES (2-morpholinoethanesulfonic acid) (pH 6.5, 50 mN), MnCl$_2$ (10 mM), Triton X-100 (trade name) (0.1%), UDP-GalNAc (2 mM) and UDP-[$^{14}$C]GlcNAc (40 nCi) were mixed and supplemented with 5 μl G34 enzyme solution, followed by dilution with H$_2$O to a total volume of 20 μl (see Table 1).

TABLE 1

| Composition of reaction solutions (μl) | | | | |
|---|---|---|---|---|
| | E(+), D(+) | ×8 | E(−), D(+) | E(+), D(−) |
| Enzyme solution | 5 | 40 | 0 | 5 |
| 140 mM HEPES pH 7.4 | 2 | 16 | 2 | 2 |
| 100 mM UDP-GalNAc | 0.5 | 4 | 0.5 | 0 |
| 200 mM MnCl$_2$ | 1 | 8 | 1 | 1 |
| 10% Triton CF-54 | 0.6 | 4.8 | 0.6 | 0.6 |
| H$_2$O | 5.9 | 47.2 | 10.9 | 6.4 |
| 10 nmol/μl Acceptor | 5 | 40 | 5 | 5 |
| Total | 20 | | 20 | 20 |

The above reaction mixtures were each reacted at 37° C. for 16 hours. After completion of the reaction, 200 μl H$_2$O was added and each mixture was lightly centrifuged to obtain the supernatant. The supernatant was passed through a Sep-Pak plus C18 Cartridge (Waters), which had been washed once with 1 ml methanol and twice, with 1 ml H$_2$O and then equilibrated, to allow the substrate and product in the supernatant to adsorb to the cartridge. After washing the cartridge twice with 1 ml H$_2$O, the adsorbed substrate and product were eluted with 1 ml methanol. The eluate was mixed with 5 ml liquid scintillator ACSII (Amersham Biosciences) and measured for the amount of radiation with a scintillation counter (Beckman Coulter).

As a result, the G34 protein was identified to be GalNAc transferase having the ability to transfer GalNAc to pNp-β-GlcNAc. The enzymatic activity was linearly increased at least over the course of the reaction time between 0 and 16 hours when UDP-GlcNAc was used as a donor substrate and Bz-β-GlcNAc was used as an acceptor substrate (see Table 2 and FIG. 1).

TABLE 2

| Reaction time | Area (%) |
|---|---|
| 1 hour | 0 |
| 2 hours | 2.388 |
| 4 hours | 6.195 |
| 16 hours | 13.719 |

Determination of Linking Mode

NMR was performed to analyze the linking mode of the sugar chain structure synthesized by the G34 enzyme protein.

First, the reaction solution (final concentrations in parentheses) was prepared by adding Bz-β-GlcNAc (640 nmol) as an acceptor substrate, HEPES buffer (pH 7.4, 14 mM), Triton CF-54 (trade name) (0.3%), UDP-GalNAc (2 mM), $MnCl_2$ (10 mM) and 500 μl G34 enzyme solution, followed by dilution with $H_2O$ to a total volume of 2 ml. This reaction solution was reacted at 37° C. for 16 hours. The reaction solution was heated for 5 minutes at 95° C. to stop the reaction and then purified by filtration through an Ultrafree-MC (Millipore Corporation).

In one development, 50 μl of the filtrate was analyzed by high performance liquid chromatography (HPLC) using a reversed-phase column ODS-80Ts QA (4.6×250 mm, Tosoh Corporation, Japan). The developing solvent used was an aqueous 9% acetonitrile-0.1% trifluoroacetic acid solution. The elution conditions were set to 1 ml/minute at 40° C. Absorbance at 210 nm was used as an index for elution peak detection using an SPD-10A$_{vp}$ (Shimadzu Corporation, Japan). As a result, a new elution peak was observed, which was not detected in the control. This peak was separated and lyophilized for use as an NMR sample.

Figure 2A:
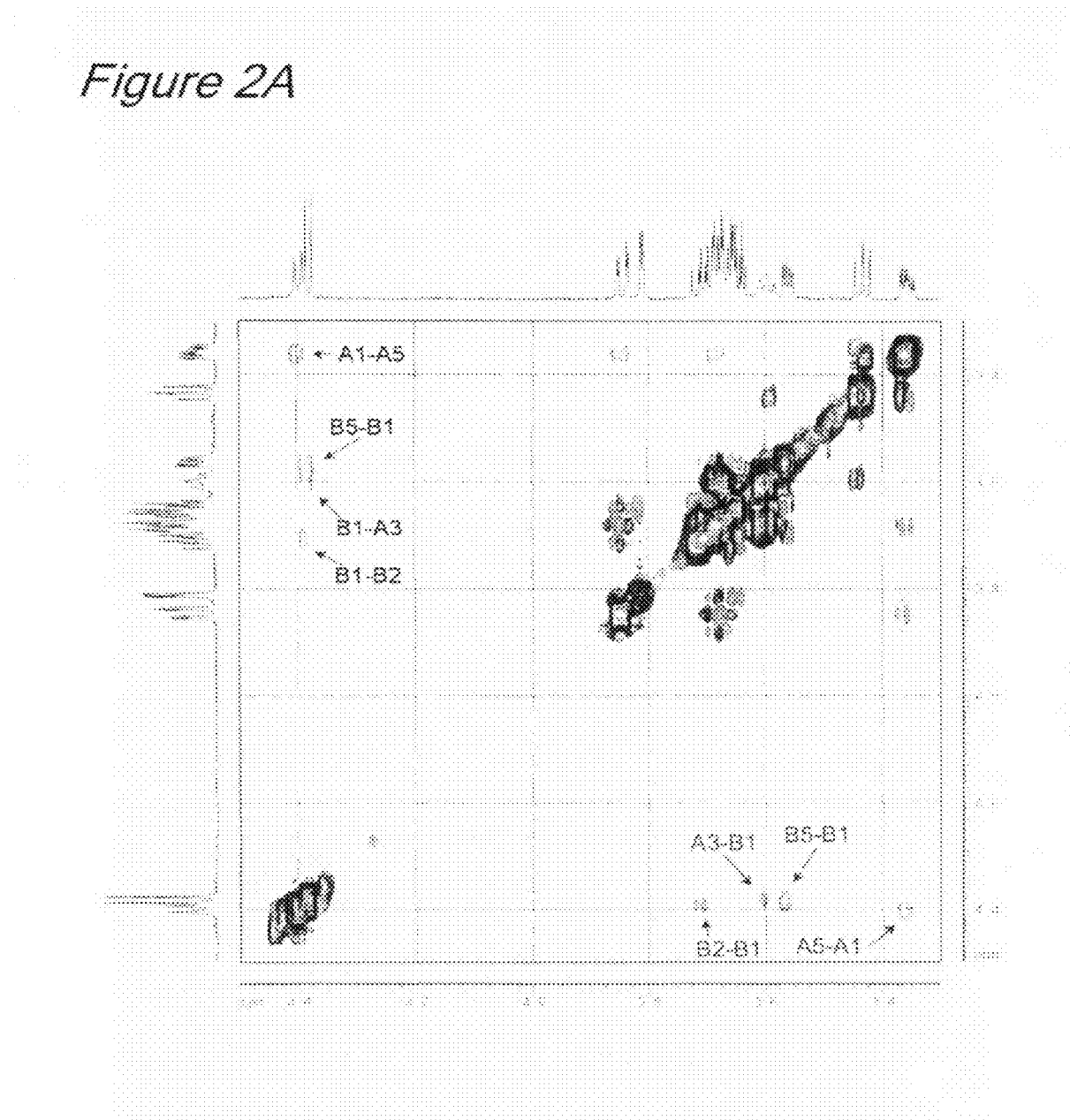
FIG. 2A shows the results of NMR measurement, used for analysis of the sugar chain structure synthesized by the G34 enzyme protein according to this example.
Figure 2B:
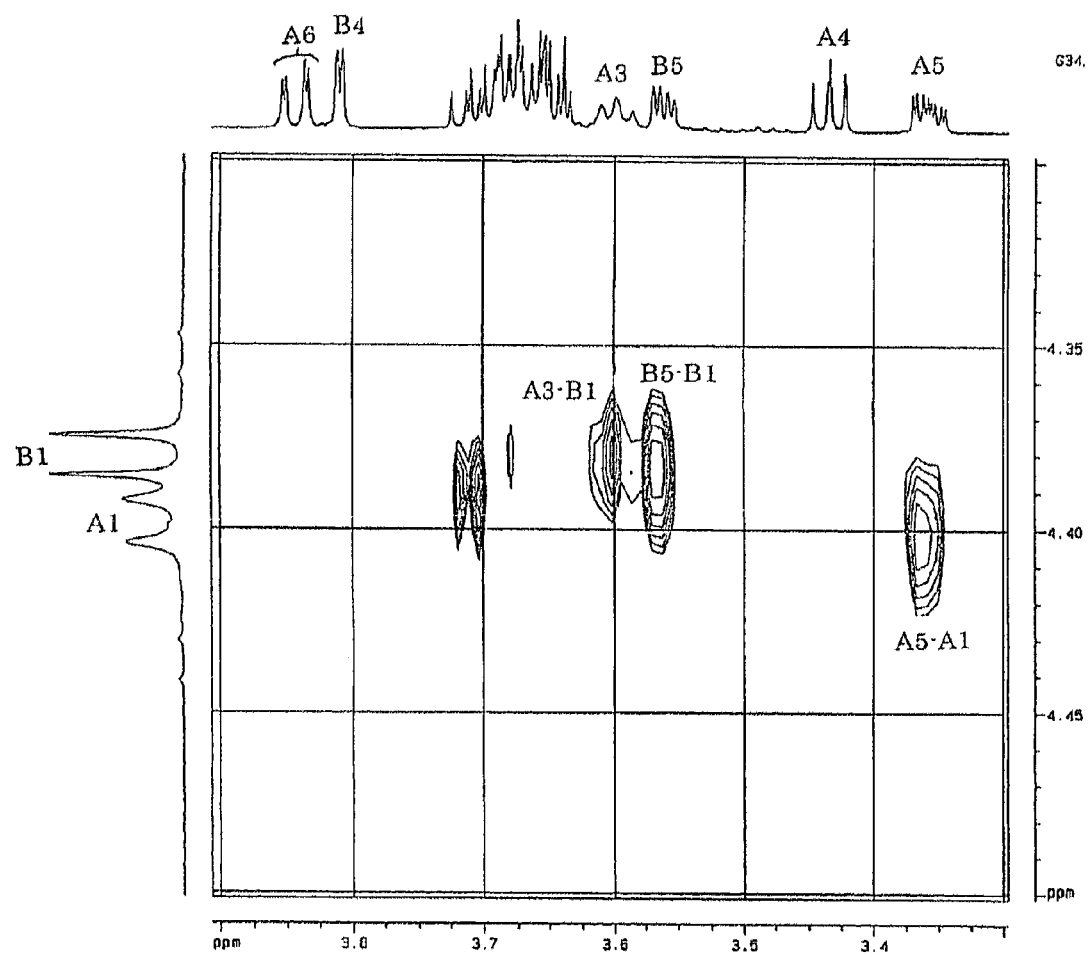
FIG. 2B shows a partial magnified view of the NMR results in FIG. 2A.

NMR was performed using a DMX750 (Bruker Daltonics). As a result, the sample was determined as having a β1-3 linkage between GalNAc and GlcNAc-β1-o-Bz (see FIGS. 2A and 2B). The reasons for this determination are as follows (see FIGS. 2A and 2B, along with FIGS. 3 and 4): a) two residues (referred to as A and B) both have a piston coupling constant of 8.4 Hz for the signal at position 1, suggesting that two pyranoses are in β-form; b) the spin coupling constants given in FIG. 3 indicate that A shows a spin coupling constant characteristic of glucose, while B shows a spin coupling constant characteristic of galactose; c) it is A that is linked to the benzyl because NOE was observed between methylene proton of the benzyl and A1 proton; d) there are two signals resulting from the methyl of N-acetyl and hence both residues are identified as N-acetylated sugars; and e) NOESY indicates the presence of NOE in B1-A3.

On the other hand, examination was also performed on motif sequences involved in the above enzymatic activity.

FIG. 5 shows the putative amino acid sequence of the G34 protein (SEQ ID NO: 2) compared with the amino acid sequences of various human β1-3Gal transferases (β3Gal-T1 to -T6). In FIG. 5, the boxed regions indicate the motifs common to Gal transferases. Among them, three motifs indicated with M1 to M3 are common to β1,3-linking glycosyltransferases. In this figure, the amino acid residues indicated with * are conserved among the compared sequences.

FIG. 6 shows a comparison of three motifs involved in the ability to form β1,3 linkages (corresponding to the M1 to M3 motifs in FIG. 5) among various β1-3GlcNAc transferases (β3Gn-T2 to -T5) and human Gal transferases T1 to T3, T5 and T6. In this figure, the amino acid residues indicated with * are conserved among the compared sequences.

As shown in FIGS. 5 and 6, it was indicated that the amino acid sequence of the G34 protein was conserved enough to have all the motifs (M1 to M3) involved in β1,3 linkages, upon comparison with the amino acid sequences of known various β1,3-linking glycosyltransferases.

Thus, this motif examination also supported the conclusion that the G34 protein has the ability to transfer GalNAc to GlcNAc with β1,3 glycosidic linkage.

Optimum Buffer and Optimum pH

The following reaction system was used for examining the optimum buffer and pH for the GalNAc transferase activity of G34. The acceptor substrate used was pNp-β-GlcNAc.

Any one of the following buffers was used (final concentrations in parentheses): MES (2-morpholinoethanesulfonic acid) buffer (pH 5.5, 5.78, 6.0, 6.5 and 6.75, 50 mM), sodium cacodylate buffer (pH 5.0, 5.6, 6.0, 6.2, 6.6, 6.8, 7.0, 7.2, 7.4 and 7.5, 25 mM) and N-[2-hydroxyethyl]piperazine-N'-[2-ethanesulfonic acid] (HEPES) buffer (pH 6.75, 7.00, 7.30, 7.40 and 7.50, 14 mM). The substrate (10 nmol), $MnCl_2$ (10 mM), Triton CF-54 (trade name) (0.3%), UDP-GalNAc (2 mM) and UDP-[$^{14}$C]GlcNAC (40 nCi) were mixed and supplemented with 5 μl G34 enzyme solution, followed by dilution with $H_2O$ to a total volume of 20 μl.

The above reaction mixtures were each reacted at 37° C. for 16 hours. After completion of the reaction, 200 μl $H_2O$ was added and each mixture was lightly centrifuged to obtain the supernatant. The supernatant was passed through a Sep-Pak plus C18 Cartridge (Waters), which had been washed once with 1 ml methanol and twice with 1 ml $H_2O$ and then equilibrated, to allow the substrate and product in the supernatant to adsorb to the cartridge. After washing the cartridge twice with 1 ml $H_2O$, the adsorbed substrate and product were eluted with 1 ml methanol. The eluate was mixed with 5 ml liquid scintillator ACSII (Amersham Biosciences) and measured for the amount of radiation with a scintillation counter (Beckman Coulter).

Figure 7:
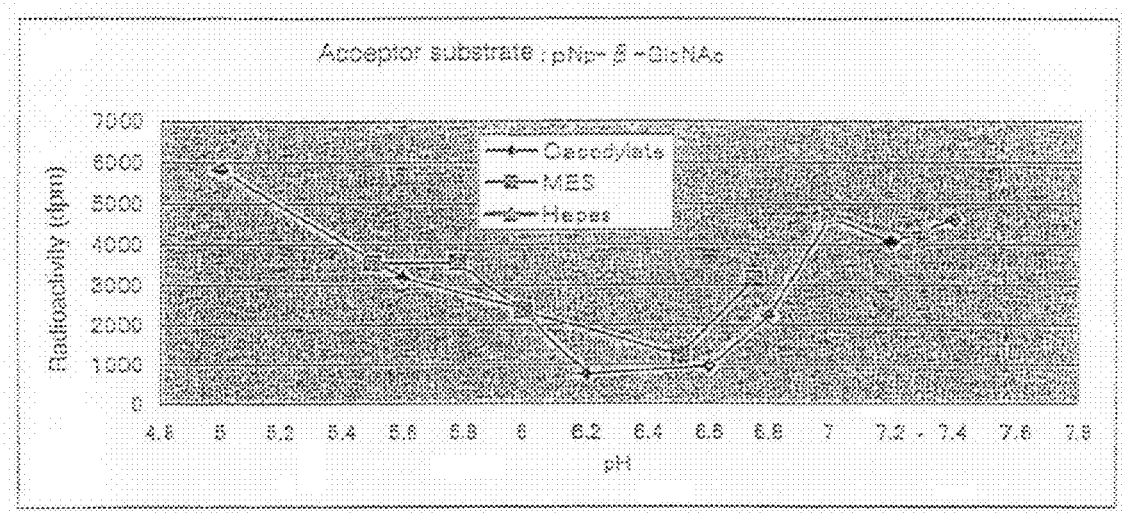
FIG. 7 is a diagram showing the pH dependence of the activity of the G34 enzyme protein according to this example.

As indicated by the results (see Table 3 and FIG. 7), in MES buffer, G34 showed the same strong activity around pH 5.50 and pH 5.78 within the examined range and its activity decreased in a pH-dependent manner until pH 6.5, but became strong again at pH 6.75. In sodium cacodylate buffer, the activity was highest at pH 5.0 within the examined range and the activity decreased in a pH-dependent manner until pH 6.2, increased in a pH-dependent manner until pH 7.0, and then plateaued until pH 7.4. In HEPES buffer, the activity increased in a pH-dependent manner and reached the highest value at pH 7.4 to 7.5 within the examined range. Among them, HEPES buffer at pH 7.4 to 7.5 resulted in the strongest activity.

TABLE 3

| PH | + | − | Sodium cacodylate |
|---|---|---|---|
| 5.0 | 6042 | 204 | 5838 |
| 5.6 | 3353 | 159 | 3194 |
| 6.0 | 2689 | 260 | 2429 |
| 6.2 | 907 | 138 | 769 |

TABLE 3-continued

| | | | |
|---|---|---|---|
| 6.6 | 1093 | 136 | 957 |
| 6.8 | 2488 | 258 | 2230 |
| 7.0 | 4965 | 259 | 4706 |
| 7.2 | 4377 | 309 | 4068 |
| 7.4 | 4930 | 304 | 4626 |

| pH | + | − | MES |
|---|---|---|---|
| 5.50 | 3735 | 197 | 3538 |
| 5.78 | 3755 | 184 | 3571 |
| 6.00 | 2514 | 141 | 2373 |
| 6.50 | 1981 | 734 | 1247 |
| 6.75 | 3289 | 136 | 3153 |

| pH | + | − | HEPES |
|---|---|---|---|
| 6.75 | 4894 | 149 | 4745 |
| 7.00 | 4912 | 121 | 4791 |
| 7.30 | 4294 | 127 | 4167 |
| 7.40 | 6630 | 120 | 6510 |
| 7.50 | 6895 | 240 | 6655 |

The following reaction system was used for examining the divalent ion requirement. The acceptor substrate used was Bz-β-GlcNAc.

The reaction solution (final concentrations in parentheses) was prepared by adding the substrate (10 nmol), HEPES buffer (pH 7.4, 14 mM), Triton CF-54 (trade name) (0.3%), UDP-GalNAc (2 mM), UDP-[$^{14}$C]GlcNAC (40 nCi) and 5 μl G34 enzyme solution and further adding MnCl$_2$, MgCl$_2$ or CoCl$_2$ at 2.5 mM, 5 mM, 10 mM, 20 mM or 40 mM, followed by dilution with H$_2$O to a total volume of 20

The above reaction mixture was reacted at 37° C. for 16 hours. After completion of the reaction, 200 μl H$_2$O was added and the mixture was lightly centrifuged to obtain the supernatant. The supernatant was passed through a Sep-Pak plus C18 Cartridge (Waters), which had been washed once with 1 ml methanol and twice with 1 ml H$_2$O and then equilibrated, to allow the substrate and product in the supernatant to adsorb to the cartridge. After washing the cartridge twice with 1 ml H$_2$O, the adsorbed substrate and product were eluted with 1 ml methanol. The eluate was mixed with 5 ml liquid scintillator ACSII (Amersham Biosciences) and measured for the amount of radiation with a scintillation counter (Beckman Coulter).

Figure 8:
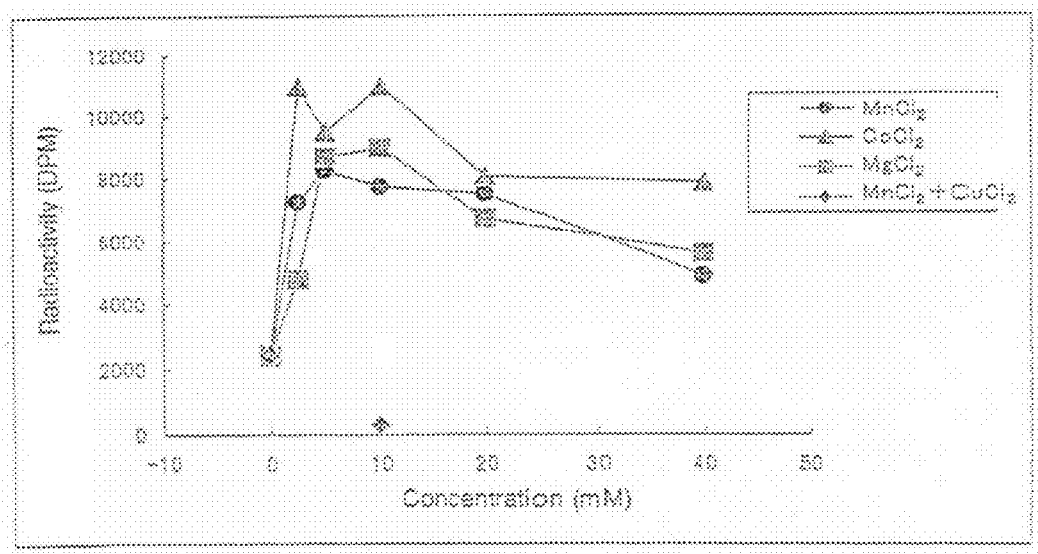
FIG. 8 is a diagram showing ion requirement for the activity of the G34 enzyme protein according to this example.

The results (see Table 4 and FIG. 8) indicated that the activity was enhanced by the addition of each divalent ion and confirmed that the G34 protein was an enzyme requiring divalent ions. Its activity nearly plateaued at 5 nM or higher concentration of Mn or Co and at 10 nM or higher concentration of Mg. Moreover, the Mn-induced enhancement of the activity was completely eliminated by addition of Cu.

TABLE 4

| RI assay (divalent ion requirement) | | |
|---|---|---|
| Metal ion | Concentration (mM) | DPM |
| Mn | 2.5 | 7260.09 |
| | 5 | 8270.23 |
| | 10 | 7748.77 |
| | 20 | 7515.86 |
| | 40 | 4870.48 |
| | 40 | 371.53 |
| Co | 2.5 | 10979.99 |
| | 5 | 9503.91 |
| | 10 | 10979.99 |
| | 20 | 8070.47 |
| | 40 | 7854.92 |

TABLE 4-continued

| RI assay (divalent ion requirement) | | |
|---|---|---|
| Metal ion | Concentration (mM) | DPM |
| Mg | 2.5 | 4800.03 |
| | 5 | 8692.15 |
| | 10 | 8980.56 |
| | 20 | 6726.32 |
| | 40 | 5592.88 |
| none | — | 2427.39 |
| EDTA | 20 | 149.32 |
| Mn + Cu | 10 + 10 | 239 |
| none | — | 155.64 |

Substrate Specificity to Oligosaccharides

The following reaction system was used for examining the acceptor substrate specificity to oligosaccharides. The acceptor substrates used were pNp-α-Gal, oNp-β-Gal, Bz-α-GlcNAc, Bz-β-GlcNAc, Bz-α-GalNAc, pNp-β-GalNAc, pNp-α-Glc, pNp-β-Glc, pNp-β-GlcA, pNp-α-Fuc, pNp-α-Xyl, pNp-β-Xyl, pNp-α-Man, lactoside-Bz, Lac-ceramide, Gal-ceramide, paragloboside, globoside, Gal-β1-4 GalNAc-α-pNp, Gal-β1-3 GlcNAc-β-pNp, GlcNAc-β1-4 GlcNAc β-Bz, pNp-core1 (Gal-β1-3 GalNAc-α-pNp), pNp-core2 (Gal-β1-3 (GlcNAc-β1-6) GalNAc-α-pNp), pNp-core3 (GlcNAc-β1-3 GalNAc-α-pNp) and pNp-core6 (GlcNAc-β1-6 GalNAc-α-pNp). "Lac" represents a D-lactose residue.

Each reaction solution (final concentrations in parentheses) was prepared by adding each substrate (50 nmol), HEPES buffer (pH 7.4, 14 mM), Triton CF-54 (trade name) (0.3%), UDP-GalNAc (2 mM), MnCl$_2$ (10 mM), UDP-[$^3$H] GlcNAc and 5 μl G34 enzyme solution, followed by dilution with H$_2$O to a total volume of 20 μl.

The above reaction mixtures were each reacted at 37° C. for 2 hours. After completion of the reaction, 200 μl H$_2$O was added and each mixture was lightly centrifuged to obtain the supernatant. The supernatant was passed through a Sep-Pak plus C18 Cartridge (Waters), which had been washed once with 1 ml methanol and twice with 1 ml H$_2$O and then equilibrated, to allow the substrate and product in the supernatant to adsorb to the cartridge. After washing the cartridge twice with 1 ml H$_2$O, the adsorbed substrate and product were eluted with 1 ml methanol. The eluate was mixed with 5 ml liquid scintillator ACSII (Amersham Biosciences) and measured for the amount of radiation with a scintillation counter (Beckman Coulter).

The results thus measured were compared assuming that the radioactivity obtained using Bz-β-GlcNAc as a substrate was set to 100% (see Table 5). When used as a substrate, pNp-core2 showed the largest increase in radioactivity. Bz-β-GlcNAc, GlcNAc-β1-4-GlcNAc-β-Bz, pNp-core6 and pNp-core3 also showed increases in radioactivity in the order named. The other substrates showed no increase in radioactivity.

TABLE 5

| No. | Acceptor substrate | % |
|---|---|---|
| 1 | pNp-α-Gal | N.D. |
| 2 | oNp-β-Gal | N.D. |
| 3 | Bz-α-GlcNAc | N.D. |
| 4 | Bz-β-GlcNAc | 100 |
| 5 | Bz-α-GalNAc | N.D. |
| 6 | pNp-β-GalNAc | N.D. |
| 7 | pNp-α-Glc | N.D. |
| 8 | pNp-β-Glc | N.D. |
| 9 | pNp-β-GlcA | N.D. |

TABLE 5-continued

| No. | Acceptor substrate | % |
|---|---|---|
| 10 | pNp-α-Fuc | N.D. |
| 11 | pNp-α-Xyl | N.D. |
| 12 | pNp-β-Xyl | N.D. |
| 13 | pNp-α-Man | N.D. |
| 14 | Lactoside-Bz | N.D. |
| 15 | Lac-ceramide | N.D. |
| 16 | Gal-ceramide | N.D. |
| 17 | Paragloboside | N.D. |
| 18 | Globoside | N.D. |
| 19 | Galβ1-4GalNAc-α-pNp | N.D. |
| 20 | Galβ1-3GlcNAc-β-pNp | N.D. |
| 21 | GlcNAcβ1-4GlcNAc-β-Bz | 29 |
| 22 | core1-pNp | N.D. |
| 23 | core2-pNp | 185 |
| 24 | core3-pNp | 8 |
| 25 | core6-pNp | 19 |

N.D.: Not determined due to no radioactivity
core1: Gal-β1-3-GalNAc-α-pNp
core2: Gal-β1-3-(GlcNAc-β1-6)GalNAc-α-pNp
core3: GlcNAc-β1-3-GalNAc-α-pNp
core6: GlcNAc-β1-6-GalNAc-α-pNp (2) Confirmation of Activity by HPLC Analysis Using uridine diphosphate-N-acetylgalactosamine (UDP-GalNAc; Sigma-Aldrich Corporation) as a sugar residue donor substrate and Bz-β-GlcNAc as a sugar residue acceptor substrate, the enzymatic activity of G34 was analyzed by high performance liquid chromatography (HPLC).

The reaction solution (final concentrations in parentheses) was prepared by adding Bz-β-GlcNAc (10 nmol), HEPES buffer (pH 7.4, 14 mM), Triton CF-54 (trade name) (0.3%), UDP-GalNAc (2 mM), MnCl$_2$ (10 mM) and 10 µl G34 enzyme solution, followed by dilution with H$_2$O to a total volume of 20 µl. This reaction solution was reacted at 37° C. for 16 hours. The reaction was stopped by addition of H$_2$O (100 µl) and the reaction solution was purified by filtration through an Ultrafree-MC (Millipore Corporation).

The filtrate (10 µl) was analyzed by high performance liquid chromatography (HPLC) using a reversed-phase column ODS-80Ts QA (4.6×250 mm, Tosoh Corporation, Japan). The developing solvent used was an aqueous 9% acetonitrile-0.1% trifluoroacetic acid solution. The elution conditions were set to 1 ml/minute at 40° C. Absorbance at 210 nm was used as an index for elution peak detection using an SPD-10A$_{vp}$ (Shimadzu Corporation, Japan).

As a result, a new elution peak was observed, which was not detected in the control.

(3) Analysis of Reaction Product by Mass Spectrometry

The above peak was collected and the reaction product was analyzed by mass spectrometry. Matrix-associated laser desorption ionization-time of flight/mass spectrometry (MALDI-TOF-MS) was performed using a Reflex IV (Bruker Daltonics). The sample at 10 µmol was dried and dissolved in 1 µl distilled water for use as a MALDI-TOF-MS sample.

As a result, a peak at 538.194 m/z was observed. This peak corresponded to the molecular weight of GalNAc-GlcNAc-Bz (sodium salt).

This result also indicated that the G34 enzyme protein transfers GalNAc to Bz-β-GlcNAc.

Example 3

Measurement for mRNA Expression Level of Human G34

(1) Expression Levels in Various Human Normal Tissues

Quantitative real-time PCR was used for comparing the mRNA expression levels of G34 in human normal tissues. Quantitative real-time PCR is a PCR method using a sense primer and an antisense primer in combination with a fluorescently-labeled probe. When a gene is amplified by PCR, a fluorescent label of the probe will be released to produce fluorescence. The fluorescence intensity is amplified in correlation with gene amplification and thus used as an index for quantification.

RNA of each human normal tissue (Clontech) was extracted with an RNeasy Mini Kit (QIAGEN) and converted into single strand DNA by the oligo(dT) method using a Super-Script First-Strand Synthesis System (Invitrogen Corporation). This DNA was used as a template and subjected to quantitative real-time PCR in an ABI PRISM 7700 (Applied Biosystems Japan Ltd.) using a 5'-primer (SEQ ID NO: 14), a 3'-primer (SEQ ID NO: 15) and a TaqMan probe (SEQ ID NO: 16). PCR was performed under conditions of 50° C. for 2 minutes and 95° C. for 10 minutes, and then under conditions of 50 cycles of 95° C. for 15 seconds and 60° C. for 1 minute. To prepare a calibration curve, plasmid DNA obtained by introducing a partial sequence of G34 into pFLAG-CMV3 (Invitrogen Corporation) was used as a template and subjected to PCR as described above.

The results confirmed that high-level expression was observed specifically, in the testis, followed by skeletal muscle and prostate in the order named (Table 6).

TABLE 6

G34 mRNA expression levels in human normal tissues

| Tissue | Copy number (×10000/µg, total RNA) | Standard error |
|---|---|---|
| Brain | 5.0 | 1.1 |
| Fetal brain | 10.3 | 0.7 |
| Cerebellum | 2.8 | 0.3 |
| Medulla oblongata | 4.9 | 0.3 |
| Submandibular gland | 6.7 | 0.4 |
| Thyroid gland | 1.8 | 0.6 |
| Trachea | 3.9 | 0.3 |
| Lung | 0.4 | 0.1 |
| Heart | 0.1 | 0.1 |
| Skeletal muscle | 25.8 | 1.1 |
| Small intestine | 5.1 | 0.3 |
| Large intestine (colon) | 0.6 | 0.3 |
| Liver | 0.3 | 0.1 |
| Fetal liver | 0.7 | 0.3 |
| Pancreas | 4.2 | 1.1 |
| Kidney | 1.6 | 0.3 |
| Adrenal gland | 10.8 | 1.3 |
| Thymus | 4.8 | 0.2 |
| Bone marrow | 3.1 | 0.4 |
| Spleen | 4.2 | 0.3 |
| Testis | 115.5 | 2.0 |
| Prostate | 14.6 | 1.5 |
| Mammary gland | 5.2 | 0.2 |
| Uterus | 5.0 | 0.2 |
| Placenta | 1.4 | 0.4 |

(2) Expression Levels in Human Cancer Cell Lines

Quantitative real-time PCR as mentioned above was used for comparing the mRNA expression levels of G34 in various cancer-derived human cell lines. After cells of each human cell line were collected, RNA was extracted with an RNeasy Mini Kit (QIAGEN) and converted into single strand DNA by the oligo(dT) method using a Super-Script First-Strand Synthesis System (Invitrogen Corporation). This DNA was used as a template and subjected to quantitative real-time PCR in an ABI PRISM 7700 (Applied Biosystems Japan Ltd.) using a 5'-primer (SEQ ID NO: 14), a 3'-primer (SEQ ID NO: 15) and a TaqMan probe (SEQ ID NO: 16). PCR was performed under conditions of 50° C. for 2 minutes and 95° C. for 10 minutes, and then under conditions of 50 cycles of 95° C. for 15 seconds and 60° C. for 1 minute.

Figure 9:
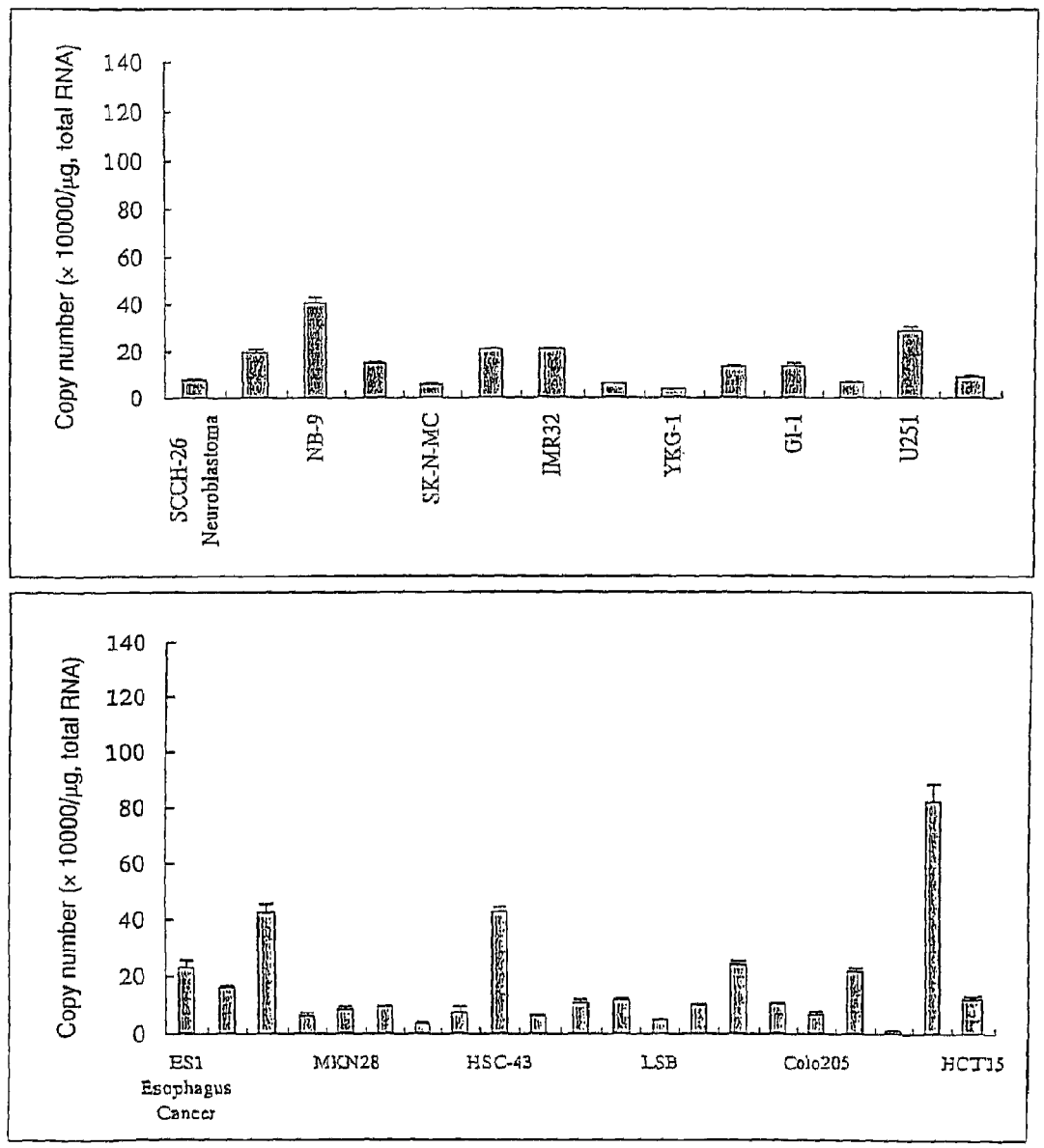
FIG. 9 presents graphs showing the expression levels of the G34 enzyme protein according to this example in human cell lines.
Figure 9:
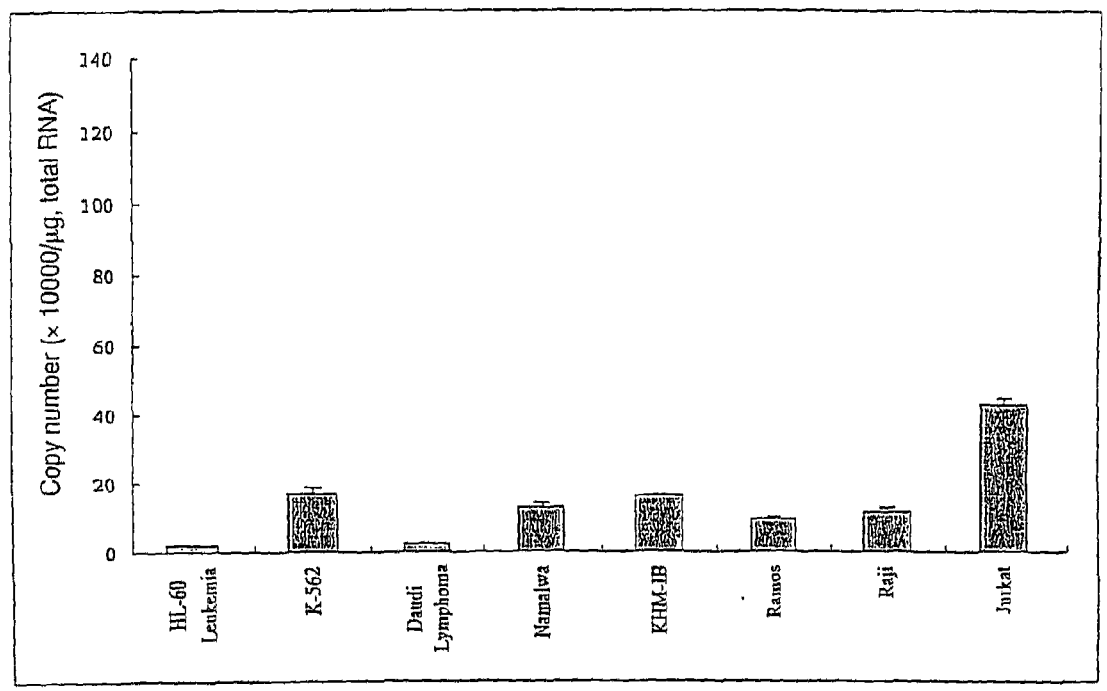
Figure 9:
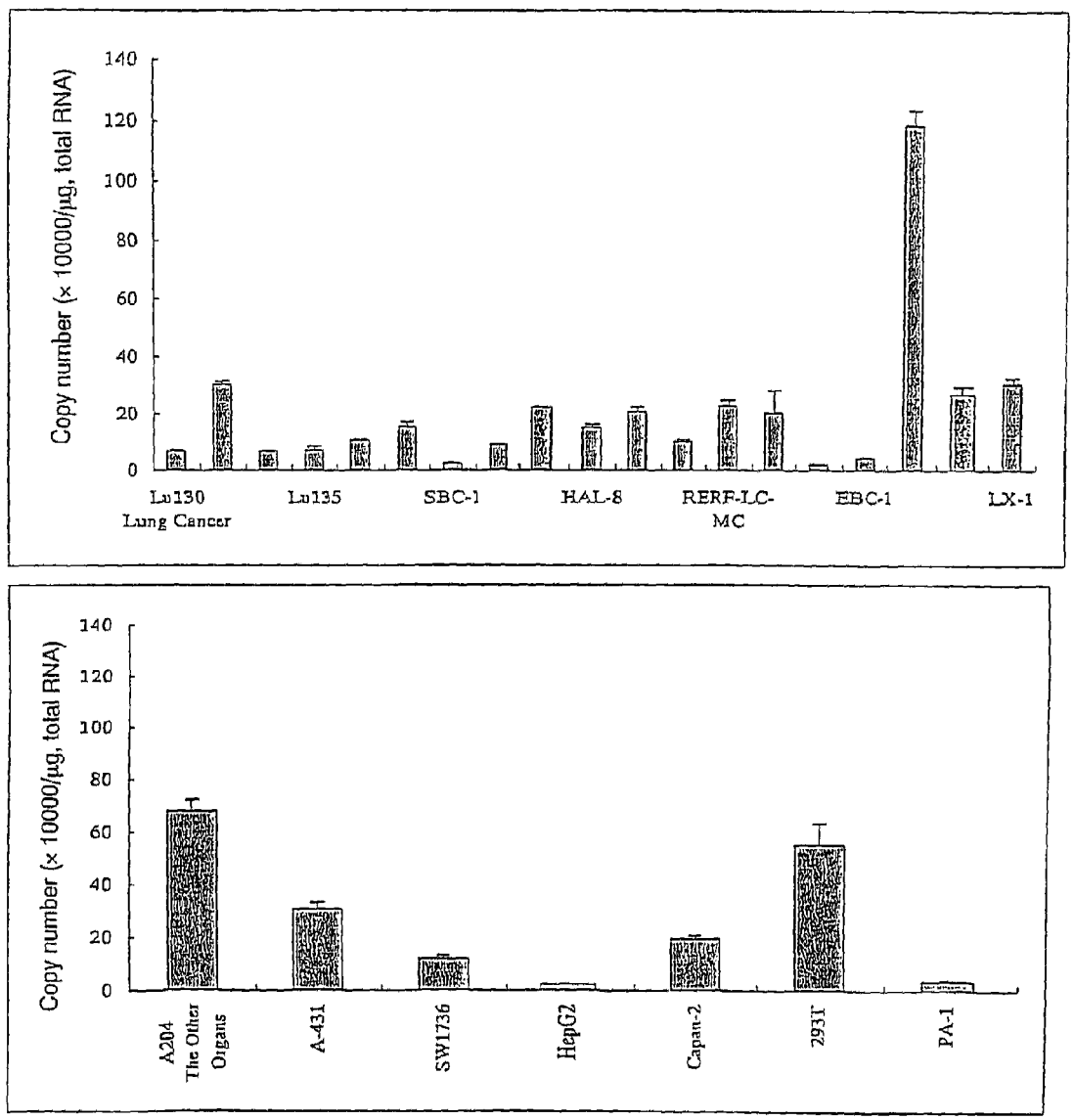

As a result, the expression was observed in all the human cell lines (Table 7, FIG. 9).

TABLE 7

G34 mRNA expression levels in human cell lines

|  | Cell line | Copy number (×10⁴/μg, total RNA) |  |
|---|---|---|---|
| Neuroblastoma | SCCH-26 | 7.9 | 0.6 |
|  | NAGAI | 19.5 | 1.5 |
|  | NB-9 | 40.6 | 2.3 |
|  | SK-N-SH | 14.9 | 0.7 |
|  | SK-N-MC | 5.8 | 0.5 |
|  | NB-1 | 20.9 | 0.5 |
|  | IMR32 | 21.0 | 0.2 |
| Glioma | T98G | 6.2 | 0.2 |
|  | YKG-1 | 3.9 | 0.0 |
|  | A172 | 13.4 | 0.9 |
|  | GI-1 | 13.7 | 1.3 |
|  | U118MG | 6.8 | 0.5 |
|  | U251 | 28.9 | 1.9 |
|  | KG-1-C | 9.1 | 0.6 |
| Lung cancer | Lu130 | 6.8 | 0.4 |
|  | Lu134A | 30.3 | 1.2 |
|  | Lu134B | 6.8 | 0.4 |
|  | Lu135 | 7.2 | 1.3 |
|  | Lu139 | 10.7 | 0.5 |
|  | Lu140 | 15.4 | 1.8 |
|  | SBC-1 | 2.5 | 0.2 |
|  | PC-7 | 9.1 | 0.2 |
|  | PC-9 | 22.4 | 0.1 |
|  | HAL-8 | 15.2 | 1.2 |
|  | HAL-24 | 20.8 | 1.7 |
|  | ABC-1 | 10.3 | 0.9 |
|  | RERF-LC-MC | 22.8 | 2.2 |
|  | EHHA-9 | 20.3 | 7.9 |
|  | PC-1 | 2.1 | 0.2 |
|  | EBC-1 | 4.4 | 0.2 |
|  | PC-10 | 118.8 | 4.9 |
|  | A549 | 27.1 | 2.6 |
|  | LX-1 | 30.7 | 2.1 |
| Esophageal cancer | ES1 | 23.0 | 2.5 |
|  | ES2 | 16.1 | 0.6 |
|  | ES6 | 42.8 | 3.0 |
| Gastric cancer | MKN1 | 6.2 | 1.1 |
|  | MKN28 | 8.6 | 1.0 |
|  | MKN7 | 9.7 | 0.1 |
|  | MKN74 | 3.5 | 0.8 |
|  | MKN-45 | 7.3 | 2.1 |
|  | HSC-43 | 42.8 | 1.7 |
|  | KATOIII | 6.4 | 0.4 |
|  | TMK-1 | 10.8 | 1.2 |
| Large intestine (colon) cancer | LSC | 11.8 | 0.6 |
|  | LSB | 4.9 | 0.3 |
|  | SW480 | 10.1 | 0.4 |
|  | SW1116 | 24.1 | 1.4 |
|  | Colon201 | 10.4 | 0.4 |
|  | Colo205 | 6.8 | 0.9 |
|  | C1 | 21.9 | 1.2 |
|  | WiDr | 1.2 | 0.0 |
|  | HCT8 | 82.2 | 6.2 |
|  | HCT15 | 12.1 | 1.0 |

TABLE 7-continued

G34 mRNA expression levels in human cell lines

|  | Cell line | Copy number (×10⁴/μg, total RNA) |  |
|---|---|---|---|
| Others | A204 | 67.9 | 4.4 |
|  | A-431 | 30.6 | 2.5 |
|  | SW1736 | 11.9 | 1.1 |
|  | HepG2 | 2.3 | 0.3 |
|  | Capan-2 | 19.4 | 1.2 |
|  | 293T | 55.1 | 8.3 |
|  | PA-1 | 3.5 | 0.6 |
| Leukemia | HL-60 | 2.1 | 0.1 |
|  | K-562 | 17.1 | 1.8 |
| Lymphoma | Daudi | 2.4 | 0.2 |
|  | Namalwa | 13.0 | 1.2 |
|  | KHM-IB | 16.4 | 0.4 |
|  | Ramos | 9.5 | 0.7 |
|  | Raji | 11.6 | 1.3 |
|  | Jurkat | 42.7 | 1.9 |

(3) Expression Levels in Cancerous Tissues

Quantitative real-time PCR as mentioned above was used for comparing the mRNA expression levels of G34 in cancer tissues and their surrounding normal tissues derived from patients with large intestine (colon) cancer and lung cancer.

From cancer and normal tissues of the same patient, RNA was extracted with an RNeasy Mini Kit (QIAGEN) and converted into single strand. DNA by the oligo(dT) method using a Super-Script First-Strand Synthesis System (Invitrogen Corporation). This DNA was used as a template and subjected to quantitative real-time PCR in an ABI PRISM 7700 (Applied Biosystems Japan Ltd.) using a 5'-primer (SEQ ID NO: 14), a 3'-primer (SEQ ID NO: 15) and a TaqMan probe (SEQ ID NO: 16). PCR was performed under conditions of 50 cycles of 50° C. for 2 minutes, 95° C. for 10 minutes, 95° C. for 15 seconds, and 60° C. for 1 minute. To correct variations among individuals, the resulting data were divided by the value of β-actin (internal standard gene) quantified using a kit of Applied Biosystems Japan before being compared.

The results indicated that the mRNA expression level of the G34 gene was significantly increased in these cancerous tissues (Table 8, Table 9).

TABLE 8

G34 mRNA expression levels in tissues from large intestine cancer patients

| Patient No. | Normal tissue | Standard error | Cancer tissue | Standard error | % Change |
|---|---|---|---|---|---|
| 1 | 0.15 | 0.04 | 0.35 | 0.07 | 2.3 |
| 2 | 0.15 | 0.07 | 8.63 | 0.65 | 58.0 |
| 3 | 0.07 | 0.02 | 1.55 | 0.15 | 23.5 |
| 4 | 0.08 | 0.05 | 1.82 | 0.26 | 22.0 |
| 5 | 0.08 | 0.02 | 0.60 | 0.07 | 7.2 |
| 6 | 1.04 | 0.08 | 1.92 | 0.21 | 1.8 |
| 7 | 0.07 | 0.02 | 5.37 | 1.06 | 81.3 |
| 8 | 1.54 | 0.27 | 8.30 | 0.96 | 5.4 |
| 9 | 0.05 | 0.04 | 1.70 | 0.37 | 34.3 |
| 10 | 0.05 | 0.04 | 0.10 | 0.04 | 2.0 |
| 11 | 0.60 | 0.29 | 10.23 | 1.47 | 17.2 |
| 12 | 0.17 | 0.13 | 2.36 | 0.43 | 14.3 |
| 13 | 0.18 | 0.09 | 1.70 | 0.27 | 9.4 |
| 14 | 0.18 | 0.08 | 2.76 | 0.23 | 15.2 |
| 15 | 0.18 | 0.05 | 3.49 | 0.34 | 19.2 |
| 16 | 0.20 | 0.15 | 1.84 | 0.25 | 9.3 |
| 17 | 0.28 | 0.05 | 7.41 | 0.51 | 26.4 |
| 18 | 0.05 | 0.04 | 5.92 | 0.38 | 119.3 |

TABLE 8-continued

G34 mRNA expression levels in tissues
from large intestine cancer patients

| Patient No. | Normal tissue | Standard error | Cancer tissue | Standard error | % Change |
|---|---|---|---|---|---|
| 19 | 0.15 | 0.11 | 4.68 | 0.67 | 31.4 |
| 20 | 0.13 | 0.06 | 4.61 | 2.22 | 34.9 |
| 21 | 0.02 | 0.02 | 8.40 | 1.65 | 508.0 |
| 22 | 0.20 | 0.07 | 3.57 | 0.43 | 18.0 |
| 23 | 0.55 | 0.27 | 2.33 | 1.23 | 4.3 |
| Average | 0.25 | 0.07 | 3.97 | 0.55 | 15.6 |

Copy number (×10000/μg, total RNA)

TABLE 9

G34 mRNA expression levels in tissues
from lung cancer patients

| Patient No. | Normal tissue | Standard error | Cancer tissue | Standard error | % Change |
|---|---|---|---|---|---|
| 1 | 0.48 | 0.06 | 2.03 | 0.27 | 4.2 |
| 3 | 0.00 | 0.00 | 0.55 | 0.21 | — |
| 4 | 2.43 | 0.40 | 6.13 | 0.17 | 2.5 |
| 5 | 0.10 | 0.04 | 2.74 | 0.32 | 27.7 |
| 6 | 1.69 | 0.28 | 3.11 | 0.69 | 1.8 |
| 7 | 0.60 | 0.16 | 2.76 | 0.35 | 4.6 |
| 8 | 2.30 | 0.38 | 6.23 | 0.21 | 2.7 |
| 9 | 1.26 | 0.27 | 2.51 | 0.10 | 2.0 |
| 10 | 1.47 | 0.18 | 4.76 | 0.57 | 3.2 |
| 11 | 0.64 | 0.00 | 1.14 | 0.11 | 1.8 |
| 12 | 0.56 | 0.06 | 0.69 | 0.04 | 1.2 |
| 13 | 1.32 | 0.02 | 1.98 | 0.15 | 1.5 |
| 14 | 0.17 | 0.02 | 0.66 | 0.02 | 4.0 |
| 15 | 0.71 | 0.05 | 2.71 | 0.13 | 3.8 |
| 16 | 1.07 | 0.13 | 15.64 | 1.11 | 14.6 |
| 17 | 1.03 | 0.12 | 8.27 | 0.73 | 8.1 |
| 18 | 0.13 | 0.02 | 1.95 | 0.09 | 14.8 |
| Average | 0.94 | 0.71 | 3.76 | 3.64 | 4.0 |

Copy number (×10000/μg, total RNA)

Example 4

Cloning and Expression of Mouse G34 Gene

The human G34 sequence obtained in Example 1 was used as a query for a search against the mouse gene sequence serela (Applied Biosystems) to thereby find a corresponding nucleic acid sequence with high homology. The open reading frame (ORF) estimated from this nucleic acid sequence is composed of 1515 by (SEQ ID NO: 3), i.e., 504 amino acids (SEQ ID NO: 4) when calculated as an amino acid sequence, and has a hydrophobic amino acid region characteristic of glycosyltransferases at its N-terminal end. This sequence shares a homology of 86% (nucleic acid sequence) and 88% (amino acid sequence) with human G34 (SEQ ID NOs: 1 and 2) (see FIG. 10). Moreover, the sequence retains all of the three motifs conserved in the β3GalT family. The product encoded by the nucleic acid sequence of SEQ ID NO: 3 and the amino acid sequence of SEQ ID NO: 4 was designated mouse G34 (mG34).

To examine the activity of mG34, G34 was allowed to be expressed in a mammalian cell line. In this example, the active region covering amino acid 35 to the C-terminal end of mG34 was genetically introduced into a mammalian cell line expression vector pFLAG-CMV3 using a FLAG Protein Expression system (Sigma-Aldrich Corporation).

The expression in mouse tissues was confirmed by PCR. Each mouse tissue (brain, thymus, stomach, small intestine, large intestine (colon), liver, pancreas, spleen, kidney, testis or skeletal muscle) was used as a template and subjected to PCR using a 5'-primer (mG34-CMV-F1; SEQ ID NO: 17) and a 3'-primer (mG34-CMV-R1; SEQ ID NO: 18). PCR was performed under conditions of 25 cycles of 98° C. for 10 seconds, 55° C. for 30 seconds, and 72° C. for 2 minutes. The PCR product was electrophoresed on an agarose gel to confirm a band of approximately 1500 bp. As a result, as shown in Table 10, the expression level was highest in the testis, followed by spleen and skeletal muscle in the order named.

TABLE 10 mG34 mRNA expression levels in mouse tissues

| Tissue | Expression level |
|---|---|
| Brain | ± |
| Thymus | − |
| Stomach | + |
| Small intestine | − |
| Large intestine (colon) | + |
| Liver | + |
| Pancreas | − |
| Spleen | − |
| Kidney | ++ |
| Testis | +++ |
| Skeletal muscle | ++ |

Mouse testis-derived cDNA was used as a template and subjected to PCR using a 5'-primer (mG34-CMV-F1; SEQ ID NO: 17) and a 3'-primer (mG34-CMV-R1; SEQ ID NO: 18) to obtain a DNA fragment of interest. PCR was performed under conditions of 25 cycles of 98° C. for 10 seconds, 55° C. for 30 seconds, and 72° C. for 2 minutes. The PCR product was then electrophoresed on an agarose gel and isolated in a standard manner after gel excision. This PCR product has restriction enzyme sites HindIII and NotI at the 5' and 3' sides, respectively.

After this DNA fragment and pFLAG-CMV3 were each treated with restriction enzymes HindIII and NotI, the reaction solutions were mixed together and subjected to ligation reaction, so that the DNA fragment was introduced into pFLAG-CMV3. The reaction solution was purified by ethanol precipitation and then mixed with competent cells (E. coli DH5α). After heat shock treatment (42° C., 30 seconds), the cells were seeded on ampicillin-containing LB agar medium.

On the next day, the resulting colonies were confirmed by direct PCR for the DNA of interest. For more reliable results, after sequencing to confirm the DNA sequence, the vector (pFLAG-CMV3-mG34A) was extracted and purified.

Human kidney cell-derived cell line 293T cells ($2 \times 10^6$) were suspended in 10 ml antibiotic-free DMEM medium (Invitrogen Corporation) supplemented with 10% fetal bovine serum, seeded in a 10 cm dish and cultured for 16 hours at 37° C. in a $CO_2$ incubator. pFLAG-CMV3-mG34A (20 ng) and Lipofectamin 2000 (30 μl, Invitrogen Corporation) were each mixed with 1.5 ml OPTI-MEM (Invitrogen Corporation) and incubated at room temperature for 5 minutes. These two solutions were further mixed gently and incubated at room temperature for 20 minutes. This mixed solution was added dropwise to the dish and cultured for 48 hours at 37° C. in a $CO_2$ incubator.

The supernatant (10 ml) was mixed with $NaN_3$ (0.05%), NaCl (150 mM), $CaCl_2$ (2 mM) and anti-M1 resin (100 μl, SIGMA), followed by overnight stirring at 4° C. On the next day, the supernatant was centrifuged (3000 rpm, 5 minutes, 4°

C.) to collect a pellet fraction. After addition of 2 mM CaCl$_2$-TBS (900 µl), centrifugation was repeated (2000 rpm, 5 minutes, 4° C.) and the resulting pellet was suspended in 200 µl of 1 mM CaCl$_2$-TBS for use as a sample for activity measurement (mouse G34 enzyme solution). A part of this sample was electrophoresed by SDS-PAGE and Western blotted using anti-FLAG M2-peroxidase (SIGMA) to confirm the expression of the mG34 protein of interest. As a result, a band was detected at a position of about 60 kDa, thus confirming the expression of the mG34 protein.

Example 5

Search for Glycosyltransferase Activity of Mouse G34

The following reaction system was used for examining mouse G34 for its substrate specificity in its β1,3-N-acetylgalactosamine transferase activity. In the reaction solutions shown below, each of the following was used at 10 nmol as an "acceptor substrate": pNp-α-Gal, oNp-β-Gal, Bz-α-GlcNAc, Bz-β-GlcNAc, Bz-α-GalNAc, pNp-β-GalNAc, pNp-α-Glc, pNp-β-Glc, pNp-β-GlcA, pNp-α-Fuc, pNp-α-Xyl, pNp-β-Xyl, pNp-α-Man, lactoside-Bz, Lac-ceramide, Gal-ceramide, Gb3, globoside, Gal-β1-4GalNAc-α-pNp, Galβ1-3GlcNAc-β-Bz, GlcNAc-β1-4-GlcNAc-β-Bz, core1-pNp, core2-pNp, core3-pNp and core6-pNp (all purchased from SIGMA).

Each reaction solution was prepared as follows (final concentrations in parentheses): each substrate (10 nmol), HEPES (N-[2-hydroxyethyl]piperazine-N'-[2-ethanesulfonic acid]) (pH 7.4, 14 mM), MnCl$_2$ (10 mM), Triton CF-54 (trade name) (0.3%), UDP-GalNAc (2 mM) and UDP-[$^{14}$C]GlcNAC (40 nCi) were mixed and supplemented with 5 µl mouse G34 enzyme solution, followed by dilution with H$_2$O to a total volume of 20 µl.

The above reaction mixtures were each reacted at 37° C. for 16 hours. After completion of the reaction, 200H$_2$O was added and each mixture was lightly centrifuged to obtain the supernatant. The supernatant was passed through a Sep-Pak plus C18 Cartridge (Waters), which had been washed once with 1 ml methanol and twice with 1 ml H$_2$O and then equilibrated, to allow the substrate and product in the supernatant to adsorb to the cartridge. After washing the cartridge twice with 1 ml H$_2$O, the adsorbed substrate and product were eluted with 1 ml methanol. The eluate was mixed with 5 ml liquid scintillator ACSII (Amersham Biosciences) and measured for the amount of radiation with a scintillation counter (Beckman Coulter).

The results thus measured were compared assuming that the radioactivity obtained using Bz-β-GlcNAc as a substrate was set to 100% (Table 11). When used as a substrate, Bz-β-GlcNAc showed the largest increase in radioactivity. core2-pNp, core6-pNp, core3-pNp, pNp-β-Glc and GlcNAc-β1-4-GlcNAc-β-Bz also showed high radioactivity in the order named. The other substrates showed no increase in radioactivity.

TABLE 11

| Acceptor substrate | % |
| --- | --- |
| pNp-α-Gal | ND |
| oNp-β-Gal | ND |
| Bz-α-GlcNAc | ND |
| Bz-β-GlcNAc | 100 |
| Bz-α-GalNAc | ND |
| pNp-β-GalNAc | ND |

TABLE 11-continued

| Acceptor substrate | % |
| --- | --- |
| pNp-α-Glc | ND |
| pNp-β-Glc | 12 |
| pNp-β-GlcA | ND |
| pNp-α-Fuc | ND |
| pNp-α-Xyl | ND |
| pNp-β-Xyl | ND |
| pNp-α-Man | ND |
| Lactoside-Bz | ND |
| Lac-ceramide | ND |
| Gal-ceramide | ND |
| Gb3 | ND |
| Globoside | ND |
| Galβ1-4GalNAc-α-pNp | ND |
| Galβ1-3GlcNAc-β-pNp | ND |
| GlcNAcβ1-4GlcNAc-β-Bz | 10 |
| core1-pNp | ND |
| core2-pNp | 25 |
| core3-pNp | 14 |
| core6-pNp | 18 |

Example 6

In Situ Hybridization on Mouse Testis

Figure 11:
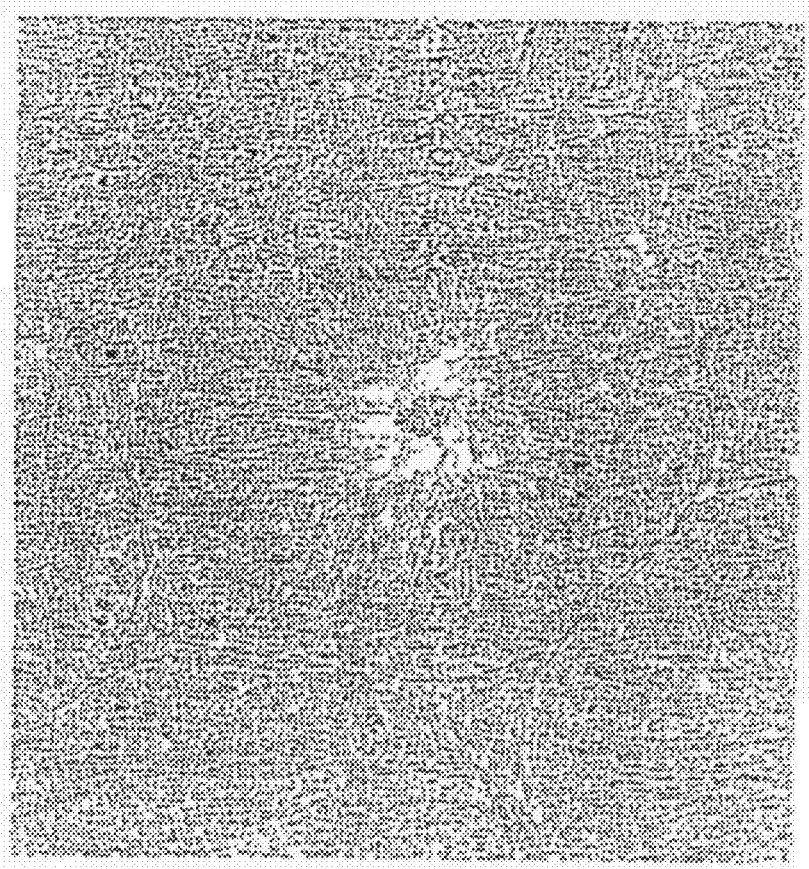
FIG. 11 shows the result of in situ hybridization performed on a mouse testis sample using the mG34 nucleic acid according to this example.

In situ hybridization using mG34 was performed on a mouse testis-derived sample to confirm the expression of, mG34 in the mouse testis sample (see FIG. 11).

Example 7

Creation of G34 Knockout Mouse

A targeting vector (pBSK-mG34-KOneo) is constructed in which pBluescript II SK(-) (TOYOBO) is inserted with a chromosomal fragment (about 10 kb) primarily composed of an approximately 10 kb fragment covering exons (i.e., Exons 3 to 12 (1242 bp) within the ORF region of mG34) containing activation domains of the gene (mG34) to be knocked out. pBSK-mG34-KOneo is also designed to have the drug resistance gene neo (neomycin resistance gene) introduced into Exons 7 to 9 which are putative GalNAc transferase active regions of mG34. As a result, Exons 7 to 9 of mG34 are deleted and replaced by neo. The pBSK-mG34-KOneo thus obtained is linearized with a restriction enzyme NotI, 80 µg of which is then transfected (e.g., by electroporation) into ES cells (derived from E14/129Sv mice) to select G418-resistant colonies. The G418-resistant colonies are transferred to 24-well plates and then cultured. After a part of the cells are frozen and stored, DNA is extracted from the remaining ES cells and around 120 colonies of recombinant clones are selected by PCR. Further, Southern blotting or other techniques are performed to confirm whether recombination occurs as expected, finally selecting around 10 clones of recombinants. ES cells from two of the selected clones are injected into C57BL/6 mouse blastocysts. The mouse embryos injected with the ES cells are transplanted into the uteri of recipient mice to generate chimeric mice, followed by germline transmission to obtain heterozygous knockout mice.

We claim:

1. A method for transferring N-acetyl-D-galactosamine to N-acetyl-D-glucosamine with β1,3 linkage from a N-acetyl-D-galactosamine donor substrate to an acceptor substrate containing N-acetyl-D-glucosamine, which comprises reacting the N-acetyl-D-galactosamine donor substrate, the acceptor substrate containing N-acetyl-D-glucosamine, and a polypeptide selected from the group consisting of the following:
   i) a polypeptide consisting of the amino acid sequence shown in SEQ ID NO: 2;
   ii) a polypeptide having the amino acid sequence covering amino acids 36 to 500 shown in SEQ ID NO: 2;
   iii) a polypeptide having the amino acid sequence covering amino acids 189 to 500 shown in SEQ ID NO: 2;
   iv) a polypeptide consisting of an amino acid sequence sharing at least 90% identity with the amino acid sequences described in i) to iii) described above, which transfers N-acetyl-D-galactosamine to N-acetyl-D-glucosamine with β1,3 linkage; and
   v) a polypeptide encoded by a nucleic acid sequence that hybridizes with the nucleic acid sequence shown in SEQ ID NO: 1 under high stringency conditions of hybridization at 50° C., 2 ×SSC, and 50% formamide and washing at 68° C., 0.2 ×SSC, and 0.1% SDS, which transfers N-acetyl-D-galactosamine to N-acetyl-D-glucosamine with β1,3 linkage.

2. The method according to claim 1, wherein the acceptor substrate is selected from the group consisting of glycoproteins, glycolipids, oligosaccharides, and polysaccharides having the N-acetyl-D-glucosamine residue.

3. The method according to claim 2, wherein the polypeptide shows transferase activity toward Bz-β-GlcNAc, GlcNAc,-β1-4-GlcNAc -β-Bz, Gal-β1-3 (GlcNAc-β1-6) GalNAc-α-pNp, GlcNAc-β1-3-GalNAc-α-pNp and GlcNAc-β1-6-GalNAc-α-pNp ("GlcNAc" represents an N-acetyl-D -glucosamine residue, "GalNAc" represents an N-acetyl-D-galactosamine residue, "Bz" represents a benzyl group, "pNp" represents a p-nitrophenyl group, "-" represents a glycosidic linkage, numbers in these formulae each represent the carbon number in the sugar ring where a glycosidic linkage is present, "α" and "β" represent anomers of the glycosidic linkage at the 1-position of the sugar ring, and an anomer whose positional relationship with $CH_2OH$ or $CH_3$ at the 5-position is trans and cis is represented by "α" and "β", respectively), when an oligosaccharide is used as the acceptor substrate.

4. The method according to claim 1, wherein the polypeptide shows transferase activity toward Bz-β-GlcNAc, GlcNAc-β1-4-GlcNAc -β-Bz, Gal-β1-3 (GlcNAc-β1-6) GalNAc-α-pNp, GlcNAc-β1-3-GalNAc-α-pNp and GlcNAc-β1-6-GalNAc-α-pNp ("GlcNAc" represents an N-acetyl-D -glucosamine residue, "GalNAc" represents an N-acetyl-D-galactosamine residue, "Bz" represents a benzyl group, "pNp" represents a p-nitrophenyl group, "-" represents a glycosidic linkage, numbers in these formulae each represent the carbon number in the sugar ring where a glycosidic linkage is present, "α" and "β" represent anomers of the glycosidic linkage at the 1-position of the sugar ring, and an anomer whose positional relationship with $CH_2OH$ or $CH_3$ at the 5-position is trans and cis is represented by "α" and "β", respectively), when an oligosaccharide is used as the acceptor substrate.

5. The method according to claim 1, wherein the N-acetyl -D-galactosamine donor substrate is selected from the group consisting of uridine diphosphate-N-acetylgalactosamine (UDP-GalNAc), adenosine diphosphate-N-galactosamine (ADP-GalNAc), guanosine diphosphate-N-acetylgalactosamine (GDP-GalNAc), and cytidine diphosphate-N-acetylgalactosarnine (CDP-GalNAc).

6. The method according to claim 1, wherein the activity is lower in a pH range of 6.2 to 6.6 than in other pH ranges.

7. The method according to claim 1, wherein the activity is enhanced at least in the presence of $Mn^{2+}$, $Co^{2+}$ or $Mg^{2+}$ and the $Mn^{2+}$-induced enhancement of the activity is almost completely eliminated in the presence of $Cu^{2+}$.

8. The method according to claim 1, wherein the polypeptide comprises the amino acid sequence of SEQ ID NO: 2.

9. The method according to claim 1, wherein the polypeptide comprises the amino acid sequence from residue 36 to residue 500 of SEQ ID NO: 2.

10. The method according to claim 1, wherein the polypeptide comprises the amino acid sequence from residue 189 to residue 500 of SEQ ID NO: 2.

11. The method according to claim 1, wherein the polypeptide is encoded by a nucleic acid sequence that hybridizes with the nucleic acid sequence shown in SEQ ID NO: 1 under high stringency conditions of hybridization at 50° C., 2 ×SSC, and 50% formamide and washing at 68° C., 0.2 ×SSC, and 0.1% SDS.

* * * * *

UNITED STATES PATENT AND TRADEMARK OFFICE
CERTIFICATE OF CORRECTION

PATENT NO.         : 8,227,213 B2
APPLICATION NO.    : 12/772117
DATED              : July 24, 2012
INVENTOR(S)        : Narimatsu et al.

It is certified that error appears in the above-identified patent and that said Letters Patent is hereby corrected as shown below:

On the Title page, the correction should insert --Industrial-- between "Advanced" and "Science" in (73) Assignee.

National Institute of Advanced Industrial Science and Technology, Tokyo (JP)

Signed and Sealed this
Thirteenth Day of August, 2013

Teresa Stanek Rea
*Acting Director of the United States Patent and Trademark Office*

SEQUENCE LISTING

<160> NUMBER OF SEQ ID NOS: 28

<210> SEQ ID NO 1
<211> LENGTH: 1503
<212> TYPE: DNA
<213> ORGANISM: Homo sapiens

<400> SEQUENCE: 1

```
atgcgaaact ggctggtgct gctgtgcccg tgtgtgctcg gggccgcgct gcacctctgg      60
ctgcggctgc gctccccgcc gcccgcctgc gcctccgggg ccggcccctgc agatcagttg     120
gccttatttc ctcagtggaa atctactcac tatgatgtgg tagttggcgt gttgtcagct     180
cgcaataacc atgaacttcg aaacgtgata agaagcacct ggatgagaca tttgctacag     240
catcccacat taagtcaacg tgtgcttgtg aagttcataa taggtgctca tggctgtgaa     300
gtgcctgtgg aagacaggga agatccttat tcctgtaaac tactcaacat cacaaatcca     360
gttttgaatc aggaaattga agcgttcagt ctgtccgaag acacttcatc ggggctgcct     420
gaggatcgag ttgtcagcgt gagtttccga gttctctacc ccatcgttat taccagtctt     480
ggagtgttct acgatgccaa tgatgtgggt ttccagagga acatcactgt caaactttat     540
caggcagaac aagaggaggc cctcttcatt gctcgcttca gtcctccaag ctgtggtgtg     600
caggtgaaca agctgtggta caagcccgtg aacaattca tcttaccaga gagctttgaa     660
ggtacaatcg tgtgggagag ccaagacctc acggccttg tgtcaagaaa tctccacaaa     720
gtgacagtga atgatggagg gggagttctc agagtcatta cagctgggga gggtgcattg     780
cctcatgaat tcttggaagg tgtggaggga gttgcaggtg gttttatata tactattcag     840
gaaggtgatg ctctcttaca caaccttcat tctcgccctc aaagacttat tgatcatata     900
aggaatctcc atgaggaaga tgccttactg aaggaggaaa gcagcatcta tgatgatatt     960
gttttttgtgg atgttgtcga cacttatcgt aatgttcctg caaaattatt gaacttctat    1020
agatggactg tggaaacaac gagcttcaat ttgttgctga agacagatga tgactgttac    1080
atagacctcg aagctgtatt taataggatt gtccaaaaga atctggatgg gcctaatttt    1140
tggtggggaa atttcagact gaattgggca gttgaccgaa ccggaaagtg caggagttg    1200
gagtacccga gccccgctta ccctgccttt gcatgtgggt caggatatgt gatctccaag    1260
gacatcgtca gtggctggc aagcaactcg gggaggttaa agacctatca gggtgaagat    1320
gtaagcatgg gcatctggat ggctgccata ggacctaaaa gataccagga cagtctgtgg    1380
ctgtgtgaga gacctgtga gacaggaatg ctgtcttctc ctcagtattc tccgtgggaa    1440
ctgacggaac tgtggaaact gaaggaacgg tgcggtgatc cttgtcgatg tcaagcaaga    1500
taa                                                                  1503
```

<210> SEQ ID NO 2
<211> LENGTH: 500
<212> TYPE: PRT
<213> ORGANISM: Homo sapiens

<400> SEQUENCE: 2

Met Arg Asn Trp Leu Val Leu Leu Cys Pro Cys Val Leu Gly Ala Ala
1               5                   10                  15

Leu His Leu Trp Leu Arg Leu Arg Ser Pro Pro Ala Cys Ala Ser
            20                  25                  30

Gly Ala Gly Pro Ala Asp Gln Leu Ala Leu Phe Pro Gln Trp Lys Ser
        35                  40                  45

```
Thr His Tyr Asp Val Val Gly Val Leu Ser Ala Arg Asn Asn His
    50                  55                  60

Glu Leu Arg Asn Val Ile Arg Ser Thr Trp Met Arg His Leu Leu Gln
65                  70                  75                  80

His Pro Thr Leu Ser Gln Arg Val Leu Val Lys Phe Ile Ile Gly Ala
                85                  90                  95

His Gly Cys Glu Val Pro Val Glu Asp Arg Glu Asp Pro Tyr Ser Cys
            100                 105                 110

Lys Leu Leu Asn Ile Thr Asn Pro Val Leu Asn Gln Glu Ile Glu Ala
        115                 120                 125

Phe Ser Leu Ser Glu Asp Thr Ser Ser Gly Leu Pro Glu Asp Arg Val
130                 135                 140

Val Ser Val Ser Phe Arg Val Leu Tyr Pro Ile Val Ile Thr Ser Leu
145                 150                 155                 160

Gly Val Phe Tyr Asp Ala Asn Asp Val Gly Phe Gln Arg Asn Ile Thr
                165                 170                 175

Val Lys Leu Tyr Gln Ala Glu Gln Glu Glu Ala Leu Phe Ile Ala Arg
            180                 185                 190

Phe Ser Pro Pro Ser Cys Gly Val Gln Val Asn Lys Leu Trp Tyr Lys
        195                 200                 205

Pro Val Glu Gln Phe Ile Leu Pro Glu Ser Phe Glu Gly Thr Ile Val
210                 215                 220

Trp Glu Ser Gln Asp Leu His Gly Leu Val Ser Arg Asn Leu His Lys
225                 230                 235                 240

Val Thr Val Asn Asp Gly Gly Gly Val Leu Arg Val Ile Thr Ala Gly
                245                 250                 255

Glu Gly Ala Leu Pro His Glu Phe Leu Glu Gly Val Glu Gly Val Ala
            260                 265                 270

Gly Gly Phe Ile Tyr Thr Ile Gln Gly Gly Asp Ala Leu Leu His Asn
        275                 280                 285

Leu His Ser Arg Pro Gln Arg Leu Ile Asp His Ile Arg Asn Leu His
290                 295                 300

Glu Glu Asp Ala Leu Leu Lys Glu Glu Ser Ser Ile Tyr Asp Asp Ile
305                 310                 315                 320

Val Phe Val Asp Val Asp Thr Tyr Arg Asn Val Pro Ala Lys Leu
                325                 330                 335

Leu Asn Phe Tyr Arg Trp Thr Val Glu Thr Thr Ser Phe Asn Leu Leu
        340                 345                 350

Leu Lys Thr Asp Asp Asp Cys Tyr Ile Asp Leu Glu Ala Val Phe Asn
        355                 360                 365

Arg Ile Val Gln Lys Asn Leu Asp Gly Pro Asn Phe Trp Trp Gly Asn
370                 375                 380

Phe Arg Leu Asn Trp Ala Val Asp Arg Thr Gly Lys Trp Gln Glu Leu
385                 390                 395                 400

Glu Tyr Pro Ser Pro Ala Tyr Pro Ala Phe Ala Cys Gly Ser Gly Tyr
                405                 410                 415

Val Ile Ser Lys Asp Ile Val Lys Trp Leu Ala Ser Asn Ser Gly Arg
            420                 425                 430

Leu Lys Tyr Gln Gly Glu Asp Val Ser Met Gly Ile Trp Met Ala
        435                 440                 445

Ala Ile Gly Pro Lys Arg Tyr Gln Asp Ser Leu Trp Leu Cys Glu Lys
450                 455                 460

Thr Cys Glu Thr Gly Met Leu Ser Ser Pro Gln Tyr Ser Pro Trp Glu
```

```
                     465                 470                 475                 480
Leu Thr Glu Leu Trp Lys Leu Lys Glu Arg Cys Gly Asp Pro Cys Arg
                    485                 490                 495

Cys Gln Ala Arg
            500

<210> SEQ ID NO 3
<211> LENGTH: 1515
<212> TYPE: DNA
<213> ORGANISM: Mouse

<400> SEQUENCE: 3
atgcgaaact ggctggtgct gctgtgccct tgcgtgctcg gggccgcgct gcacctctgg      60
cacctctggc tccgttcccc gccgacccca cacaacaccg ggcccagcgc ggcagatcaa     120
tcagccttat ttcctcactg gaaatttagc cactatgatg tggtagttgg tgtgttatca     180
gctcgaaata accacgaact tcgaaatgtg ataaggaaca cctggctgaa gaatttgctg     240
catcatccta cattaagtca acgtgtgctt gtgaagttca taataggtgc ccgtggctgt     300
gaagtgcctg tggaagacag ggaggatcct tactcctgcc gactgctcaa catcaccaat     360
ccagttttga atcaagaaat tgaggcattc agctttcctg aagatgcctc ctcatctaga     420
ctctctgaag accgagttgt cagcgtgagc ttcagagttc tctacccaat cgtgattacc     480
agtcttggag tgttctacga tgccagtgat gttggttttc aaaggaacat cacagtcaag     540
ttgtatcaga cagagcagga ggaggccctt ttcatcgccc gattcagtcc tccaagttgt     600
ggcgtacaag tgaacaagct ctggtataag cccgtggaac agttcatctt accagagagc     660
tttgaaggta caatcgtgtg ggaaagccaa gatctccatg gcctcgtgtc cagaaacctg     720
cacagagtga cagtgaatga tggaggggt gttctcagag tccttgcagc tggggaaggg     780
gcactgcctc atgaattcat ggaaggtgtg gagggagttg cgggtggctt tatctacact     840
gttcaggaag gtgatgcact attaagaagc ctttattctc ggccccagag acttgcagat     900
cacatacagg atctgcaggt ggaagatgcc ttactgcagg aggaaagcag tgtccatgac     960
gacattgtct tcgtggatgt tgtggatact taccggaatg ttcctgcaaa attactgaac    1020
ttctatagat ggactgtgga atccaccagc ttcgatttgc tgctcaagac agatgacgac    1080
tgttatatag acttagaagc tgtgtttaat agaattgctc agaagaatct agatgggcct    1140 aattttttggt ggggaaattt caggttgaat tgggcagtgg acagaaccgg aaaatggcag    1200
gagctggaat acccgagccc ggcttaccct gcctttgcat gtgggtcagg gtatgtgatc    1260
tccaaggata tcgttgactg gctggcaggc aactccagaa ggttaaagac ctatcagggt    1320
gaagatgtca gcatgggcat ttggatggca gccataggac ctaaaagaca ccaggacagc    1380
ctgtggctgt gtgagaaaac ctgtgagaca ggaatgctgt cttctcctca gtactcacca    1440
gaagagctga gcaaactctg gaactgaag gagctgtgtg gggatccttg tcagtgtgaa    1500
gcaaaagtac gatga                                                    1515

<210> SEQ ID NO 4
<211> LENGTH: 504
<212> TYPE: PRT
<213> ORGANISM: Mouse

<400> SEQUENCE: 4

Met Arg Asn Trp Leu Val Leu Leu Cys Pro Cys Val Leu Gly Ala Ala
1               5                   10                  15

Leu His Leu Trp His Leu Trp Leu Arg Ser Pro Pro Asp Pro His Asn
```

```
                  20                  25                  30
Thr Gly Pro Ser Ala Ala Asp Gln Ser Ala Leu Phe Pro His Trp Lys
            35                  40                  45

Phe Ser His Tyr Asp Val Val Gly Val Leu Ser Ala Arg Asn Asn
50                  55                  60

His Glu Leu Arg Asn Val Ile Arg Asn Thr Trp Leu Lys Asn Leu Leu
65                  70                  75                  80

His His Pro Thr Leu Ser Gln Arg Val Leu Val Lys Phe Ile Ile Gly
                85                  90                  95

Ala Arg Gly Cys Glu Val Pro Val Glu Asp Arg Glu Asp Pro Tyr Ser
            100                 105                 110

Cys Arg Leu Leu Asn Ile Thr Asn Pro Val Leu Asn Gln Glu Ile Glu
            115                 120                 125

Ala Phe Ser Phe Pro Glu Asp Ala Ser Ser Arg Leu Ser Glu Asp
            130                 135                 140

Arg Val Val Ser Val Ser Phe Arg Val Leu Tyr Pro Ile Val Ile Thr
145                 150                 155                 160

Ser Leu Gly Val Phe Tyr Asp Ala Ser Asp Val Gly Phe Gln Arg Asn
                165                 170                 175

Ile Thr Val Lys Leu Tyr Gln Thr Glu Gln Glu Ala Leu Phe Ile
            180                 185                 190

Ala Arg Phe Ser Pro Pro Ser Cys Gly Val Gln Val Asn Lys Leu Trp
            195                 200                 205

Tyr Lys Pro Val Glu Gln Phe Ile Leu Pro Glu Ser Phe Glu Gly Thr
            210                 215                 220

Ile Val Trp Glu Ser Gln Asp Leu His Gly Leu Val Ser Arg Asn Leu
225                 230                 235                 240

His Arg Val Thr Val Asn Asp Gly Gly Val Leu Arg Val Leu Ala
                245                 250                 255

Ala Gly Glu Gly Ala Leu Pro His Glu Phe Met Glu Gly Val Glu Gly
            260                 265                 270

Val Ala Gly Gly Phe Ile Tyr Thr Val Gln Glu Gly Asp Ala Leu Leu
            275                 280                 285

Arg Ser Leu Tyr Ser Arg Pro Gln Arg Leu Ala Asp His Ile Gln Asp
290                 295                 300

Leu Gln Val Glu Asp Ala Leu Leu Gln Glu Ser Ser Val His Asp
305                 310                 315                 320

Asp Ile Val Phe Val Asp Val Asp Thr Tyr Arg Asn Val Pro Ala
                325                 330                 335

Lys Leu Leu Asn Phe Tyr Arg Trp Thr Val Glu Ser Thr Ser Phe Asp
            340                 345                 350

Leu Leu Leu Lys Thr Asp Asp Cys Tyr Ile Asp Leu Glu Ala Val
            355                 360                 365

Phe Asn Arg Ile Ala Gln Lys Asn Leu Asp Gly Pro Asn Phe Trp Trp
            370                 375                 380

Gly Asn Phe Arg Leu Asn Trp Ala Val Asp Arg Thr Gly Lys Trp Gln
385                 390                 395                 400

Glu Leu Glu Tyr Pro Ser Pro Ala Tyr Pro Ala Phe Ala Cys Gly Ser
                405                 410                 415

Gly Tyr Val Ile Ser Lys Asp Ile Val Asp Trp Leu Ala Gly Asn Ser
            420                 425                 430

Arg Arg Leu Lys Thr Tyr Gln Gly Glu Asp Val Ser Met Gly Ile Trp
            435                 440                 445
```

```
Met Ala Ala Ile Gly Pro Lys Arg His Gln Asp Ser Leu Trp Leu Cys
        450                 455                 460
Glu Lys Thr Cys Glu Thr Gly Met Leu Ser Ser Pro Gln Tyr Ser Pro
465                 470                 475                 480
Glu Glu Leu Ser Lys Leu Trp Glu Leu Lys Glu Leu Cys Gly Asp Pro
                485                 490                 495
Cys Gln Cys Glu Ala Lys Val Arg
            500

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: 5'
      synthetic primer for PCR

<400> SEQUENCE: 5
cccaagcttg ggcctgcaga tcagttggcc ttatttc                         37

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: 3'
      synthetic primer for PCR

<400> SEQUENCE: 6
aacgcggatc cgcgctgtta tcttgcttga catcgacaag ga                   42

<210> SEQ ID NO 7
<211> LENGTH: 56
<212> TYPE: DNA
<213> ORGANISM: Artificial Sequence
<220> FEATURE:
<223> OTHER INFORMATION: Description of Artificial Sequence: 5'
      synthetic primer for PCR

<400> SEQUENCE: 7
ggggacaagt ttgtacaaaa aagcaggctt ccctgcagat cagttggcct tatttc    56

<210> SEQ ID NO 8
<211> LENGTH: 58
<212> TYPE: DNA
<213> ORGANISM: Artificial Sequence
<220> FEATURE:
<223> OTHER INFORMATION: Description of Artificial Sequence: 3'
      synthetic primer for PCR

<400> SEQUENCE: 8
ggggaccact ttgtacaaga aagctgggtc ctgttatctt gcttgacatc gacaagga  58

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Igkappa
      signal peptide

<400> SEQUENCE: 9

Met His Phe Gln Val Gln Ile Phe Ser Phe Leu Leu Ile Ser Ala Ser
1               5                   10                  15
Val Ile Met Ser Arg Gly
            20
```

```
<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: FLAG
      peptide

<400> SEQUENCE: 10

Asp Tyr Lys Asp Asp Asp Asp Lys
1               5

<210> SEQ ID NO 11
<211> LENGTH: 94
<212> TYPE: DNA
<213> ORGANISM: Artificial Sequence
<220> FEATURE:
<223> OTHER INFORMATION: Description of Artificial Sequence: synthetic
      primer OT3

<400> SEQUENCE: 11
gatcatgcat tttcaagtgc agattttcag cttcctgcta atcagtgcct cagtcataat      60
gtcacgtgga gattacaagg acgacgatga caag                                  94

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: synthetic
      primer OT20

<400> SEQUENCE: 12
cgggatccat gcattttcaa gtgcag                                           26

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: synthetic
      primer OT21

<400> SEQUENCE: 13
ggaattcttg tcatcgtcgt ccttg                                            25

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: 5'
      synthetic primer for PCR

<400> SEQUENCE: 14
ggagtgttct acgatgccaa t                                                21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: 3'
      synthetic primer for PCR

<400> SEQUENCE: 15
```

-continued ctgaagcgag caatgaagag                                                  20

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: TaqMan
      synthetic probe

<400> SEQUENCE: 16
cactgtcaaa ctttatcagg cagaacaaga gg                                    32

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: 5'
      synthetic primer for PCR

<400> SEQUENCE: 17
cccaagcttg ggagcgcggc agatcaatca gccttat                               37

<210> SEQ ID NO 18
<211> LENGTH: 53
<212> TYPE: DNA
<213> ORGANISM: Artificial Sequence
<220> FEATURE:
<223> OTHER INFORMATION: Description of Artificial Sequence: 3'
      synthetic primer for PCR

<400> SEQUENCE: 18
ttttcctttt gcggccgctt ttttcctttc atcgtacttt tgcttcacac tga             53

<210> SEQ ID NO 19
<211> LENGTH: 248
<212> TYPE: PRT
<213> ORGANISM: Homo sapiens
<220> FEATURE:
<223> OTHER INFORMATION: b3Gal-T1

<400> SEQUENCE: 19

Phe Leu Val Ile Leu Ile Ser Thr Thr His Lys Glu Phe Asp Ala Arg
1               5                   10                  15

Gln Ala Ile Arg Glu Thr Trp Gly Asp Glu Asn Asn Phe Lys Gly Ile
            20                  25                  30

Lys Ile Ala Thr Leu Phe Leu Leu Gly Lys Asn Ala Asp Pro Val Leu
        35                  40                  45

Asn Gln Met Val Glu Gln Glu Ser Gln Ile Phe His Asp Ile Ile Val
    50                  55                  60

Glu Asp Phe Ile Asp Ser Tyr His Asn Leu Thr Leu Lys Thr Leu Met
65                  70                  75                  80

Gly Met Arg Trp Val Ala Thr Phe Cys Ser Lys Ala Lys Tyr Val Met
                85                  90                  95

Lys Thr Asp Ser Asp Ile Phe Val Asn Met Asp Asn Leu Ile Tyr Lys
            100                 105                 110

Leu Leu Lys Pro Ser Thr Lys Pro Arg Arg Arg Tyr Phe Thr Gly Tyr
        115                 120                 125

Val Ile Asn Gly Gly Pro Ile Arg Asp Val Arg Ser Lys Trp Tyr Met
    130                 135                 140

Pro Arg Asp Leu Tyr Pro Asp Ser Asn Tyr Pro Pro Phe Cys Ser Gly
145                 150                 155                 160

```
Thr Gly Tyr Ile Phe Ser Ala Asp Val Ala Glu Leu Ile Tyr Lys Thr
                165                 170                 175

Ser Leu His Thr Arg Leu Leu His Leu Glu Asp Val Tyr Val Gly Leu
            180                 185                 190

Cys Leu Arg Lys Leu Gly Ile His Pro Phe Gln Asn Ser Gly Phe Asn
            195                 200                 205

His Trp Lys Met Ala Tyr Ser Leu Cys Arg Tyr Arg Val Ile Thr
            210                 215                 220

Val His Gln Ile Ser Pro Glu Met His Arg Ile Trp Asn Asp Met
225             230                 235                 240

Ser Ser Lys Lys His Leu Arg Cys
            245
```

<210> SEQ ID NO 20
<211> LENGTH: 271
<212> TYPE: PRT
<213> ORGANISM: Homo sapiens
<220> FEATURE:
<223> OTHER INFORMATION: b3Gal-T2

<400> SEQUENCE: 20

```
Phe Leu Ile Leu Leu Ile Ala Ala Glu Pro Gly Gln Ile Glu Ala Arg
1               5                   10                  15

Arg Ala Ile Arg Gln Thr Trp Gly Asn Glu Ser Leu Ala Pro Gly Ile
            20                  25                  30

Gln Ile Thr Arg Ile Phe Leu Leu Gly Leu Ser Ile Lys Leu Asn Gly
            35                  40                  45

Tyr Leu Gln Arg Ala Ile Leu Glu Glu Ser Arg Gln Tyr His Asp Ile
50                  55                  60

Ile Gln Gln Glu Tyr Leu Asp Thr Tyr Tyr Asn Leu Thr Ile Lys Thr
65              70                  75                  80

Leu Met Gly Met Asn Trp Val Ala Thr Tyr Cys Pro His Ile Pro Tyr
                85                  90                  95

Val Met Lys Thr Asp Ser Asp Met Phe Val Asn Thr Glu Tyr Leu Ile
                100                 105                 110

Asn Lys Leu Leu Lys Pro Asp Leu Pro Pro Arg His Asn Tyr Phe Thr
            115                 120                 125

Gly Tyr Leu Met Arg Gly Tyr Ala Pro Asn Arg Asn Lys Asp Ser Lys
            130                 135                 140

Trp Tyr Met Pro Pro Asp Leu Tyr Pro Ser Arg Tyr Pro Val Phe
145             150                 155                 160

Cys Ser Gly Thr Gly Tyr Val Phe Ser Gly Asp Leu Ala Glu Lys Ile
                165                 170                 175

Phe Lys Val Ser Leu Gly Ile Arg Arg Leu His Leu Glu Asp Val Tyr
            180                 185                 190

Val Gly Ile Cys Leu Ala Lys Leu Arg Ile Asp Pro Val Pro Pro
            195                 200                 205

Asn Glu Phe Val Phe Asn His Trp Arg Val Ser Tyr Ser Ser Cys Lys
            210                 215                 220

Tyr Ser His Leu Ile Thr Ser His Gln Phe Gln Pro Ser Glu Leu Ile
225             230                 235                 240

Lys Tyr Trp Asn His Leu Gln Gln Asn Lys His Asn Ala Cys Ala Asn
            245                 250                 255

Ala Ala Lys Glu Lys Ala Gly Arg Tyr Arg His Arg Lys Leu His
            260                 265                 270
```

```
<210> SEQ ID NO 21
<211> LENGTH: 253
<212> TYPE: PRT
<213> ORGANISM: Homo sapiens
<220> FEATURE:
<223> OTHER INFORMATION: b3Gal-T3

<400> SEQUENCE: 21

Phe Leu Val Ile Leu Val Thr Ser His Pro Ser Asp Val Lys Ala Arg
1               5                   10                  15

Gln Ala Ile Arg Val Thr Trp Gly Glu Lys Lys Ser Trp Trp Gly Tyr
                20                  25                  30

Glu Val Leu Thr Phe Phe Leu Leu Gly Gln Glu Ala Glu Lys Glu Asp
            35                  40                  45

Lys Met Leu Ala Leu Ser Leu Glu Asp Glu His Leu Leu Tyr Gly Asp
    50                  55                  60

Ile Ile Arg Gln Asp Phe Leu Asp Thr Tyr Asn Asn Leu Thr Leu Lys
65                  70                  75                  80

Thr Ile Met Ala Phe Arg Trp Val Thr Glu Phe Cys Pro Asn Ala Lys
                85                  90                  95

Tyr Val Met Lys Thr Asp Thr Asp Val Phe Ile Asn Thr Gly Asn Leu
                100                 105                 110

Val Lys Tyr Leu Leu Asn Leu Asn His Ser Glu Lys Phe Phe Thr Gly
            115                 120                 125

Tyr Pro Leu Ile Asp Asn Tyr Ser Tyr Arg Gly Phe Tyr Gln Lys Thr
    130                 135                 140

His Ile Ser Tyr Gln Glu Tyr Pro Phe Lys Val Phe Pro Pro Tyr Cys
145                 150                 155                 160

Ser Gly Leu Gly Tyr Ile Met Ser Arg Asp Leu Val Pro Arg Ile Tyr
                165                 170                 175

Glu Met Met Gly His Val Lys Pro Ile Lys Phe Glu Asp Val Tyr Val
                180                 185                 190

Gly Ile Cys Leu Asn Leu Leu Lys Val Asn Ile His Ile Pro Glu Asp
            195                 200                 205

Thr Asn Leu Phe Phe Leu Tyr Arg Ile His Leu Asp Val Cys Gln Leu
    210                 215                 220

Arg Arg Val Ile Ala Ala His Gly Phe Ser Ser Lys Glu Ile Ile Thr
225                 230                 235                 240

Phe Trp Gln Val Met Leu Arg Asn Thr Thr Cys His Tyr
                245                 250

<210> SEQ ID NO 22
<211> LENGTH: 253
<212> TYPE: PRT
<213> ORGANISM: Homo sapiens
<220> FEATURE:
<223> OTHER INFORMATION: b3Gal-T5

<400> SEQUENCE: 22

Phe Leu Val Leu Leu Val Thr Ser Ser His Lys Gln Leu Ala Glu Arg
1               5                   10                  15

Met Ala Ile Arg Gln Thr Trp Gly Lys Glu Arg Met Val Lys Gly Lys
                20                  25                  30

Gln Leu Lys Thr Phe Phe Leu Leu Gly Thr Thr Ser Ser Ala Ala Glu
            35                  40                  45

Thr Lys Glu Val Asp Gln Glu Ser Gln Arg His Gly Asp Ile Ile Gln
    50                  55                  60
```

```
Lys Asp Phe Leu Asp Val Tyr Tyr Asn Leu Thr Leu Lys Thr Met Met
 65                  70                  75                  80

Gly Ile Glu Trp Val His Arg Phe Cys Pro Gln Ala Ala Phe Val Met
                 85                  90                  95

Lys Thr Asp Ser Asp Met Phe Ile Asn Val Asp Tyr Leu Thr Glu Leu
            100                 105                 110

Leu Leu Lys Lys Asn Arg Thr Thr Arg Phe Phe Thr Gly Phe Leu Lys
        115                 120                 125

Leu Asn Glu Phe Pro Ile Arg Gln Pro Phe Ser Lys Trp Phe Val Ser
    130                 135                 140

Lys Ser Glu Tyr Pro Trp Asp Arg Tyr Pro Pro Phe Cys Ser Gly Thr
145                 150                 155                 160

Gly Tyr Val Phe Ser Gly Asp Val Ala Ser Gln Val Tyr Asn Val Ser
                165                 170                 175

Lys Ser Val Pro Tyr Ile Lys Leu Glu Asp Val Phe Val Gly Leu Cys
            180                 185                 190

Leu Glu Arg Leu Asn Ile Arg Leu Glu Glu Leu His Ser Gln Pro Thr
        195                 200                 205

Phe Phe Pro Gly Gly Leu Arg Phe Ser Val Cys Leu Phe Arg Arg Ile
    210                 215                 220

Val Ala Cys His Phe Ile Lys Pro Arg Thr Leu Leu Asp Tyr Trp Gln
225                 230                 235                 240

Ala Leu Glu Asn Ser Arg Gly Glu Asp Cys Pro Pro Val
                245                 250
```

<210> SEQ ID NO 23
<211> LENGTH: 272
<212> TYPE: PRT
<213> ORGANISM: Homo sapiens
<220> FEATURE:
<223> OTHER INFORMATION: b3Gal-T6

<400> SEQUENCE: 23

```
Phe Leu Ala Val Leu Val Ala Ser Ala Pro Arg Ala Ala Glu Arg Arg
  1               5                  10                  15

Ser Val Ile Arg Ser Thr Trp Leu Ala Arg Arg Gly Ala Pro Gly Asp
                 20                  25                  30

Val Trp Ala Arg Phe Ala Val Gly Thr Ala Gly Leu Gly Ala Glu Glu
             35                  40                  45

Arg Arg Ala Leu Glu Arg Glu Gln Ala Arg His Gly Asp Leu Leu Leu
         50                  55                  60

Leu Pro Ala Leu Arg Asp Ala Tyr Glu Asn Leu Thr Ala Lys Val Leu
 65                  70                  75                  80

Ala Met Leu Ala Trp Leu Asp Glu His Val Ala Phe Glu Phe Val Leu
                 85                  90                  95

Lys Ala Asp Asp Asp Ser Phe Ala Arg Leu Asp Ala Leu Leu Ala Glu
            100                 105                 110

Leu Arg Ala Arg Glu Pro Ala Arg Arg Arg Leu Tyr Trp Gly Phe Phe
        115                 120                 125

Phe Ser Gly Arg Gly Arg Val Lys Pro Gly Gly Arg Trp Arg Glu Ala
    130                 135                 140

Ala Trp Gln Leu Cys Asp Tyr Tyr Leu Pro Tyr Ala Leu Gly Gly Gly
145                 150                 155                 160

Tyr Val Leu Ser Ala Asp Leu Val His Tyr Leu Arg Leu Ser Arg Asp
                165                 170                 175

Tyr Leu Arg Ala Trp His Ser Glu Asp Val Ser Leu Gly Ala Trp Leu
```

```
            180                 185                 190
Ala Pro Val Asp Val Gln Arg Glu His Asp Pro Arg Phe Asp Thr Glu
            195                 200                 205

Tyr Arg Ser Arg Gly Cys Ser Asn Gln Tyr Leu Val Thr His Lys Gln
            210                 215                 220

Ser Leu Glu Asp Met Leu Glu Lys His Ala Thr Leu Ala Arg Glu Gly
225                 230                 235                 240

Arg Leu Cys Lys Arg Glu Val Gln Leu Arg Leu Ser Tyr Val Tyr Asp
            245                 250                 255

Trp Ser Ala Pro Pro Ser Gln Cys Cys Gln Arg Arg Glu Gly Ile Pro
            260                 265                 270

<210> SEQ ID NO 24
<211> LENGTH: 255
<212> TYPE: PRT
<213> ORGANISM: Homo sapiens
<220> FEATURE:
<223> OTHER INFORMATION: b3GnT2

<400> SEQUENCE: 24

Phe Leu Leu Leu Ala Ile Lys Ser Leu Thr Pro His Phe Ala Arg Arg
1               5                   10                  15

Gln Ala Ile Arg Glu Ser Trp Gly Gln Glu Ser Asn Ala Gly Asn Gln
            20                  25                  30

Thr Val Val Arg Val Phe Leu Leu Gly Gln Thr Pro Pro Glu Asp Asn
            35                  40                  45

His Pro Asp Leu Ser Asp Met Leu Lys Phe Glu Ser Glu Lys His Gln
50                  55                  60

Asp Ile Leu Met Trp Asn Tyr Arg Asp Thr Phe Phe Asn Leu Ser Leu
65                  70                  75                  80

Lys Glu Val Leu Phe Leu Arg Trp Val Ser Thr Ser Cys Pro Asp Thr
            85                  90                  95

Glu Phe Val Phe Lys Gly Asp Asp Val Phe Val Asn Thr His His His
            100                 105                 110

Ile Leu Asn Tyr Leu Asn Ser Leu Ser Lys Thr Lys Ala Lys Asp Leu
            115                 120                 125

Phe Ile Gly Asp Val Ile His Asn Ala Gly Pro His Arg Asp Lys Lys
130                 135                 140

Leu Lys Tyr Tyr Ile Pro Glu Val Val Tyr Ser Gly Leu Tyr Pro Pro
145                 150                 155                 160

Tyr Ala Gly Gly Gly Gly Phe Leu Tyr Ser Gly His Leu Ala Leu Arg
            165                 170                 175

Leu Tyr His Ile Thr Asp Gln Val His Leu Tyr Pro Ile Asp Asp Val
            180                 185                 190

Tyr Thr Gly Met Cys Leu Gln Lys Leu Gly Leu Val Pro Glu Lys His
            195                 200                 205

Lys Gly Phe Arg Thr Phe Asp Ile Glu Glu Lys Asn Lys Asn Asn Ile
            210                 215                 220

Cys Ser Tyr Val Asp Leu Met Leu Val His Ser Arg Lys Pro Gln Glu
225                 230                 235                 240

Met Ile Asp Ile Trp Ser Gln Leu Gln Ser Ala His Leu Lys Cys
            245                 250                 255

<210> SEQ ID NO 25
<211> LENGTH: 265
<212> TYPE: PRT
<213> ORGANISM: Homo sapiens
```

-continued

<220> FEATURE:
<223> OTHER INFORMATION: b3GnT3

<400> SEQUENCE: 25

Phe Leu Leu Leu Val Ile Lys Ser Ser Pro Ser Asn Tyr Val Arg Arg
1               5                   10                  15

Glu Leu Leu Arg Arg Thr Trp Gly Arg Glu Lys Val Arg Gly Leu
            20                  25                  30

Gln Leu Arg Leu Leu Phe Leu Val Gly Thr Ala Ser Asn Pro His Glu
        35                  40                  45

Ala Arg Lys Val Asn Arg Leu Leu Glu Leu Glu Ala Gln Thr His Gly
50                  55                  60

Asp Ile Leu Gln Trp Asp Phe His Asp Ser Phe Phe Asn Leu Thr Leu
65                  70                  75                  80

Lys Gln Val Leu Phe Leu Gln Trp Gln Glu Thr Arg Cys Ala Asn Ala
                85                  90                  95

Ser Phe Val Leu Asn Gly Asp Asp Val Phe Ala His Thr Asp Asn
            100                 105                 110

Met Val Phe Tyr Leu Gln Asp His Asp Pro Gly Arg His Leu Phe Val
        115                 120                 125

Gly Gln Leu Ile Gln Asn Val Gly Pro Ile Arg Ala Phe Trp Ser Lys
130                 135                 140

Tyr Tyr Val Pro Glu Val Thr Gln Asn Glu Arg Tyr Pro Pro Tyr
145                 150                 155                 160

Cys Gly Gly Gly Gly Phe Leu Leu Ser Arg Phe Thr Ala Ala Ala Leu
                165                 170                 175

Arg Arg Ala Ala His Val Leu Asp Ile Phe Pro Ile Asp Asp Val Phe
            180                 185                 190

Leu Gly Met Cys Leu Glu Leu Glu Gly Leu Lys Pro Ala Ser His Ser
        195                 200                 205

Gly Ile Arg Thr Ser Gly Val Arg Ala Pro Ser Gln His Leu Ser Ser
210                 215                 220

Phe Asp Pro Cys Phe Tyr Arg Asp Leu Leu Leu Val His Arg Phe Leu
225                 230                 235                 240

Pro Tyr Glu Met Leu Leu Met Trp Asp Ala Leu Asn Gln Pro Asn Leu
                245                 250                 255

Thr Cys Gly Asn Gln Thr Gln Ile Tyr
            260                 265

<210> SEQ ID NO 26
<211> LENGTH: 260
<212> TYPE: PRT
<213> ORGANISM: Homo sapiens
<220> FEATURE:
<223> OTHER INFORMATION: b3GnT4

<400> SEQUENCE: 26

Phe Leu Leu Leu Ala Ile Lys Ser Gln Pro Gly His Val Glu Arg Arg
1               5                   10                  15

Ala Ala Ile Arg Ser Thr Trp Gly Arg Val Gly Trp Ala Arg Gly
            20                  25                  30

Arg Gln Leu Lys Leu Val Phe Leu Leu Gly Val Ala Gly Ser Ala Pro
        35                  40                  45

Pro Ala Gln Leu Leu Ala Tyr Glu Ser Arg Glu Phe Asp Asp Ile Leu
50                  55                  60

Gln Trp Asp Phe Thr Glu Asp Phe Phe Asn Leu Thr Leu Lys Glu Leu
65                  70                  75                  80

His Leu Gln Arg Trp Val Ala Ala Cys Pro Gln Ala His Phe Met
                85                  90                  95

Leu Lys Gly Asp Asp Val Phe Val His Val Pro Asn Val Leu Glu
            100                 105                 110

Phe Leu Asp Gly Trp Asp Pro Ala Gln Asp Leu Leu Val Gly Asp Val
        115                 120                 125

Ile Arg Gln Ala Leu Pro Asn Arg Asn Thr Lys Val Lys Tyr Phe Ile
130                 135                 140

Pro Pro Ser Met Tyr Arg Ala Thr His Tyr Pro Pro Tyr Ala Gly Gly
145                 150                 155                 160

Gly Gly Tyr Val Met Ser Arg Ala Thr Val Arg Arg Leu Gln Ala Ile
                165                 170                 175

Met Glu Asp Ala Glu Leu Phe Pro Ile Asp Asp Val Phe Val Gly Met
            180                 185                 190

Cys Leu Arg Arg Leu Gly Leu Ser Pro Met His His Ala Gly Phe Lys
        195                 200                 205

Thr Phe Gly Ile Arg Arg Pro Leu Asp Pro Leu Asp Pro Cys Leu Tyr
    210                 215                 220

Arg Gly Leu Leu Leu Val His Arg Leu Ser Pro Leu Glu Met Trp Thr
225                 230                 235                 240

Met Trp Ala Leu Val Thr Asp Glu Gly Leu Lys Cys Ala Ala Gly Pro
                245                 250                 255

Ile Pro Gln Arg
            260

<210> SEQ ID NO 27
<211> LENGTH: 290
<212> TYPE: PRT
<213> ORGANISM: Homo sapiens
<220> FEATURE:
<223> OTHER INFORMATION: b3GnT5

<400> SEQUENCE: 27

Leu Leu Leu Leu Phe Val Lys Thr Ala Pro Glu Asn Tyr Asp Arg Arg
1               5                   10                  15

Ser Gly Ile Arg Arg Thr Trp Gly Asn Glu Asn Tyr Val Arg Ser Gln
            20                  25                  30

Leu Asn Ala Asn Ile Lys Thr Leu Phe Ala Leu Gly Thr Pro Asn Pro
        35                  40                  45

Leu Glu Gly Glu Glu Leu Gln Arg Lys Leu Ala Trp Glu Asp Gln Arg
    50                  55                  60

Tyr Asn Asp Ile Ile Gln Gln Asp Phe Val Asp Ser Phe Tyr Asn Leu
65                  70                  75                  80

Thr Leu Lys Leu Leu Met Gln Phe Ser Trp Ala Asn Thr Tyr Cys Pro
                85                  90                  95

His Ala Lys Phe Leu Met Thr Ala Asp Asp Ile Phe Ile His Met
            100                 105                 110

Pro Asn Leu Ile Glu Tyr Leu Gln Ser Leu Glu Gln Ile Gly Val Gln
        115                 120                 125

Asp Phe Trp Ile Gly Arg Val His Arg Gly Ala Pro Pro Ile Arg Asp
    130                 135                 140

Lys Ser Ser Lys Tyr Tyr Val Ser Tyr Glu Met Tyr Gln Trp Pro Ala
145                 150                 155                 160

Tyr Pro Asp Tyr Thr Ala Gly Ala Ala Tyr Val Ile Ser Gly Asp Val
                165                 170                 175

-continued

```
Ala Ala Lys Val Tyr Glu Ala Ser Gln Thr Leu Asn Ser Ser Leu Tyr
            180                 185                 190

Ile Asp Asp Val Phe Met Gly Leu Cys Ala Asn Lys Ile Gly Ile Val
            195                 200                 205

Pro Gln Asp His Val Phe Phe Ser Gly Glu Gly Lys Thr Pro Tyr His
            210                 215                 220

Pro Cys Ile Tyr Glu Lys Met Met Thr Ser His Gly His Leu Glu Asp
225                 230                 235                 240

Leu Gln Asp Leu Trp Lys Asn Ala Thr Asp Pro Lys Val Lys Thr Ile
            245                 250                 255

Ser Lys Gly Phe Phe Gly Gln Ile Tyr Cys Arg Leu Met Lys Ile Ile
            260                 265                 270

Leu Leu Cys Lys Ile Ser Tyr Val Asp Thr Tyr Pro Cys Arg Ala Ala
            275                 280                 285

Phe Ile
    290

<210> SEQ ID NO 28
<211> LENGTH: 234
<212> TYPE: PRT
<213> ORGANISM: Homo sapiens
<220> FEATURE:
<223> OTHER INFORMATION: b3Gal-T4

<400> SEQUENCE: 28

Phe Leu Leu Ile Leu Val Cys Thr Ala Pro Glu Asn Leu Asn Gln Arg
1               5                   10                  15

Asn Ala Ile Arg Ala Ser Trp Gly Gly Leu Arg Glu Ala Arg Gly Leu
            20                  25                  30

Arg Val Gln Thr Leu Phe Leu Leu Gly Glu Pro Asn Ala Gln His Pro
        35                  40                  45

Val Trp Gly Ser Gln Gly Ser Asp Leu Ala Ser Glu Ser Ala Ala Gln
    50                  55                  60

Gly Asp Ile Leu Gln Ala Ala Phe Gln Asp Ser Tyr Arg Asn Leu Thr
65                  70                  75                  80

Leu Lys Thr Leu Ser Gly Leu Asn Trp Ala Glu Lys His Cys Pro Met
            85                  90                  95

Ala Arg Tyr Val Leu Lys Thr Asp Asp Val Tyr Val Asn Val Pro
            100                 105                 110

Glu Leu Val Ser Glu Leu Val Leu Arg Gly Gly Arg Trp Gly Gln Trp
            115                 120                 125

Glu Arg Ser Thr Glu Pro Gln Arg Glu Ala Glu Gln Glu Gly Gly Gln
130                 135                 140

Val Leu His Ser Glu Glu Val Pro Leu Leu Tyr Leu Gly Arg Val His
145                 150                 155                 160

Trp Arg Val Asn Pro Ser Arg Thr Pro Gly Gly Arg His Arg Val Ser
            165                 170                 175

Glu Glu Gln Trp Pro His Thr Trp Gly Pro Phe Pro Pro Tyr Ala Ser
            180                 185                 190

Gly Thr Gly Tyr Val Leu Ser Ala Ser Ala Val Gln Leu Ile Leu Lys
        195                 200                 205

Val Ala Ser Arg Ala Pro Leu Leu Pro Leu Glu Asp Val Phe Val Gly
    210                 215                 220

Val Ser Ala Arg Arg Gly Gly Leu Ala Pro
225                 230
```